(12) United States Patent
Kondo et al.

(10) Patent No.: US 10,398,788 B2
(45) Date of Patent: Sep. 3, 2019

(54) POLYMER AND CONTRAST AGENT FOR PHOTOACOUSTIC IMAGING INCLUDING THE POLYMER

(71) Applicant: CANON KABUSHIKI KAISHA, Tokyo (JP)

(72) Inventors: Teruyuki Kondo, Kyoto (JP); Yasuhiro Aoyama, Kyoto (JP); Hisatsugu Yamada, Kyoto (JP); Yoshinori Hasegawa, Kyoto (JP); Shinsuke Sando, Kyoto (JP); Yu Kimura, Kyoto (JP); Natsuki Matsumoto, Kyoto (JP); Fumio Yamauchi, Yokohama (JP); Tetsuya Yano, Tsukuba (JP); Masato Minami, Kawasaki (JP); Atsushi Takahashi, Ebina (JP); Kengo Kanazaki, Yokohama (JP); Satoshi Ogawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 32 days.

(21) Appl. No.: 15/513,035

(22) PCT Filed: Oct. 9, 2015

(86) PCT No.: PCT/JP2015/079388
§ 371 (c)(1),
(2) Date: Mar. 21, 2017

(87) PCT Pub. No.: WO2016/063817
PCT Pub. Date: Apr. 28, 2016

(65) Prior Publication Data
US 2017/0333575 A1 Nov. 23, 2017

(30) Foreign Application Priority Data

Oct. 24, 2014 (JP) .................................. 2014-217451
Mar. 10, 2015 (JP) .................................. 2015-047073

(51) Int. Cl.
*A61K 49/22* (2006.01)
*A61K 49/00* (2006.01)

(52) U.S. Cl.
CPC ........ *A61K 49/221* (2013.01); *A61K 49/0032* (2013.01); *A61K 49/0034* (2013.01); *A61K 49/0054* (2013.01)

(58) Field of Classification Search
None
See application file for complete search history.

(56) References Cited

U.S. PATENT DOCUMENTS

| | | | |
|---|---|---|---|
| 8,753,608 B2 | 6/2014 | Tabata et al. | |
| 9,132,203 B2 | 9/2015 | Tabata et al. | |
| 9,138,492 B2 | 9/2015 | Fukui et al. | |
| 9,517,278 B2 | 12/2016 | Takahashi et al. | |
| 9,592,307 B2 | 3/2017 | Yamauchi et al. | |
| 2011/0065212 A1 | 3/2011 | Ban et al. | |
| 2011/0263975 A1* | 10/2011 | Tolleshaug | A61K 49/0039 600/431 |
| 2012/0114563 A1 | 5/2012 | Carter et al. | |
| 2013/0323178 A1 | 12/2013 | Yamauchi et al. | |
| 2014/0024776 A1* | 1/2014 | Charles | C08F 230/02 525/54.1 |
| 2015/0071861 A1 | 3/2015 | Kondo et al. | |
| 2015/0290345 A1 | 10/2015 | Takahashi et al. | |
| 2015/0374856 A1 | 12/2015 | Miki et al. | |
| 2016/0067359 A1 | 3/2016 | Fukui et al. | |
| 2016/0279271 A1 | 9/2016 | Yamauchi et al. | |

FOREIGN PATENT DOCUMENTS

| | | |
|---|---|---|
| JP | 2012-520856 A | 9/2012 |
| WO | 98/57667 A1 | 12/1998 |
| WO | 2010/106169 A1 | 9/2010 |
| WO | 2014/013730 A1 | 1/2014 |
| WO | 2014/013732 A1 | 1/2014 |
| WO | 2016/060277 A1 | 4/2016 |

OTHER PUBLICATIONS

Madsen et al., "Synthesis of Rhodamine 6G-Based Compounds for the ATRP Synthesis of Fluorescently Labeled Biocompatible Polymers," 12(6) Biomacromolecules 2225-2234 (Apr. 2011), Supplemental Content (Year: 2011).*

Jeppe Madsen et al., "Synthesis of Rhodamine 6G-Based Compounds for the ATRP Synthesis of Fluorescently Labeled Biocompatible Polymers," 12(6) Biomacromolecules 2225-2234 (Apr. 2011) (XP055201166).

Jeppe Madsen et al., "Nile Blue-Based Nanosized pH Sensors for Simultaneous Far-Red and Near-Infrared Live Bioimaging," 135(39) J. Am. Chem. Soc. 14863-14870 (Sep. 2013) (XP055239124).

Xueding Wang et al., "Noninvasive Photoacoustic Angiography of Animal Brains in vivo with Near-Infrared Light and an Optical Contrast Agent," 29(7) Opt. Lett. 730-732 (Apr. 2004) (XP055079408).

* cited by examiner

*Primary Examiner* — James W Rogers
(74) *Attorney, Agent, or Firm* — Venable LLP

(57) ABSTRACT

To provide a polymer having a high ratio of the amount thereof present in a tumor to the amount thereof present in blood (hereinafter, sometimes abbreviated as a tumor/blood ratio).

The polymer has phosphorylcholine (derivative) as a side chain and has a dye (near-infrared dye) having absorption in the near-infrared wavelength region bound to the polymer.

5 Claims, 13 Drawing Sheets

FIG. 5
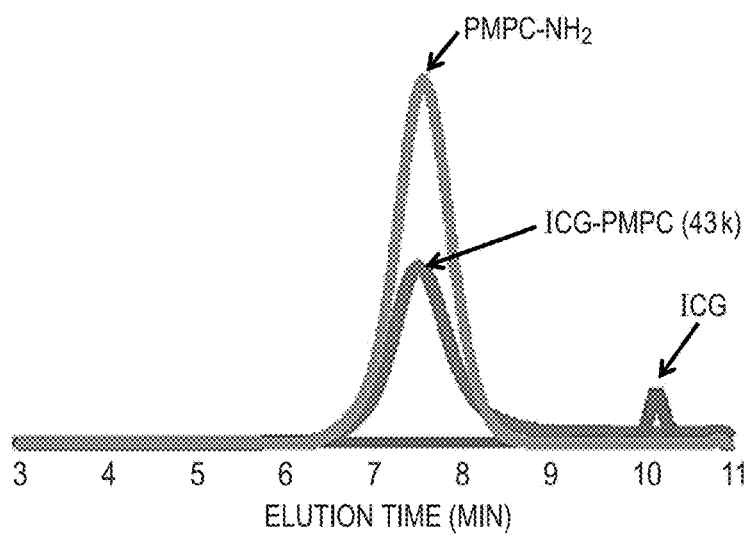
FIG. 6A
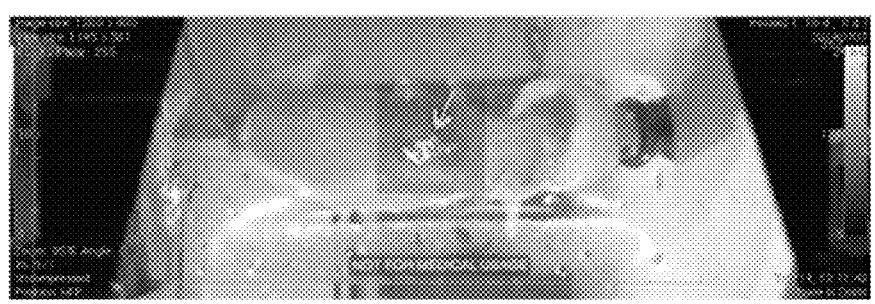
FIG. 6B

BEFORE ADMINISTRATION

48 HOURS AFTER ADMINISTRATION

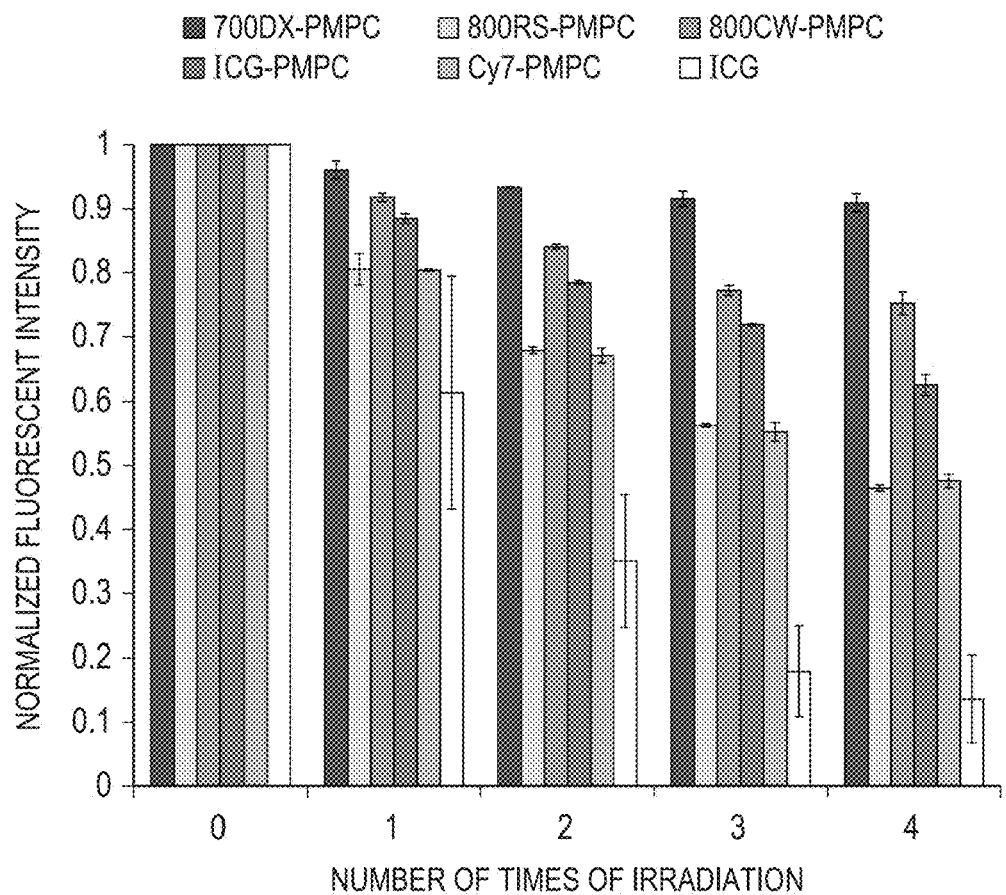

POLYMER AND CONTRAST AGENT FOR PHOTOACOUSTIC IMAGING INCLUDING THE POLYMER

TECHNICAL FIELD

The present invention relates to a polymer, and a contrast agent for photoacoustic imaging, including the polymer.

BACKGROUND ART

A photoacoustic tomography (hereinafter, sometimes abbreviated as "PAT") apparatus is known as one apparatus for visualizing information in a living body. In measurement using the PAT apparatus, an image in which the substance distribution in an object to be measured is computed can be obtained by measuring the intensity and the time of generation of a photoacoustic signal emitted from a substance (optical absorber) that absorbs light in the object to be measured, in irradiation of the object to be measured with light.

For the optical absorber, any substance can be here used as long as the substance absorbs light and emits an acoustic wave in a living body. For example, a blood vessel or a malignant tumor in a human body can be adopted for the optical absorber. Besides, molecules of indocyanine green (hereinafter, sometimes abbreviated as "ICG") and the like can also be administered into a body and utilized as a contrast agent. ICG well absorbs light in the near-infrared wavelength region, the light having a small influence in irradiation of a human body therewith and having a high permeability to a living body, and therefore can be suitably used as a contrast agent (sometimes abbreviated as a "photoacoustic contrast agent") in the PAT apparatus. In the present description, ICG refers to a compound represented by a structure of the following formula.

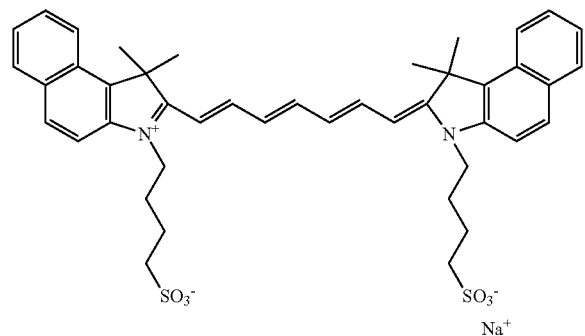

Herein, the counter ion may not be Na$^+$, and any counter ion such as H$^+$ or K$^+$ can be used.

It is known that, however, ICG has a very short half-life of about several minutes in blood.

PTL 1 reports an example in which a tumor accumulation is confirmed using a contrast agent in which polyethylene glycol (hereinafter, sometimes abbreviated as "PEG") is covalently bound to a near-infrared fluorescent dye. The near-infrared fluorescent dye can be bound to PEG to thereby allow the half-life in blood to be prolonged as compared with a single near-infrared fluorescent dye.

NPL 1 discloses a compound in which a rhodamine dye (maximum absorption wavelength: 530 nm) is bound to the terminal of a 2-methacryloyloxyethyl phosphorylcholine (sometimes abbreviated as "MPC") polymer.

CITATION LIST

Patent Literature

PTL 1: Japanese Patent Application Laid-Open No. 2012-520856

Not Patent Literature

NPL 1: BIOMACROMOLECULES, 12, 2225-2234 (2011)

SUMMARY OF INVENTION

Technical Problem

While the near-infrared fluorescent dye-bound PEG disclosed in PTL 1 exhibits a high tumor accumulation property, the PEG has a high retentivity in blood, and therefore has the problem of being low in tumor/blood ratio (tumor selectivity).

The rhodamine dye-bound MPC polymer disclosed in NPL 1 has a maximum absorption wavelength of around 530 nm. Light having a wavelength band in the visible region is highly absorbed by hemoglobin in blood, and it is thus difficult to detect in vivo the photoacoustic signal of the rhodamine dye-bound MPC polymer.

Accordingly, a compound exhibiting a high absorption coefficient in the near-infrared wavelength region, a high tumor accumulation property and a high tumor/blood ratio has been demanded as a photoacoustic contrast agent that enables to detect in vivo a signal and that has a higher tumor accumulation property.

The present invention has been made in view of such problems, and an object thereof is to provide a novel near-infrared dye-bound phosphorylcholine-containing polymer exhibiting a high absorption coefficient in the near-infrared wavelength region, a high tumor accumulation property and a high tumor/blood ratio, as well as a contrast agent for photoacoustic imaging, using the polymer.

Solution to Problem

The polymer according to the present invention is a polymer represented by formula (P2), in which a side chain is bound to a main chain via a linker or directly.

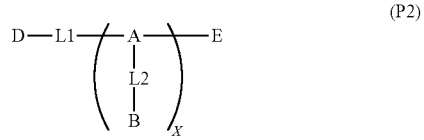

Herein, D represents a dye backbone of a dye having absorption in the near-infrared region, A represents the main chain of the polymer, L1 and L2 each independently represent a linker, L1 and L2 may not be present, x represents an integer of 1 or more, E represents a functional group, and B is represented by the following formula (s1).

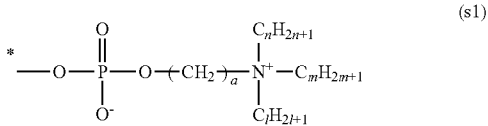

(s1)

In the formula (s1), a represents an integer of 1 or more and 6 or less, n, m and l each independently represent an integer of 1 to 3, and * represents binding to L2 or A. In the present description, an asterisk symbol made of five radial lines and an asterisk symbol made of six radial lines are used and such symbols have the same meaning.

Advantageous Effects of Invention

The polymer according to the present invention has a structure in which a hydrophilic phosphorylcholine-containing polymer and an organic dye having absorption in the near-infrared wavelength region, such as ICG, are covalently bound, and therefore the polymer has a high accumulation property in a tumor and the concentration thereof in blood is rapidly reduced. Therefore, the polymer according to the present invention is high in the ratio of the amount thereof present in a tumor to the amount thereof present in blood (sometimes abbreviated as the "tumor/blood ratio"), when administered into a body. Accordingly, a tumor can be photoacoustically imaged at a high sensitivity and a high contrast.

Further features of the present invention will become apparent from the following description of exemplary embodiments with reference to the attached drawings.

BRIEF DESCRIPTION OF DRAWINGS

FIG. 5 illustrates a superimposed diagram of respective GPC charts of ICG-PMPC (43 k) according to Example of the present invention, and PMPC-NH$_2$ and ICG dyes according to Example of the present invention.

FIG. 6A illustrates a superimposed image of an optical photograph and a photoacoustic imaging image (MIP image) surrounded with a white square frame, of a cancer-bearing mouse imaged before administration of ICG-PMPC (43 k) according to Example of the present invention. FIG. 6B illustrates a superimposed image of an optical photograph and a photoacoustic imaging image (MIP image) surrounded with a white square frame, of a cancer-bearing mouse imaged one day after administration of ICG-PMPC (43 k) according to Example of the present invention. Each white arrow indicates the position of a tumor.

FIG. 12A illustrates a superimposed image of an optical photograph and a photoacoustic image of the cancer-bearing mouse before administration.

FIG. 12B illustrates a superimposed image of an optical photograph and a photoacoustic image of the same mouse individual two days after administration. Each arrow in the Figure indicates a tumor position.

FIG. 13 illustrates respective photoacoustic images of the tumor region of the same mouse individual before administration and two days after administration.

FIG. 16 illustrates a list of the excitation wavelength (Ex) and the fluorescence emission wavelength (Em) of each of ICG-PMPC (48 k), Cy7-PMPC (58 k), 800RS-PMPC (57 k), 800CW-PMPC (57 k) and 700DX-PMPC (57 k) according to Examples of the present invention, and ICG according to Comparative Example. In the Figure, ICG-PMPC (48 k), Cy7-PMPC (58 k), 800RS-PMPC (57 k), 800CW-PMPC (57 k), 700DX-PMPC (57 k) and ICG are designated as ICG-PMPC, Cy7-PMPC, 800RS-PMPC, 800CW-PMPC, 700DX-PMPC and ICG, respectively.

FIG. 17 is a diagram illustrating photo-fading in laser irradiation of each of ICG-PMPC (48 k), Cy7-PMPC (58 k), 800RS-PMPC (57 k), 800CW-PMPC (57 k) and 700DX-PMPC (57 k) according to Examples of the present invention, and ICG according to Comparative Example. FIG. 17 illustrates respective normalized fluorescent intensities before and after laser irradiation. In the Figure, ICG-PMPC (48 k), Cy7-PMPC (58 k), 800RS-PMPC (57 k), 800CW-PMPC (57 k), 700DX-PMPC (57 k) and ICG are designated as ICG-PMPC, Cy7-PMPC, 800RS-PMPC, 800CW-PMPC, 700DX-PMPC and ICG, respectively.

FIG. 18 illustrates normalized fluorescent intensities of respective solutions before and after laser irradiation (fluorescent intensity at 536 nm in excitation at 480 nm). In the Figure, ICG-PMPC (48 k), Cy7-PMPC (58 k), 800RS-PMPC (57 k), 800CW-PMPC (57 k) and 700DX-PMPC (57 k) are designated as ICG-PMPC, Cy7-PMPC, 800RS-PMPC, 800CW-PMPC and 700DX-PMPC, respectively.

DESCRIPTION OF EMBODIMENTS

Figure 1:
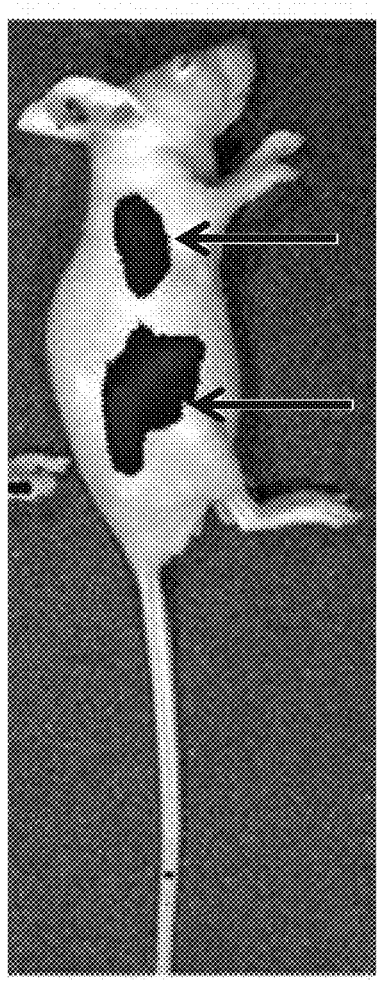
FIG. 1 illustrates a superimposed image of a near-infrared fluorescent image and a bright field image of a cancer-bearing mouse at 24 hours after administration of ICG-PMPC (18 k) according to Example of the present invention (each black arrow in the Figure indicates a tumor site).

Preferred embodiments of the present invention will now be described in detail in accordance with the accompanying drawings.

Hereinafter, embodiments of the present invention are described, but the present invention is not limited thereto. In the present description, k means 1000. For example, 18 k means 18000. In the present description, x or n indicating the number of repeating unit represent integers of 1 or more.

(Polymer)

A polymer according to the present embodiment is a polymer having phosphorylcholine (derivative) as a side chain, and the polymer is further bound to a dye (near-infrared dye) having absorption in the near-infrared wavelength region.

That is, the polymer is a polymer represented by formula (P2).

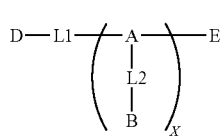

(P2)

In the formula (P2), D represents a dye backbone of a dye having absorption in the near-infrared region, A represents the main chain of the polymer, L1 and L2 each independently represent a linker, L1 and L2 may not be present, x represents an integer of 1 or more, and E represents the terminal of a repeating structure, in which the structure represents any of, for example, a residue and a functional group derived from a cationic polymerization initiator, but is not particularly limited. In the formula (P2), B is represented by the following formula (s1).

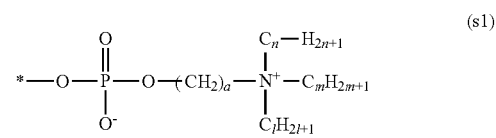

(s1)

In the formula (s1), a represents an integer of 1 or more and 6 or less, n, m and l each independently represent an integer of 1 to 3, and * represents binding to L2 or A.

Poly(2-methacryloyloxyethyl phosphorylcholine) (PMPC) is a hydrophilic polymer having a phosphorylcholine group as a side chain and has the property of suppression of protein adsorption, and therefore is used as a biomaterial.

On the other hand, PEG is known as a biocompatible hydrophilic polymer. While PEG can be dissolved in a wide variety of any solvents including a polar solvent and a non-polar solvent, PMPC is characterized by being well dissolved in water and methanol, but not being dissolved in a non-polar organic solvent and a polar organic solvent such as DMSO and DMF, unlike PEG.

ICG has the amphiphilic property of being dissolved in water, methanol, DMSO or the like and being easily mutually associated.

From the foregoing, it is considered with respect to ICG-bound PEG that high compatibility between ICG and PEG in blood results in a state where ICG is effectively covered with PEG. On the other hand, the compatibility of ICG with PMPC is considered to be lower than the compatibility thereof with PEG, and therefore a state is considered to be caused where ICG is not effectively covered with PMPC.

Accordingly, it is considered with respect to ICG-bound PMPC that ICG and protein in blood are brought into stochastic contact with each other and recognized as foreign substances, and carried to the liver or the spleen to result in a reduction in concentration in blood. An accumulation in a tumor is considered to be made by the EPR effect, and the accumulation in a tumor is rapidly made. In addition, phosphorylcholine is the material of a cell membrane, and therefore the polymer according to the present embodiment, having phosphorylcholine (derivative) as a side chain, is considered to be incorporated at the time of formation of the cell membrane during tumor proliferation and accumulated in a tumor.

It is consequently considered that the polymer according to the present embodiment has a high tumor/blood ratio.

In the present embodiment, it has been found that not only the stealth effect (non-protein-binding property) and the molecular weight of the hydrophilic polymer, but also the interaction between the polymer and the near-infrared dye is important for the tumor accumulation property and the concentration in blood (retentivity in blood), and both enhancements in the tumor accumulation property and the tumor/blood ratio that have been difficult to achieve in the prior art can be achieved.

(Main Chain)

Examples of the main chain of the polymer of the present embodiment, namely, A in the formula (P2) include a main chain represented by any of the following formulae (m1) to (m3).

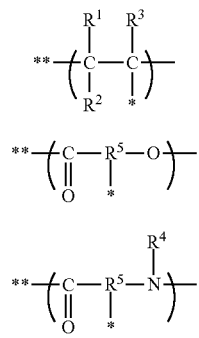

In the formulae (m1) to (m3), $R^1$ to $R^4$ each independently represent a hydrogen atom, or a substituted or unsubstituted hydrocarbon group having 1 or more and 4 or less carbon atoms; $R^5$ represents a substituted or unsubstituted hydrocarbon group having 1 or more and 9 or less carbon atoms, in which when $R^5$ represents a hydrocarbon group having 2 or more carbon atoms, any carbon may be bound to -L2-B or B as a side chain; and each substituent in $R^1$ to $R^5$ is a functional group including at least one selected from the group consisting of a halogen atom, an oxygen atom and a nitrogen atom. In the formulae (m1) to (m3), * represents binding to L2 or B, ** represents binding to L1 or D, and each terminal not marked represents binding to E.

The main chain of the polymer of the present embodiment includes, in addition to the main chains of the formulae (m1) to (m3), polyurethane and polycarbonate.

The main chain A according to the present embodiment can be a main chain represented by the following formula (m1-1).

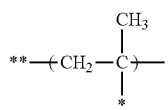

In the formula (m1-1), * represents binding to L2 or B, ** represents binding to L1 or D, and the terminal not marked represents binding to E.

(Side Chain)

Examples of the side chain of the polymer according to the present embodiment, namely, B in the formula (P2) include a phosphorylcholine structure represented by the following formula (s1-1).

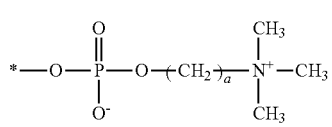

In the formula (s1-1), a represents an integer of 1 or more and 4 or less, and * represents binding to A or L2.

Specific examples of L2-B in the formula (P2) including the formula (s1-1) include a structure represented by the following formula (s1-2).

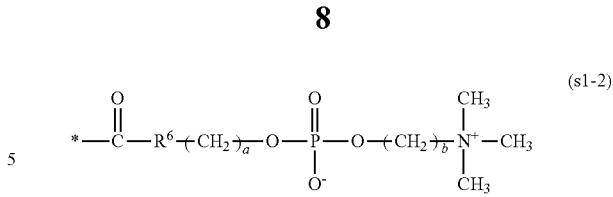

In the formula (s1-2), a and b each independently represent an integer of 1 or more and 4 or less, $R^6$ represents any of an oxygen atom or an NH group, and * represents binding to A.

One embodiment according to the present embodiment includes a polymer in which

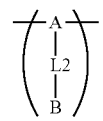

in the formula (P2) includes a structure represented by the following formula (p1-1).

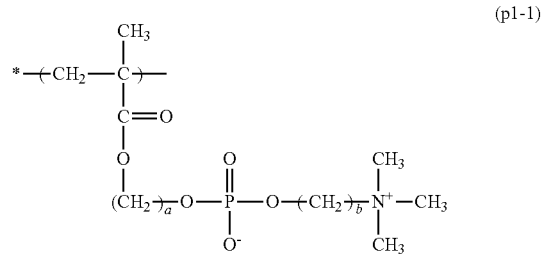

In the formula (p1-1), a and b each independently represent an integer of 1 or more and 4 or less, * represents binding to L1 or D, and the terminal not marked represents binding to E.

Examples of the phosphorylcholine-containing polymer according to the present embodiment include a polymer (the following formula (p1-2)) in which a and b in the formula (p1-1) each represent 2. The polymer represented by the formula (p1-2) is a polymer including a poly(2-methacryloyloxyethyl phosphorylcholine) (sometimes abbreviated as PMPC) backbone. That is, examples thereof include a polymer in which

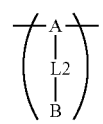

in the formula (P2) is represented by the following formula (p1-2).

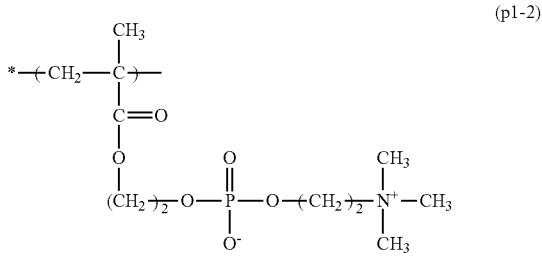

In the formula (p1-2), * represents binding to L1 or D and the terminal not marked represents binding to E.

(Near-infrared Dye)

The near-infrared dye in the present embodiment is not particularly limited as long as the near-infrared dye absorbs light in the near-infrared wavelength region to emit an acoustic wave. The near-infrared wavelength region here means the range of 600 nm or more and 1300 nm or less.

Examples of the near-infrared dye in the present embodiment can include an azine type dye, an acridine type dye, a triphenylmethane type dye, a xanthene type dye, a porphyrin type dye, a cyanine type dye, a phthalocyanine type dye, a styryl type dye, a pyrylium type dye, an azo type dye, a quinone type dye, a tetracycline type dye, a flavone type dye, a polyene type dye, a BODIPY (registered trademark) type dye and an indigoid type dye.

Examples of the cyanine type dye can include indocyanine green (ICG), an Alexa Fluor (registered trademark) type dye such as Alexa 750 (produced by Invitrogen Corporation), a Cy (registered trademark) type dye (produced by GE Healthcare Biosciences K.K.), IR-783, IR-806 and IR-820 (produced by Sigma-Aldrich Japan K.K.), IR Dye 800CW and IR Dye 800RS (registered trademark) (produced by LI-COR, Inc.), ADS780WS, ADS795WS, ADS830WS and ADS832WS (produced by American Dye Source Inc.), Sulfo-Cyanine7 (produced by Lumiprobe GmbH), and IR Dye700DX (registered trademark) (produced by LI-COR, Inc.).

That is, in the present embodiment, the dye backbone D in the formula (P2) can be particularly represented by the following formula (d1) or (d2).

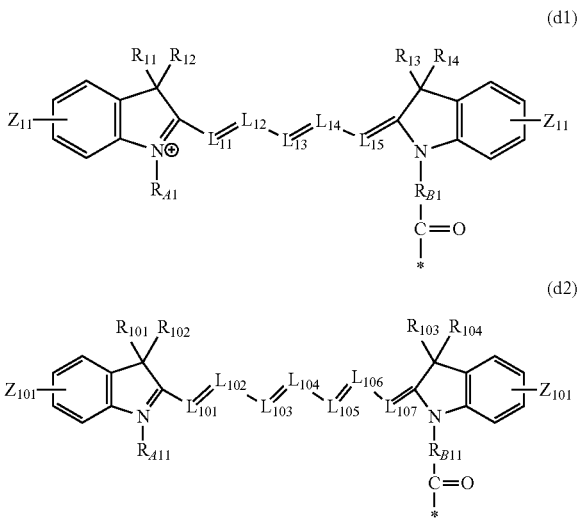

In the formula (d1), $L_{11}$, $L_{12}$, $L_{13}$, $L_{14}$ and $L_{15}$ may be each the same or different, and represent CH or $CR_{15}$, and $R_{15}$ represents a straight or branched alkyl group having 1 to 10 carbon atoms. $L_{11}$, $L_{12}$, $L_{13}$, $L_{14}$ and $L_{15}$ may be taken together to form a 4-membered ring to a 6-membered ring. $R_{11}$, $R_{12}$, $R_{13}$ and $R_{14}$ may be each the same or different, and represent a hydrogen atom, a straight or branched alkyl group having 1 to 10 carbon atoms, $-R_{D1}-SO_3^-$, or $-R_{E1}-SO_3X_{11}$. $R_{D1}$ and $R_{E1}$ represent a straight or branched alkylene group having 1 to 10 carbon atoms. $X_{11}$ represents any of a hydrogen atom, a sodium atom, a potassium atom, or a cation derived from ammonium, triethylammonium, lysine or arginine. $R_{A1}$ represents a straight or branched alkyl group having 1 to 10 carbon atoms, $-R_{C1}-SO_3^-$, $-R_{G1}-SO_3X_{15}$, or $-R_{F1}-CO_2X_{14}$. $X_{14}$ and $X_{15}$ represent any of a hydrogen atom, a sodium atom, a potassium atom, or a cation derived from ammonium, triethylammonium, lysine or arginine. $R_{C1}$, $R_{F1}$ and $R_{G1}$ represent a straight or branched alkylene group having 1 to 10 carbon atoms. When $R_{A1}$ represents a straight or branched alkyl group having 1 to 10 carbon atoms, a halogen ion or an organic acid ion may be included as a counter ion. $R_{B1}$ represents a straight or branched alkylene group having 1 to 10 carbon atoms. $Z_{11}$ represents a hydrogen atom or $-SO_3X_{12}$, or is taken together with an indole ring bound to $Z_{11}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms, or $-SO_3X_{13}$. $X_{12}$ and $X_{13}$ represent any of a hydrogen atom, a sodium atom, a potassium atom, or a cation derived from ammonium, triethylammonium, lysine or arginine, and * represents binding to L1, or represents binding to the carbon atom at the terminal of the repeating unit in the formula (P2) when the polymer does not include L1. In the formula (d2), $L_{101}$, $L_{102}$, $L_{103}$, $L_{104}$, $L_{105}$, $L_{106}$ and $L_{107}$ may be each the same or different, and represent CH or $CR_{105}$, and $R_{105}$ represents a straight or branched alkyl group having 1 to 10 carbon atoms. $L_{101}$, $L_{102}$, $L_{103}$, $L_{104}$, $L_{105}$, $L_{106}$ and $L_{107}$ may be taken together to form a 4-membered ring to a 6-membered ring. $R_{101}$, $R_{102}$, $R_{103}$ and $R_{104}$ may be each the same or different, and represent a hydrogen atom, a straight or branched alkyl group having 1 to 10 carbon atoms, $-R_{D11}-SO_3^-$, or $-R_{E11}-SO_3X_{101}$. $R_{D11}$ and $R_{E11}$ represent a straight or branched alkylene group having 1 to 10 carbon atoms. $X_{101}$ represents any of a hydrogen atom, a sodium atom, a potassium atom, or a cation derived from ammonium, triethylammonium, lysine or arginine. $R_{A11}$ represents a straight or branched alkyl group having 1 to 10 carbon atoms, $-R_{C11}-SO_3^-$, $-R_{G11}-SO_3X_{105}$, or $-R_{F1}-CO_2X_{104}$. $X_{104}$ and $X_{105}$ represent any of a hydrogen atom, a sodium atom, a potassium atom, or a cation derived from ammonium, triethylammonium, lysine or arginine. $R_{C11}$, $R_{F11}$ and $R_{G11}$ represent a straight or branched alkylene group having 1 to 10 carbon atoms. When $R_{A11}$ represents a straight or branched alkyl group having 1 to 10 carbon atoms, a halogen ion or an organic acid ion may be included as a counter ion. The dye backbone D may be bound to the carbon atom at the terminal of the repeating unit in the formula (P2) or the linker L1 via $R_{A11}$. $R_{B11}$ represents a straight or branched alkylene group having 1 to 10 carbon atoms. $Z_{101}$ represents a hydrogen atom or $-SO_3X_{102}$, or is taken together with an indole ring bound to $Z_{101}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms, or $-SO_3X_{103}$. $X_{102}$ and $X_{103}$ represent any of a hydrogen atom, a sodium atom, a potassium atom, or a cation derived from ammonium, triethylammonium, lysine or arginine, and * represents binding to L1, or represents binding to the carbon atom at the terminal of the repeating unit in the formula (P2) when the polymer does not include L1.

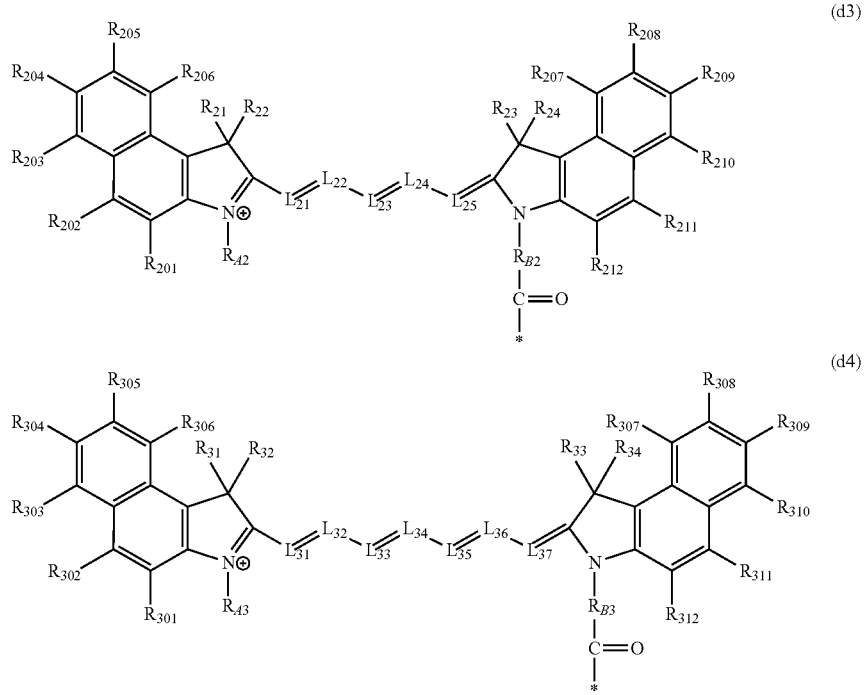

Furthermore, the formulae (d1) and (d2) can also be represented by the formulae (d3) and (d4), respectively.

In the formula (d3), $R_{201}$ to $R_{212}$ may be each the same or different, and represent a hydrogen atom, a straight or branched alkyl group having 1 to 10 carbon atoms, or $-SO_3X_{24}$. $X_{24}$ represents any of a hydrogen atom, a sodium atom, a potassium atom, or a cation derived from ammonium, triethylammonium, lysine or arginine. $L_{21}$, $L_{22}$, $L_{23}$, $L_{24}$ and $L_{25}$ may be each the same or different, and represent CH or $CR_{25}$, and $R_{25}$ represents a straight or branched alkyl group having 1 to 10 carbon atoms. $L_{21}$, $L_{22}$, $L_{23}$, $L_{24}$ and $L_{25}$ may be taken together to form a 4-membered ring to a 6-membered ring. $R_{21}$, $R_{22}$, $R_{23}$ and $R_{24}$ may be each the same or different, and represent a hydrogen atom, a straight or branched alkyl group having 1 to 10 carbon atoms, $-R_{D2}-SO_3^-$, or $-R_{E2}-SO_3X_{21}$. $R_{D2}$ and $R_{E2}$ represent a straight or branched alkylene group having 1 to 10 carbon atoms. $X_{21}$ represents any of a hydrogen atom, a sodium atom, a potassium atom, or a cation derived from ammonium, triethylammonium, lysine or arginine. $R_{42}$ represents a straight or branched alkyl group having 1 to 10 carbon atoms, $-R_{C2}-SO_3^-$, $-R_{G2}-SO_3X_{25}$, or $-R_{F2}-CO_2X_{24}$. $X_{24}$ and $X_{25}$ represent any of a hydrogen atom, a sodium atom, a potassium atom, or a cation derived from ammonium, triethylammonium, lysine or arginine. $R_{C2}$, $R_{F2}$ and $R_{G2}$ represent a straight or branched alkylene group having 1 to 10 carbon atoms. When $R_{42}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. The dye backbone D may be bound to the carbon atom at the terminal of the repeating unit in the formula (P2) or the linker L1 via $R_{42}$. $R_{B2}$ represents a straight or branched alkylene group having 1 to 10 carbon atoms. * represents binding to L1, or represents binding to the carbon atom at the terminal of the repeating unit in the formula (P2) when the polymer does not include L1.

In the formula (d4), $R_{301}$ to $R_{312}$ may be each the same or different, and represent a hydrogen atom, a straight or branched alkyl group having 1 to 10 carbon atoms, or $-SO_3X_{34}$. $X_{34}$ represents any of a hydrogen atom, a sodium atom, a potassium atom, or a cation derived from ammonium, triethylammonium, lysine or arginine. $L_{31}$, $L_{32}$, $L_{33}$, $L_{34}$, $L_{35}$, $L_{36}$ and $L_{37}$ may be each the same or different, and represent CH or $CR_{35}$, and $R_{35}$ represents a straight or branched alkyl group having 1 to 10 carbon atoms. $L_{31}$, $L_{32}$, $L_{33}$, $L_{34}$, $L_{35}$, $L_{36}$ and $L_{37}$ may be taken together to form a 4-membered ring to a 6-membered ring. $R_{31}$, $R_{32}$, $R_{33}$ and $R_{34}$ may be each the same or different, and represent a hydrogen atom, a straight or branched alkyl group having 1 to 10 carbon atoms, $-R_{D3}-SO_3^-$, or $-R_{E3}-SO_3X_{31}$. $R_{D3}$ and $R_{E3}$ represent a straight or branched alkylene group having 1 to 10 carbon atoms. $X_{31}$ represents any of a hydrogen atom, a sodium atom, a potassium atom, or a cation derived from ammonium, triethylammonium, lysine or arginine. $R_{43}$ represents a straight or branched alkyl group having 1 to 10 carbon atoms, $-R_{C3}-SO_3^-$, $-R_{G3}-SO_3X_{35}$, or $-R_{F3}-CO_2X_{34}$. $X_{34}$ and $X_{35}$ represent any of a hydrogen atom, a sodium atom, a potassium atom, or a cation derived from ammonium, triethylammonium, lysine or arginine. $R_{C3}$, $R_{F3}$ and $R_{G3}$ represent a straight or branched alkylene group having 1 to 10 carbon atoms. When $R_{43}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. The dye backbone D may be bound to the carbon atom at the terminal of the repeating unit in the formula (P2) or the linker L1 via $R_{43}$. $R_{B3}$ represents a straight or branched alkylene group having 1 to 10 carbon atoms. * represents binding to L1, or represents binding to the carbon atom at the terminal of the repeating unit in the formula (P2) when the polymer does not include L1.

In the present embodiment, specific examples of the formulae (d1) to (d4) include the following formulae (d1-1) to (d1-6).

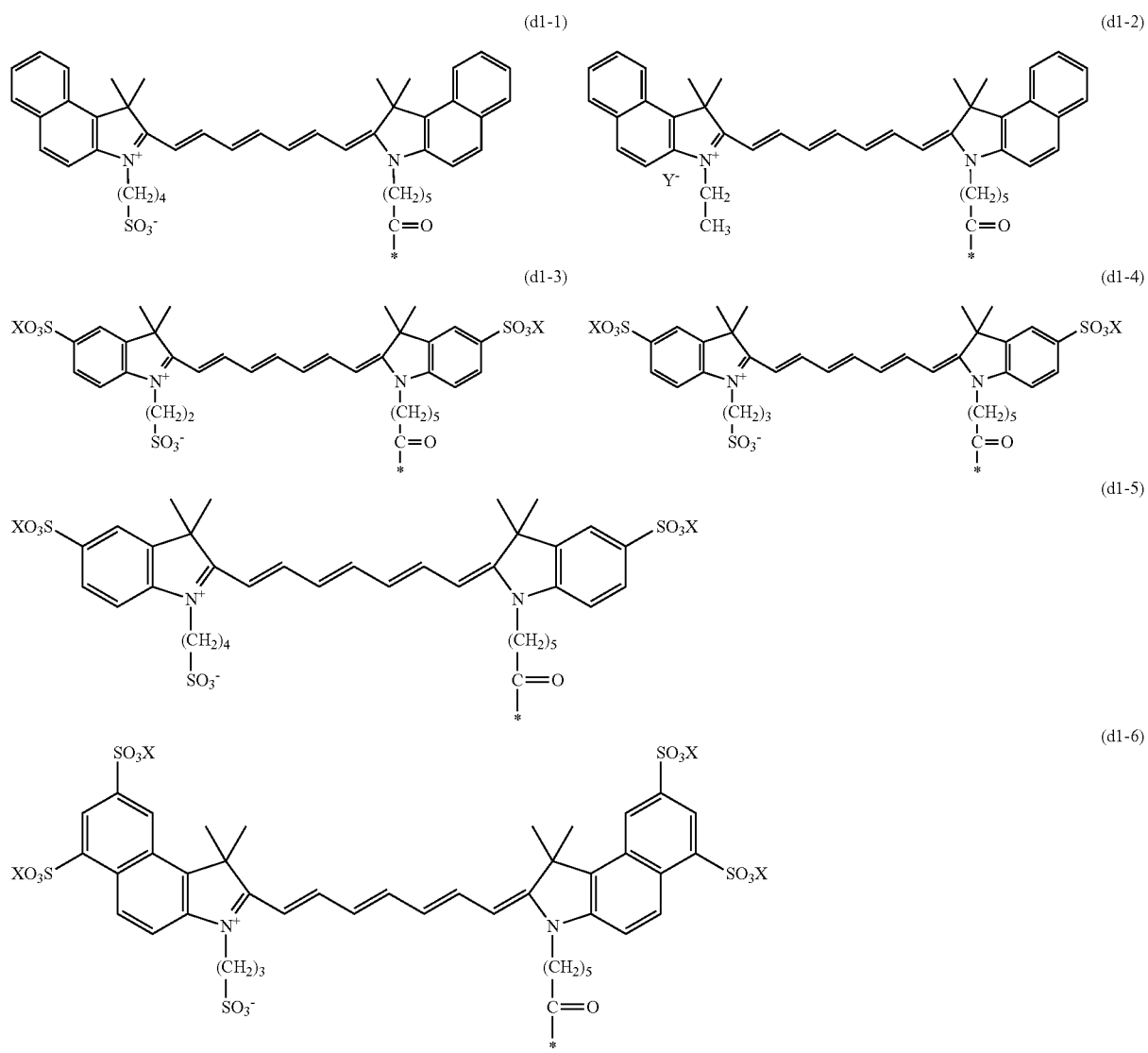

In the formulae (d1-1) to (d1-6), * represents binding to L1 or A, and X represents any of sodium, potassium, ammonium, triethylammonium, lysine and arginine.

In the formula (d1-2), Y⁻ represents any of a halogen ion such as a chloride ion, a bromide ion or an iodide ion, or an organic acid ion such as an acetate ion, a tartrate ion or a succinate ion.

One example of the dye backbone D includes near-infrared dyes represented by the following formulae (d2-1) to (d2-7).

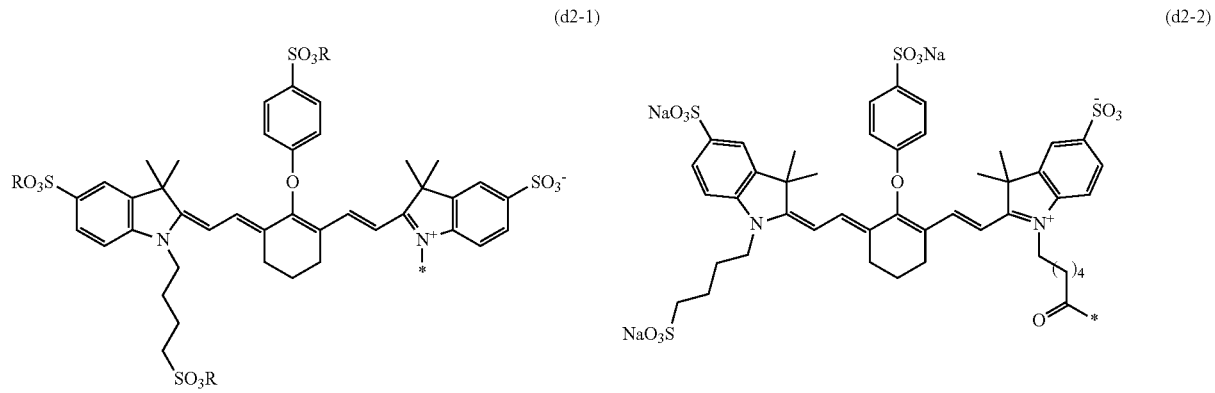

-continued (d2-3)
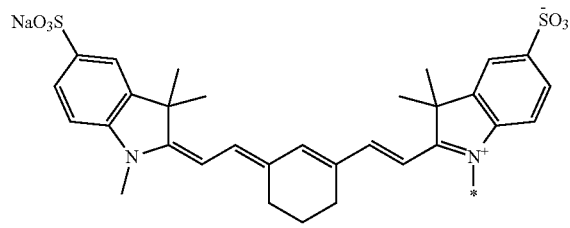

(d2-4)
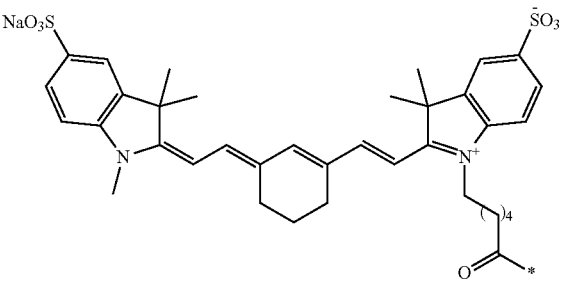

(d2-5)
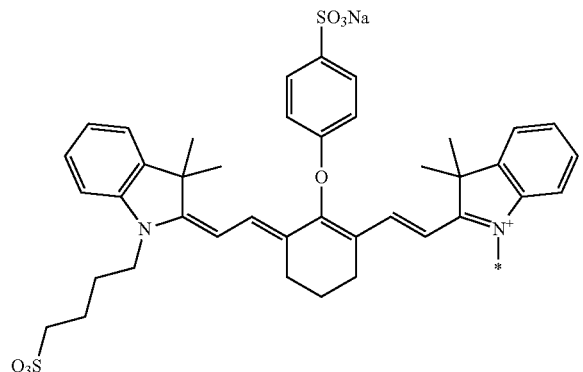

(d2-6)
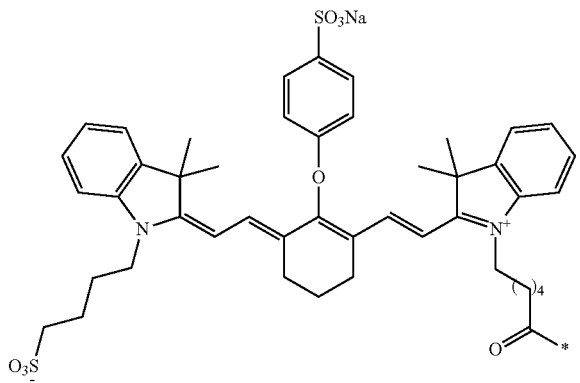

(d2-7)
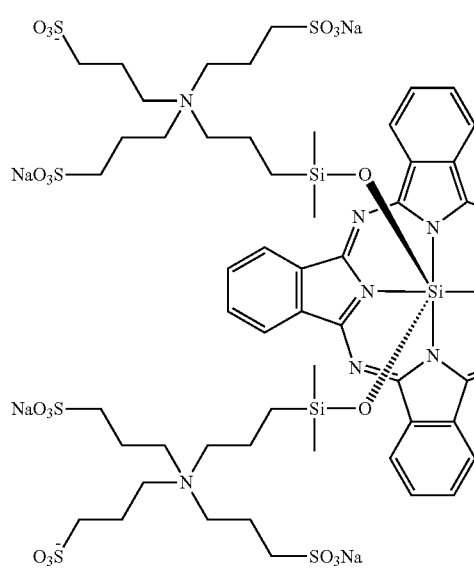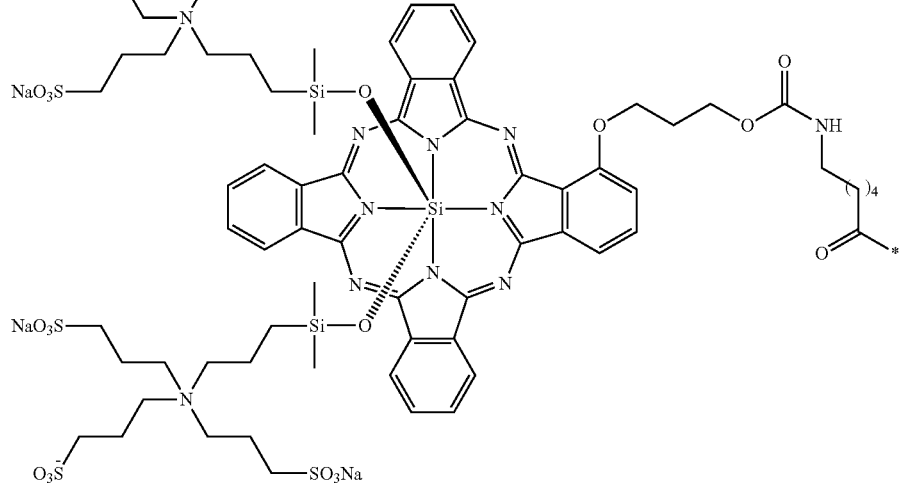

In the formulae (d2-1) to (d2-7), * represents binding to L1 or A. R represents a cation derived from any of sodium, potassium, ammonium, triethylammonium, lysine and arginine.

(Linker Moiety)

In the formula (P2), L1 and L2 represent a linker. In the present embodiment, L1 as a linker moiety is a linker that covalently binds the main chain A and the dye backbone, and L2 as a linker moiety is a linker that covalently binds the main chain A and the side chain B.

Examples of a part of each of L1 and L2 include one represented by any of the following formulae (l1) to (l21). In the following formulae (l1) to (l21), * represents binding to other atom.

(l1)
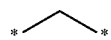

(l2)

(l3)

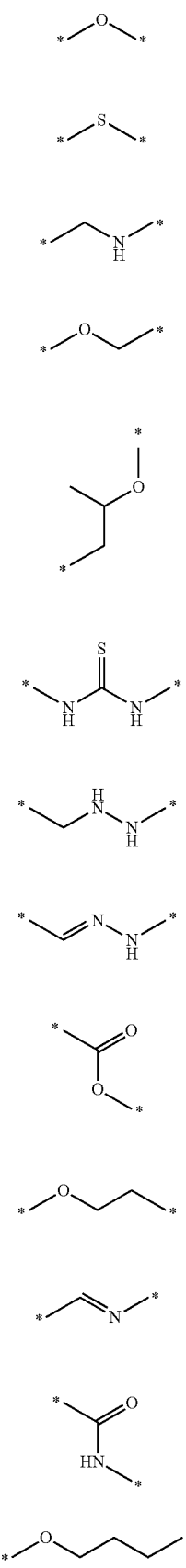
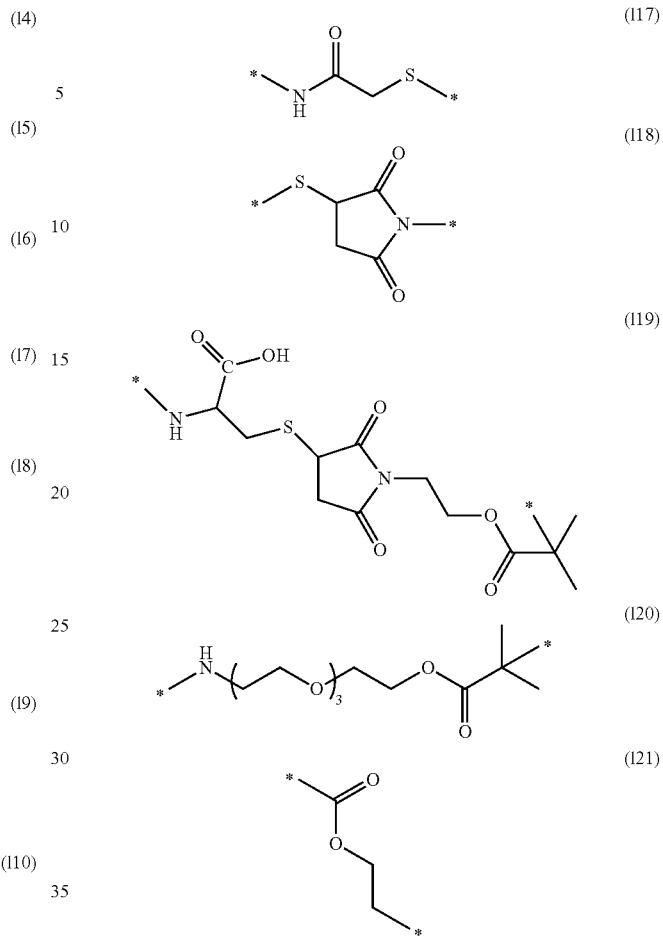

Among the above chemical structures, an asymmetric structure may have any direction, and may have a reverse arrangement to any of the above-exemplified chemical structures.

Formation of L1 and L2 above can be conducted by using, for D, A or B above, one having a reactive group such as an amino group, a hydroxyl group, a thiol group, a carboxyl group, an epoxy group, a glycidyl group, an N-succinimidyloxy group, an N-sulfosuccinimidyl group, an N-maleimide alkyl group, an iodoacetamide group, a bromoacetamide group, an isothiocyano group, a sulfonic acid chloride group and a carboxylic acid chloride group, to generate a bond between the above reactive groups selected as a combination that allows a binding reaction to occur. When the bond generated above includes a Schiff base and a carbonyl group, such base and group can be subjected to reduction to achieve further stabilization of the bond.

D, A or B above may be directly bound to the reactive group, or may be bound via one or more atoms.

Specifically, D, A or B above may be bound via one or more methylenes.

L1 can be located at the terminal of the phosphorylcholine-containing polymer.

(Terminal)

In the formula (p2), E represents the terminal and is not particularly limited. Examples of E include a functional group.

The functional group as E in the polymer according to the present embodiment includes any groups, and one example thereof can include halogen, an alkyl group, a hydroxyl group, a carboxyl group, an amino group, a thiol group, an azido group, a diamine, a succinimidyl ester group, a maleimide group and a succinimide group. Examples of halogen are bromine and chlorine. Examples of a compound as E can include a low-molecular compound, a reporter molecule, a target-binding molecule and other polymer. Examples of the low-molecular compound include an inhibitor such as gefitinib. Examples of the reporter molecule include a molecule generating a physical signal such as a radioactive signal, a magnetic field signal, an ultrasonic signal, a fluorescent signal or an optical ultrasonic signal, and radioactive halogen, radioisotope, a paramagnetic metal ion, an iron oxide particle, a gold nanoparticle, a microbubble, a dye and an anticancer agent that are therapeutic agents. Examples of the dye include a fluorescent compound, a phosphorescent compound and a near-infrared absorbing compound. Examples of the target-binding molecule include artificial antibodies such as an antibody, an antibody fragment and a single-strand antibody, and an enzyme, bioactive peptide, glycopeptide, a sugar chain, a lipid and a molecule-recognizing compound. Examples of other polymer as E include polyethylene glycol, and such a polymer may have any degree of polymerization and may also be ethylene glycol.

(Examples of Polymer)

Examples of the polymer according to the present embodiment include polymers represented by the following formulae (1) to (7).

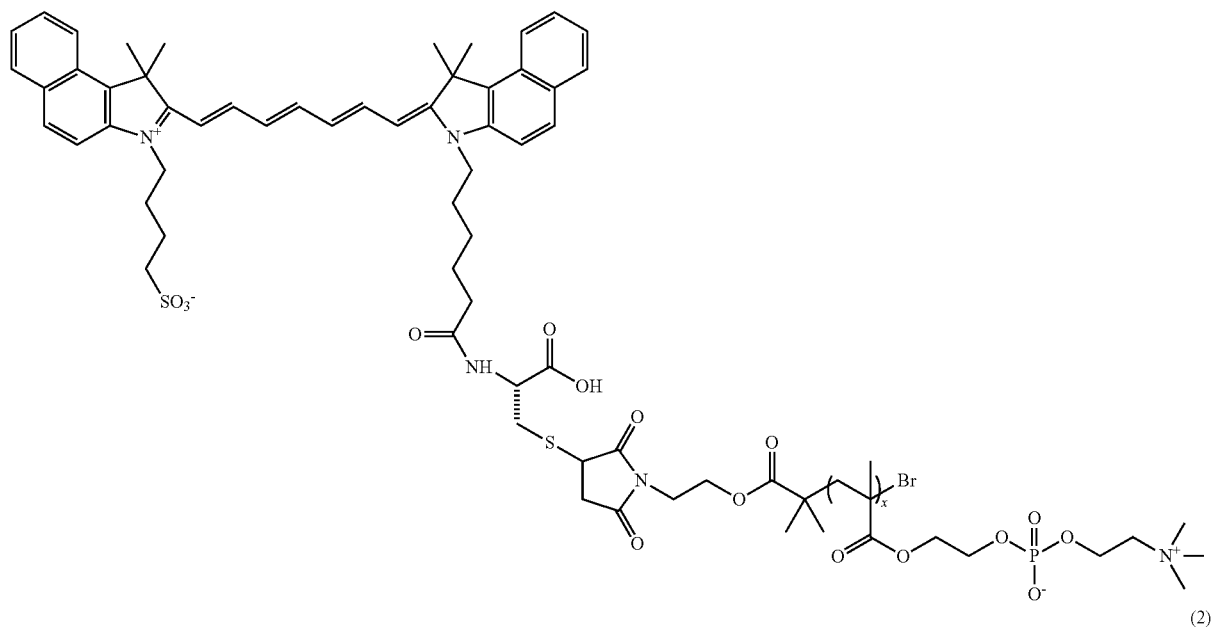

(1)

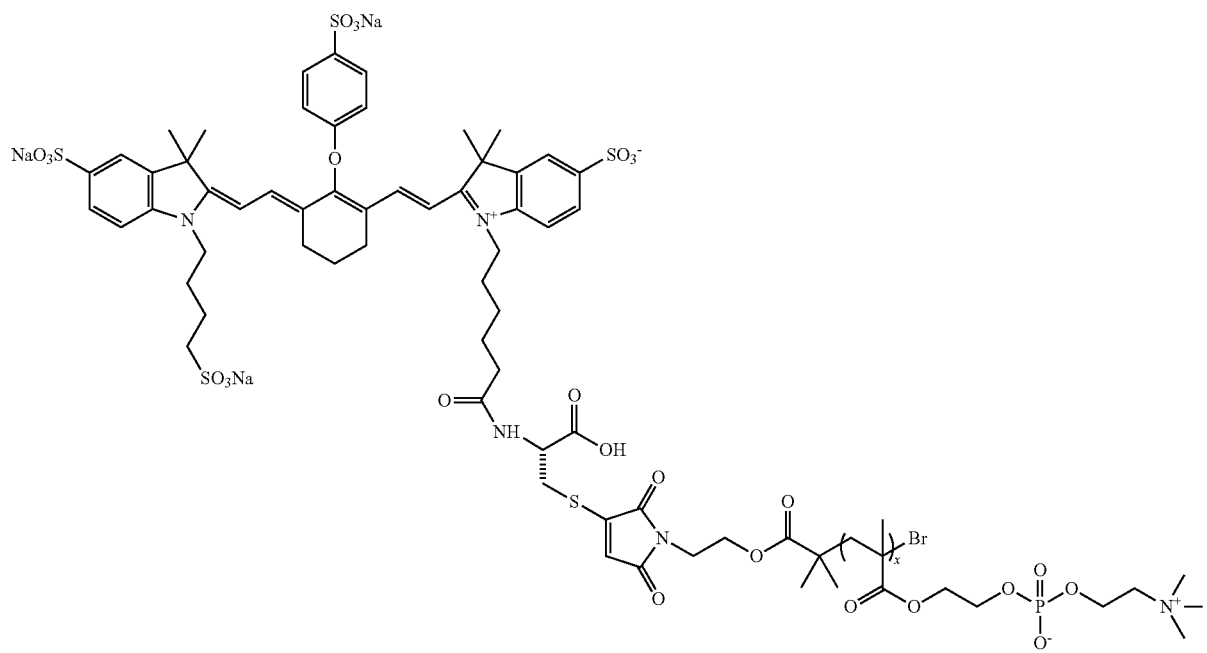

(2)

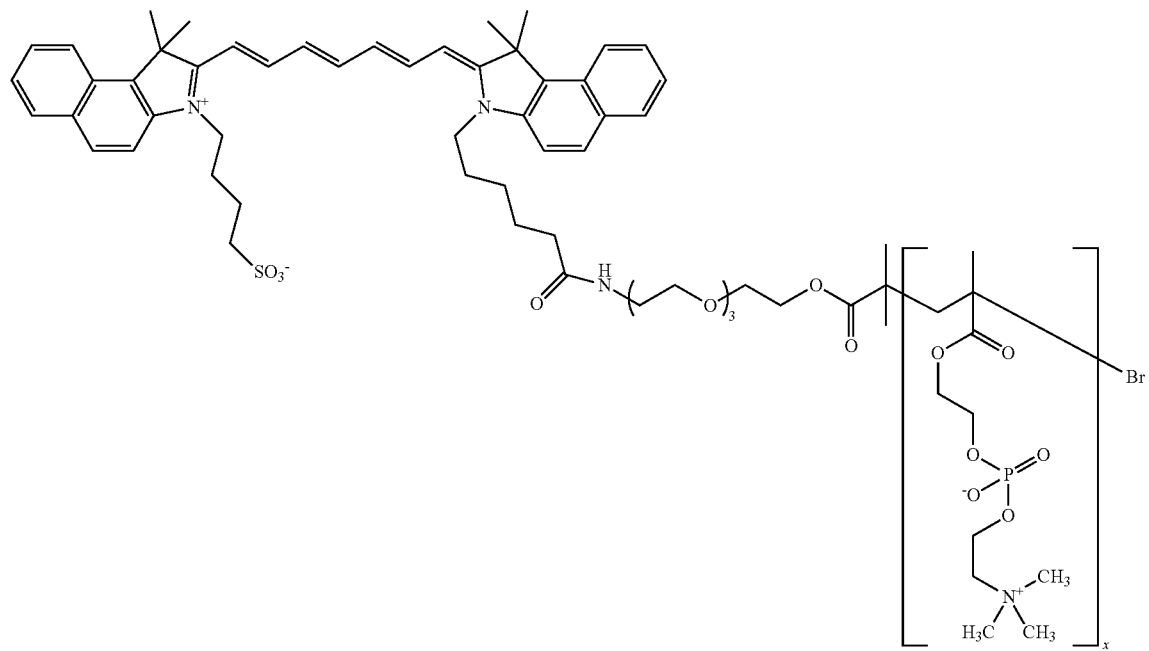
(3)
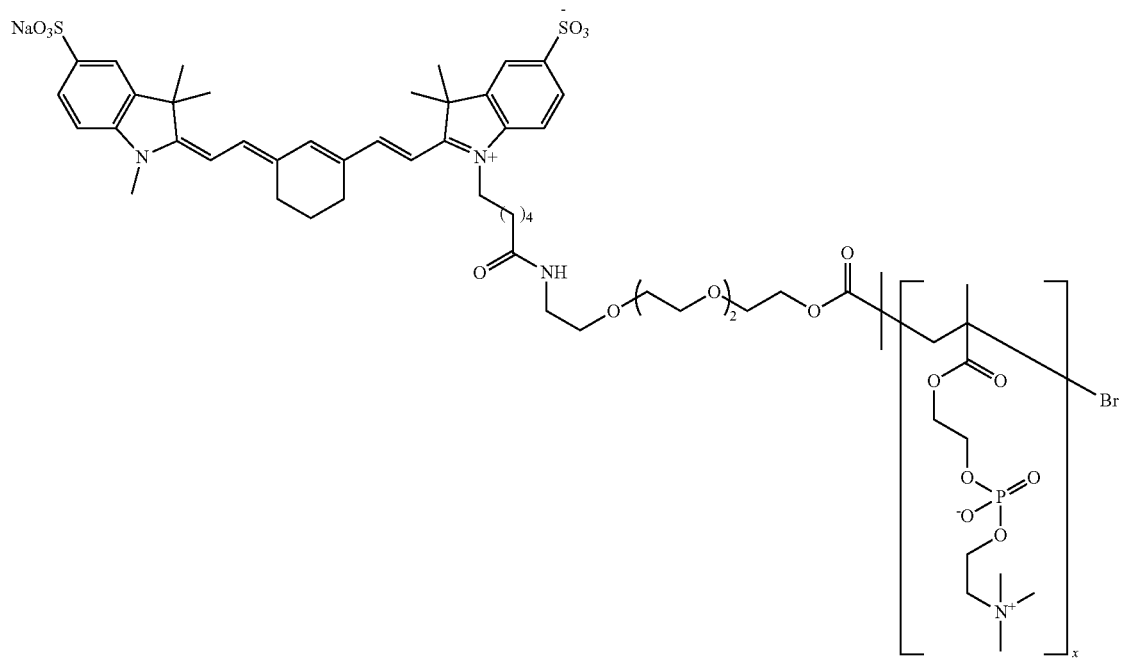
(4)

-continued
(5)
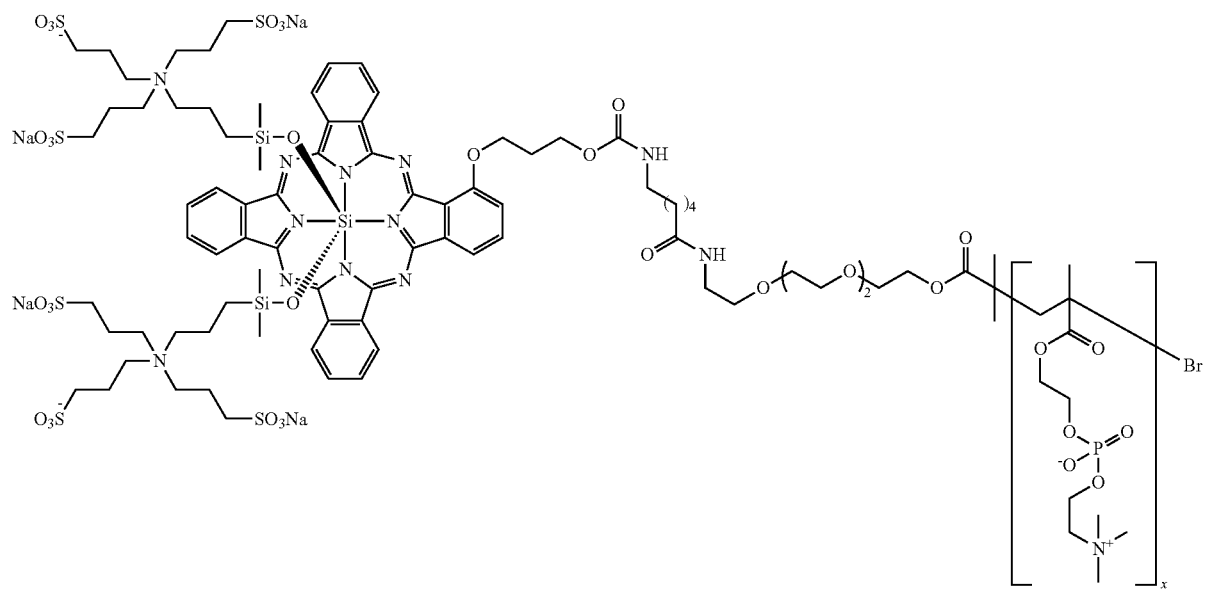
(6)
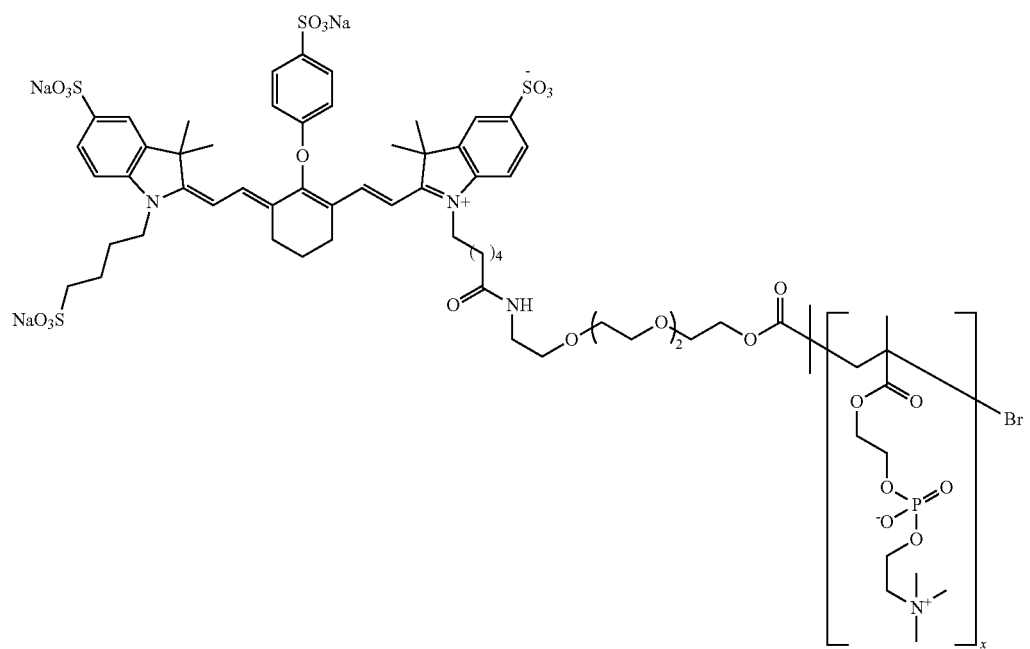

-continued (7)

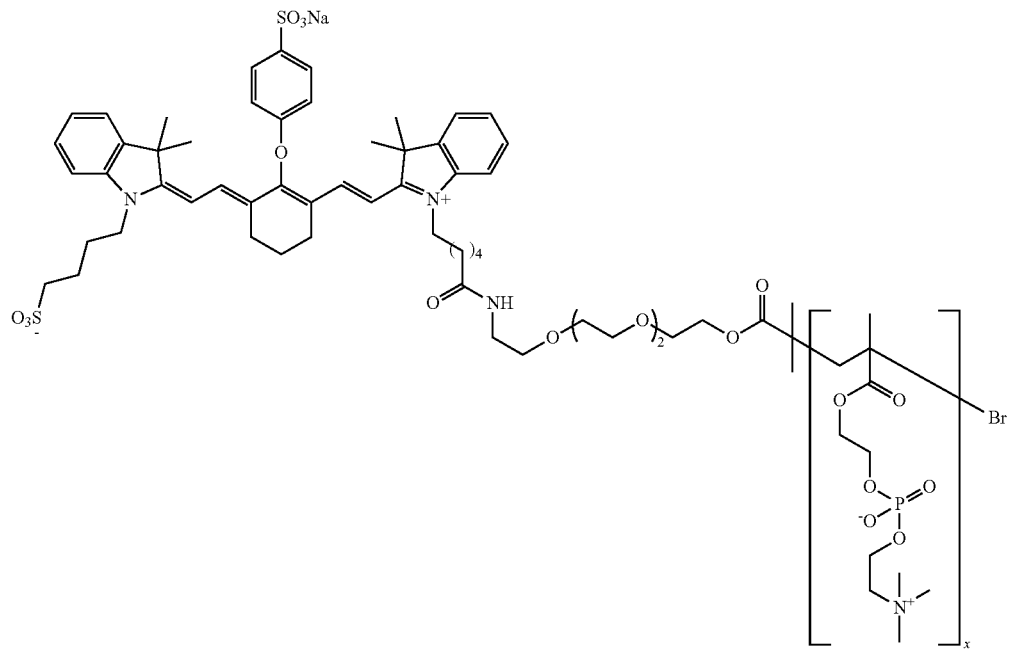

In the formulae (1) to (7), each x represents an integer of 1 or more.

(Molecular Weight (Degree of Polymerization))

In the present description, the molecular weight means the number average molecular weight. The number average molecular weight can be measured by the proton NMR method or the GPC method.

Hereinafter, the number average molecular weight may be simply designated as "molecular weight". In addition, any molecular weight range below can be the molecular weight range measured by the proton NMR method.

The molecular weight of the polymer according to the present embodiment is preferably 5000 or more and 100000 or less. The reason is because, when the polymer has a molecular weight of more than 100000, the administration liquid thereof has a high viscosity to sometimes put a burden on a living body in administration thereof to the living body. In addition, when the molecular weight is 5000 or less, the size may be small and rapid renal excretion may reduce the retentivity in blood to result in deterioration in tumor accumulation property.

The molecular weight of the polymer according to the present embodiment is preferably 9000 or more and 50000 or less. As shown in the present embodiment, the reason is because PMPC having a molecular weight of 9000 or more allows a high accumulation in a tumor to be observed. Furthermore, as the molecular weight of PMPC is increased, selectivity of tumor accumulation is increased. For example, ICG-PMPC having as a backbone PMPC having a molecular weight of 50000 exhibits a higher tumor selectivity than one having PMPC having a molecular weight of 10000 to 40000. That is, a compound having a molecular weight of 50000 is particularly preferable in terms of tumor selectivity because the compound exhibits a low accumulation in a normal tissue, but exhibits a high accumulation in a tumor. In terms of the tumor/blood ratio, the molecular weight is particularly preferably 16000 or more and 20000 or less. The reason is because the tumor accumulation property is high while the concentration in blood is relatively low.

The polymer according to the present embodiment has a degree of polymerization of preferably 10 or more, further preferably 30 or more. A degree of polymerization of 30 or more is advantageous because the molecular weight of the polymer reaches about 10000 and the tumor accumulation property by the EPR effect is easily exhibited.

The degree of polymerization of the polymer according to the present embodiment can be 350 or less. When the degree of polymerization is 350 or less, a sufficiently low viscosity is achieved and the polymer according to the present embodiment can be administered into a living body. Accordingly, the degree of polymerization of the polymer according to the present embodiment can be 30 or more and 350 or less.

(Monomer)

2-Methacryloyloxyethyl phosphorylcholine (sometimes abbreviated as "MPC") that is one example of a monomer for synthesizing the polymer according to the present embodiment can be synthesized according to, for example, the following reaction formula 1.

Reaction formula 1

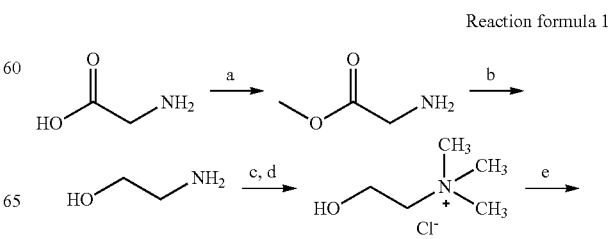

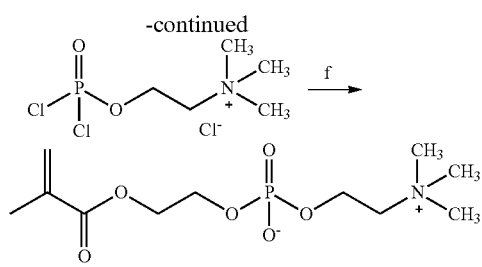

Reagents and conditions: a) AcCl, MeOH, reflux, 1 h, quant.; b) LaH, THF, 5 h; c) CH₃I, K₂CO₃, 12 h; d) Ag₂O, MeOH, 15 min, then HCl aq, 27% in two steps; e) POCl₃, CH₃CN, 24 h; f) 2-hydroxyethyl methacrylate, CH₃CN With respect to polymerization of the monomer, a conventionally known polymerization method can be appropriately selected depending on the type of the monomer. For example, when the monomer is a vinyl monomer, the polymerization method can include the living radical polymerization method, inter alia, the atom transfer radical polymerization (ATRP) method. The ATRP method can be adopted because of being simple and easily controlling the molecular weight. When the monomer is an ester or an amide, the polymerization method can include condensation polymerization. In condensation polymerization, a condensing agent may also be appropriately used. When the monomer is lactide, lactone or lactam, the polymerization method can include ring-opening polymerization. In ring-opening polymerization, a catalyst may also be appropriately used.

(Atom Transfer Radical Polymerization)

The ATRP method is a method in which a vinyl monomer is polymerized by using a polymerization initiator having a high reactive carbon-halogen bond, and a transition metal complex as a polymerization catalyst.

The PMPC backbone of a polymer as one example of the phosphorylcholine-containing polymer according to the present invention can be obtained by atom transfer radical polymerization as shown in the following reaction formula 2.

When the vinyl monomer is subjected to atom transfer radical polymerization, for example, any polymerization initiator represented by the following formulae (i1) to (i12) can be used.

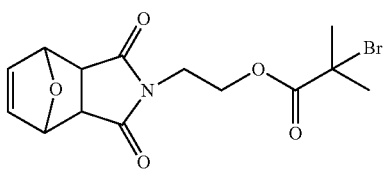
(i1)

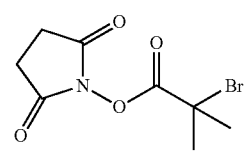
(i2)

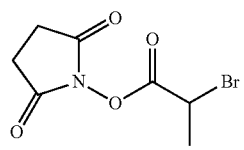
(i3)

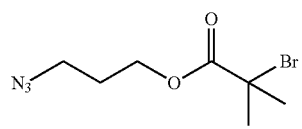
(i4)

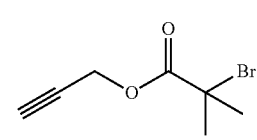
(i5)

Reaction formula 2

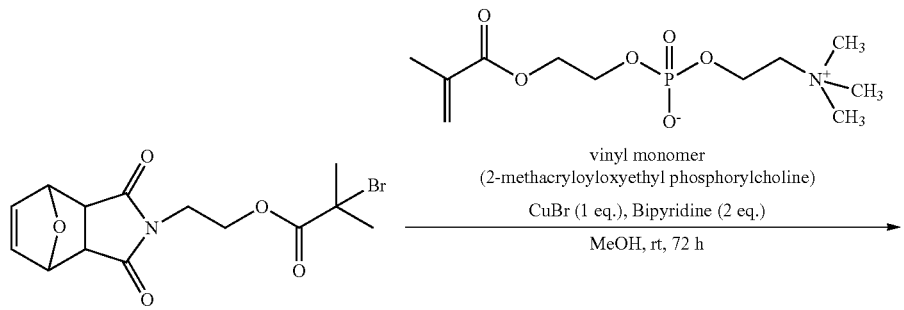

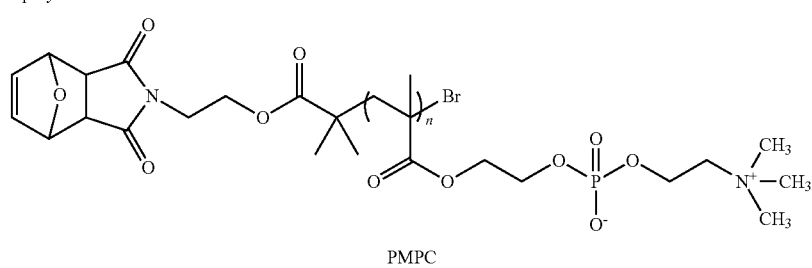

-continued

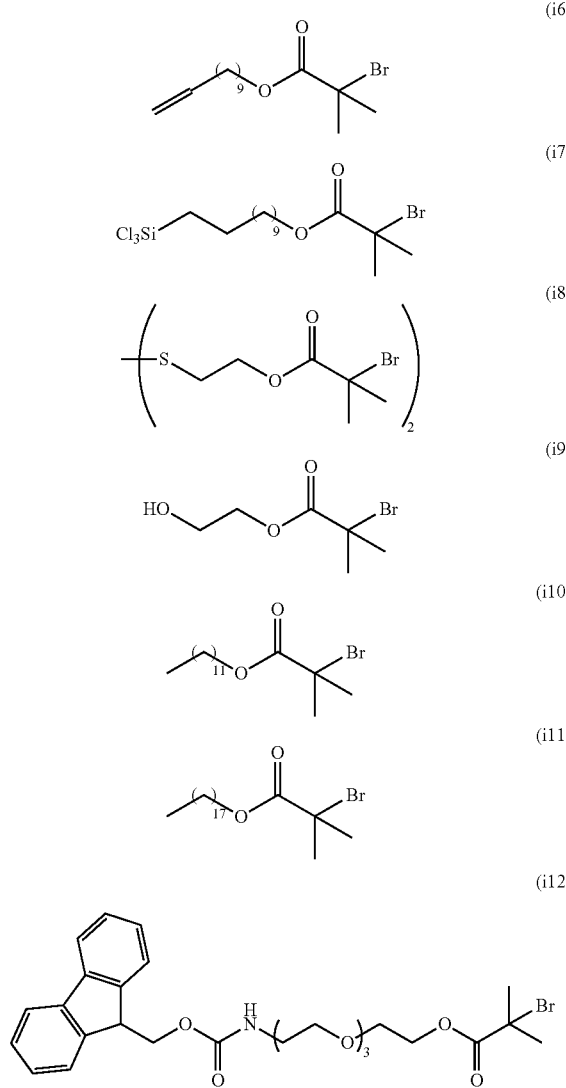

Such a polymerization initiator may also include various functional groups. For example, when the initiator of any of the formulae (i1) to (i3) is used, a maleimide group or an N-hydroxysuccinimide group protected can be introduced to the terminal of the polymer. When the initiator of the formula (i12) is used, an amino group protected can be introduced to the terminal of the polymer. The near-infrared dye is bound via such a functional group, thereby providing the polymer according to the present embodiment.

Under an inert gas, the polymerization initiator and the transition metal complex are added into a reaction solvent including the vinyl monomer, and atom transfer radical polymerization is conducted. The polymerization can progress in a living manner to provide a polymer having a narrow molecular weight distribution.

The reaction solvent is not particularly limited, and for example, water, methanol, ethanol, dimethylsulfoxide, dimethylformamide or acetonitrile can be used. Such solvents can be used singly or in combinations of two or more. For the inert gas, a nitrogen gas or an argon gas can be used.

The transition metal complex to be used includes a metal halide and a ligand. The metal of the metal halide preferably includes transition metals from Ti with an atomic number of 22 to Zn with an atomic number of 30, particularly preferably includes Fe, Co, Ni and Cu. In particular, cuprous chloride or cuprous bromide can be adopted.

The ligand is not particularly limited as long as the ligand can be coordinated to the metal halide, and for example, 2,2'-bipyridyl, tris(2-dimethylaminoethyl)amine, ethylenediamine, dimethylglyoxime, 1,4,8,11-tetramethyl 1,4,8,11-tetraazacyclotetradecane, 1,10-phenanthroline, N,N,N',N'',N''-pentamethyldiethylenetriamine or hexamethyl(2-aminoethyl)amine can be used.

The polymerization temperature is in the range from 0° C. to 80° C., preferably in the range from 10° C. to 60° C.

(Method for Preparing Polymer)

In the present embodiment, the method for preparing the near-infrared dye-bound phosphorylcholine-containing polymer includes binding the near-infrared dye and the phosphorylcholine-containing polymer via a linker molecule by a known coupling reaction. In one example, cysteine as the linker molecule is bound to the maleimide group at the terminal of the phosphorylcholine-containing polymer, and thereafter, a near-infrared dye having an N-sulfosuccinimidyloxy group is coupled thereto. The near-infrared dye-bound phosphorylcholine-containing polymer obtained by the coupling reaction described above can be washed and purified by a known purification method such as an ultrafiltration method or a size exclusion column chromatography method.

(Contrast Agent for Photoacoustic Imaging)

A contrast agent for photoacoustic imaging (hereinafter, sometimes abbreviated as "PAI") according to the present embodiment has the above polymer and a dispersion medium. Herein, PAI means a concept including photoacoustic tomography (tomographic method). Examples of the dispersion medium include saline, distilled water for injection, phosphate buffered saline and an aqueous glucose solution. The contrast agent for PAI according to the present embodiment may, if necessary, have a pharmacologically acceptable additive, for example, a vasodilator.

The contrast agent for PAI according to the present embodiment may be dispersed in the dispersion medium in advance, or may be in the form of a kit and may be dispersed in the dispersion medium for use before administration into a living body.

The contrast agent for PAI according to the present embodiment can be more accumulated in a tumor site than a normal site in a living body in administration to the living body by means of the EPR (Enhanced Permeability and Retention) effect. As a result, when a particle is administered to the living body and thereafter the living body is irradiated with light and an acoustic wave from the living body is detected, an acoustic wave emitted from a tumor site can be enlarged as compared to an acoustic wave emitted from a normal site. Accordingly, the contrast agent for PAI according to the present embodiment can be used for imaging a tumor.

The contrast agent for PAI according to the present embodiment can also be used for imaging a lymph node. Furthermore, the contrast agent can be particularly used for a contrast agent of a sentinel lymph node (hereinafter, sometimes abbreviated as "SLN"). The reason for this is because the contrast agent has a large size as compared with the dye by itself and therefore is more easily accumulated in the sentinel lymph node and is expected to result in an enhancement in the accumulation property.

(Photoacoustic Imaging Method)

The method for detecting the polymer according to the present embodiment, administered into a living body, by use of a PAT apparatus is described. A method for detecting the near-infrared dye-bound phosphorylcholine-containing polymer, according to the present embodiment, includes the following steps (a) and (b). Herein, the photoacoustic imaging method according to the present embodiment may also include step(s) other than the following steps:

(a) a step of irradiating a specimen, to which the near-infrared dye-bound phosphorylcholine-containing polymer according to the present embodiment is administered, with light in a wavelength region of 600 nm to 1300 nm; and (b) a step of detecting an acoustic wave emitted from the near-infrared dye-bound phosphorylcholine-containing polymer present in the specimen.

The method for detecting the near-infrared dye-bound phosphorylcholine-containing polymer according to the present embodiment may include a step of reconstructing a spatial photoacoustic signal intensity distribution from the wavelength, phase, time information and the like of the acoustic wave obtained in step (b) above. Herein, three-dimensional image reconstruction can be conducted based on the wavelength, phase and time information of the photoacoustic signal obtained in step (b) above. Data obtained by the image reconstruction may take any form as long as the position information of the intensity distribution of the photoacoustic signal can be grasped from the data. For example, a form may be taken in which the photoacoustic signal intensity is exhibited on a three-dimensional space, or a form may be taken in which the photoacoustic signal intensity is exhibited on a two-dimensional plane. In addition, the following form can also be taken: information on the same observation object is acquired by a different imaging method and the positional correspondence relationship between such pieces of information and the photoacoustic intensity distribution is acquired.

In step (a) above, the specimen to which the near-infrared dye-bound phosphorylcholine-containing polymer according to the present embodiment is administered by a method such as oral administration or injection can be used. In step (b) above, an apparatus that emits light with which the specimen is irradiated, and an apparatus that detects the photoacoustic signal emitted from the near-infrared dye-bound phosphorylcholine-containing polymer according to the present embodiment are not particularly limited.

A light source for irradiation of the specimen with light in step (b) above is not limited as long as the light source can irradiate the specimen with laser pulse light having at least one wavelength selected from the range from 600 nm to 1300 nm. Examples of the apparatus for irradiating the specimen with laser pulse light include a titanium sapphire laser (LT-2211-PC, manufactured by Lotis TII), an OPO laser (LT-2214 OPO, manufactured by Lotis TII) and an alexandrite laser.

The apparatus for detecting the acoustic wave is not particularly restricted and various apparatuses can be used. For example, such detection can be conducted using a commercially available PAT apparatus (Nexus128, manufactured by Endra Inc.).

The imaging method using the near-infrared dye-bound phosphorylcholine-containing polymer according to the present embodiment can image an objective site such as a tumor, a lymph node or a blood vessel through steps (a) and (b) above.

EXAMPLES

Hereinafter, specific reagents, reaction conditions and the like for use in preparation of a polymer according to each Example of the present invention are described, but such reagents, reaction conditions and the like can be modified and such modifications are encompassed in the scope of the present invention. Accordingly, the following Examples are given for assisting understanding of the present invention, and are not limit the scope of the present invention at all. In each Example described below, the measurement method of the number average molecular weight is the proton NMR method.

Example 1

Synthesis of PMPC (Formula (40))

PMPC represented by formula (40) was synthesized according to Reaction formula 5.

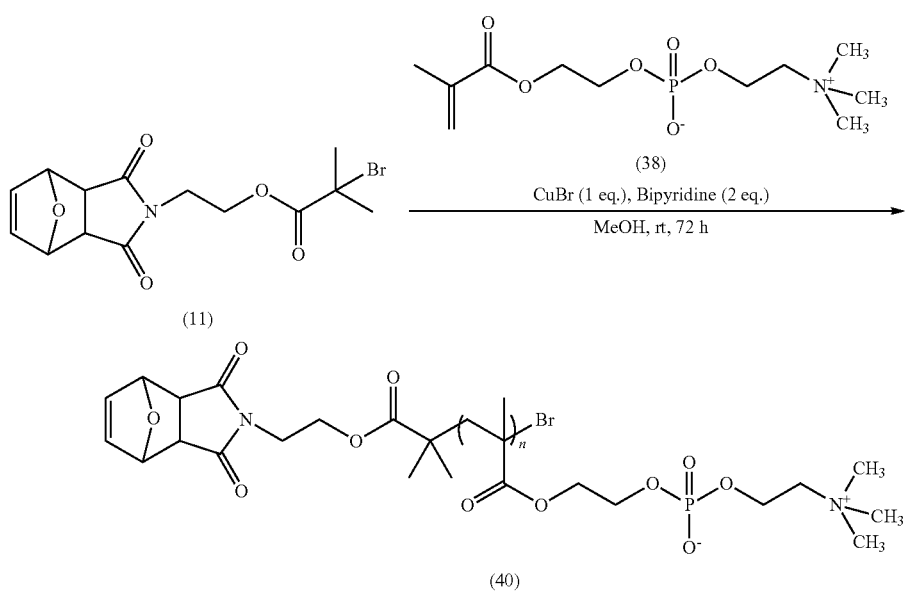

The following operation was performed in a glove box (under a nitrogen atmosphere). MPC (produced by Tokyo Chemical Industry Co., Ltd.) represented by formula (38) (499.8 mg, 1.694 mmol) and 2.5 mL of dehydrated methanol (produced by Wako Pure Chemical Industries, Ltd.) were added into a 20-mL vial. A solution (0.5 mL) of each of a polymerization initiator represented by formula (11) (14.5 mg, 0.04 mmol), CuBr (5.74 mg, 0.04 mmol, produced by Wako Pure Chemical Industries, Ltd.) and 2,2'-bipyridine (12.4 mg, 0.08 mmol, produced by Nacalai Tesque) in dehydrated methanol was prepared. The solution was added to the reaction solution including a compound of formula (38), and the resultant was stirred at room temperature for 64 hours. The resulting solution presented red-brown. After completion of the reaction, the solution was allowed to pass through a thin silica gel layer, to remove Cu (developer: methanol), and the eluate was concentrated by an evaporator. Methanol and dehydrated THF were added to the residue to provide a precipitate, and the precipitate was taken by filtration, washed with dehydrated THF and thereafter dried under reduced pressure. A crude product was fractionated and purified by GPC (column used: SB-803HQ, developing solvent: ultrapure water, liquid-feeding rate: 1 mL/min, column temperature: 40° C.) and freeze-dried, and thereafter PMPC represented by formula (40) (white solid, Mn=18000) was obtained. Isolation yield: 75%. The polymer represented by formula (40) may be abbreviated as PMPC-18 k.

The $^1$H NMR spectral data of a compound of formula (40) was shown below.

$^1$H NMR spectrum (400 MHz, D$_2$O) δ/ppm=6.55 (m, furan), 5.21 (m, furan), 4.19 (br, —OCH$_2$CH$_2$OP—, —NCH$_2$CH$_2$O—), 4.12 (br, —OCH$_2$CH$_2$OP—), 3.98 (br, POCH$_2$CH$_2$N—, —NCH$_2$CH$_2$O—), 3.58 (br, —CH$_2$N(CH$_3$)$_3$) 3.14 (s, —N(CH$_3$)$_3$), 2.39-2.50 (—CHCON), 1.82 (br, —CH$_2$—, main chain, —C(CH$_3$)$_2$), 0.81-0.98 (br, —CH$_3$, main chain).

Example 2

Synthesis of PMPCs (PMPC-18 k, PMPC-46 k) Having Different Number Average Molecular Weight The equivalent of the monomer (formula (38)) relative to the polymerization initiator (formula (11)) was changed and the same operation as in Example 1 was performed to provide PMPC-18 k having a number average molecular weight (Mn) of 18000 and PMPC-46 k (Mn=46000).

Example 3

Preparation of Near-Infrared Dye-Bound Phosphorylcholine-Containing Polymer (Retro-Diels Alder Reaction of Protective Group of Polymer Terminal)

Each of PMPC-11 k, PMPC-18 k and PMPC-46 k obtained in Examples 1 and 2 was placed in a glass reaction tube and heated at 125° C. in vacuum for 5 hours to thereby provide maleimide-terminated PMPC represented by formula (41). As a result of $^1$H NMR measurement, the peak of a furan ring disappeared, and a signal at 6.85 ppm derived from a maleimide group was observed.

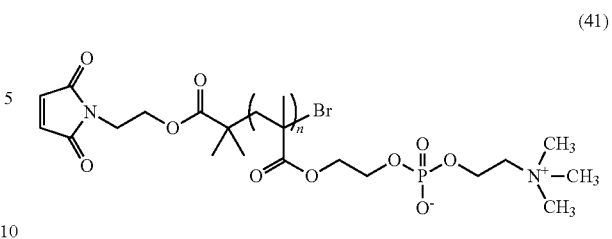

(41)

(Coupling Reaction of ICG Derivative)

The maleimide-terminated PMPC represented by formula (41) was placed in a 1.5-mL Micro-tube, and dissolved in PBS (pH 7.4). Next, 20 equivalents of L-cysteine based on the maleimide group of PMPC was added thereto, and slowly stirred at room temperature for 4 hours. The reaction liquid was transferred to an Amicon Ultra ultrafiltration filter tube (molecular weight cut off: 10K), and centrifuged for 20 minutes (14000 g) and concentrated. Ten mM HEPES (pH 7.8) was added to the concentrated solution, and centrifuged (14000 g) for 20 minutes again. The operation was repeated twice to replace the solvent with 10 mM HEPES (pH 7.8).

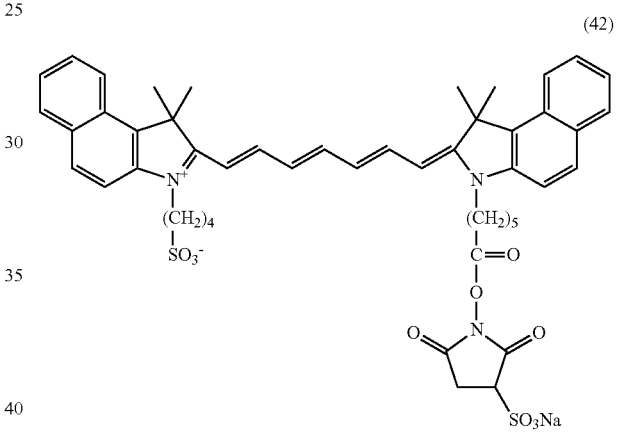

(42)

Next, 1.5 equivalents of a near-infrared dye ICG-Sulfo-OSu (Dojindo Laboratories, code: I254, compound represented by the formula (42), hereinafter, sometimes abbreviated as an "ICG derivative") based on the maleimide group of PMPC was added to the aqueous PMPC solution. The procurement source of ICG-Sulfo-OSu (ICG derivative) below was also Dojindo Laboratories, unless specifically noted.

The ICG-Sulfo-OSu stock solution was prepared as a solution in DMSO. Specifically, a solution obtained by dissolving 1 mg (1.25 μmol) of ICG-Sulfo-OSu in 100 μL of DMSO was used.

The coupling reaction of PMPC and the ICG derivative was performed with rotation and stirring under light shielding at room temperature for 24 hours. Thereafter, the reaction solution was filtered by a 0.22-μm syringe filter to provide ICG derivative-bound PMPC. The coupling reaction of the ICG derivative was performed with respect to each of PMPC-11 k, PMPC-18 k and PMPC-46 k. The resulting near-infrared dye-bound phosphorylcholine-containing polymers may be abbreviated as ICG-PMPC (11 k), ICG-PMPC (18 k) and ICG-PMPC (46 k), respectively.

ICG-PMPC (11 k), ICG-PMPC (18 k) and ICG-PMPC (46 k) obtained were subjected to absorption spectrum measurements of respective solutions thereof, and were found to have maximum absorption wavelengths of 788 nm, 789 nm and 788 nm, respectively.

(Coupling Reaction of Hydrophilic Near-infrared Dye)

A near-infrared cyanine dye IR Dye 800CW NHS Ester (produced by LI-COR, Inc.) was coupled to PMPC in the same manner as in the coupling reaction of the ICG derivative. For the reaction, two types, PMPC-11 k and PMPC-18 k, were used. The resulting compounds may be abbreviated as IRD-PMPC (11 k) and IRD-PMPC (18 k), respectively.

IRD-PMPC (11 k) and IRD-PMPC (18 k) obtained were subjected to absorption spectrum measurements of respective solutions thereof, and were found to have maximum absorption wavelengths of 775 nm and 775 nm, respectively.

Comparative Example 1

Preparation of Near-infrared Dye-bound Polyethylene Glycol

Each of monoamine linear PEG ME-100EA (produced by NOF Corporation, Mw: 10000), monoamine linear PEG ME-200EA (produced by NOF Corporation, Mw: 20000) and monoamine linear PEG ME-400EA (produced by NOF Corporation, Mw: 40000) was dissolved in 50 mM carbonate buffer (pH 9.0) and the $NH_2$ concentration was set to be 0.625 mM. On the other hand, 1 mg (1.25 μmol) of ICG-Sulfo-OSu was dissolved in 100 μl of DMSO. Twenty μl of a solution of ICG-Sulfo-OSu in DMSO was added to carbonate buffer (400 μl) of PEG, and the reaction was performed with the reaction ratio of ICG-Sulfo-OSu to PEG being 1. After rotation and stirring under light shielding at room temperature for 24 hours, the reaction solution was filtered by a 0.22-μm syringe filter to provide a bound substance of PEG and the ICG derivative having a different molecular weight. Hereinafter, one in which the ICG derivative was bound to PEG having a molecular weight of 10000, one in which the ICG derivative was bound to PEG having a molecular weight of 20000 and one in which the ICG derivative was bound to PEG having a molecular weight of 40000 may be abbreviated as ICG-PEG (10 k), ICG-PEG (20 k) and ICG-PEG (40 k), respectively. As described later, the amount of tumor accumulation and the amount of the dye in blood of each of ICG-PEG (10 k), ICG-PEG (20 k) and ICG-PEG (40 k) were quantitatively determined by the same method as in the near-infrared dye-bound phosphorylcholine-containing polymer of the present invention.

Comparative Example 2

Preparation of Near-infrared Dye

For comparison with performances of a near-infrared dye binding to no polymer, the active groups of the ICG derivative and IR Dye 800CW were inactivated. As in Comparative Example 1, 20 μl of a solution of ICG-Sulfo-OSu in DMSO was added to HEPES buffer (400 μl) of glycine, and the reaction was performed with the reaction ratio of ICG-Sulfo-OSu to glycine being 1. After rotation and stirring under light shielding at room temperature for 24 hours, the reaction solution was filtered by a 0.22-μm syringe filter to provide an ICG derivative inactivated by glycine. IR Dye 800CW inactivated by glycine was also obtained in the same manner. Hereinafter, such ICG derivative and IR Dye 800CW may be abbreviated as ICG-G and IR Dye 800CW-G, respectively. As described later, the amount of tumor accumulation and the amount of the dye in blood of each of ICG-G and IR Dye 800CW-G were quantitatively determined by the same method as in the near-infrared dye-bound phosphorylcholine-containing polymer of the present invention.

Example 4

Evaluation of Tumor-imaging Ability by Fluorescence Imaging

The tumor-imaging ability of the near-infrared dye-bound phosphorylcholine-containing polymer obtained in Example 3 above was evaluated by fluorescence imaging by use of a cancer-bearing mouse. In the fluorescence imaging experiment, a female outbred BALB/c Slc-nu/nu mouse (6-week-old at the time of purchase) (Japan SLC, Inc.) was used. For one week before the mouse was allowed to bear a cancer, normal diet and bed were used to habituate the mouse to an environment where the diet and drinking water were available ad libitum. Before about one week of the imaging experiment, $1 \times 10^6$ colon 26 mouse colon cancer cells (RIKEN) were subcutaneously injected into the shoulder and femur area of the mouse.

With respect to the whole-body fluorescence image of the cancer-bearing mouse to which each of ICG-PMPC (11 k), ICG-PMPC (18 k), IRD-PMPC (11 k) and IRD-PMPC (18 k) was administered, the bright field image and the fluorescence image of the mouse after 24 hours of the administration were acquired using IVIS (registered trademark) Imaging System 200 Series (XENOGEN). The amounts of ICG-PMPC (11 k), ICG-PMPC (18 k), IRD-PMPC (11 k) and IRD-PMPC (18 k) to be administered were 20, 5, 1 and 3 nmol per mouse as the amount of the dye, respectively, and such dyes were each injected as 100 μL of a PBS solution to the tail vein of each mouse. For comparison, ICG-PEG (10 k) and ICG-PEG (20 k) as well as ICG-PEG (40 k), ICG-G and IR Dye 800CW-G obtained in Comparative Examples 1 and 2 were also subjected to the same evaluation. The amount of each of such dyes to be administered for comparison was 13 nmol per mouse as the amount of the dye, and such dyes were each injected as 100 μL of a PBS solution to the tail vein of each mouse.

FIG. 1 illustrates a representative example of a fluorescence image of a mouse at 24 hours after administration of the compound of the present invention. ICG-PMPC (18 k) was administered to the mouse. In FIG. 1, strong fluorescent signals were observed on tumor sites (shoulder and femur area) at two positions indicated by black arrows. On the other hand, no strong fluorescent signals were observed from tissues other than the tumors.

In order to evaluate the tumor-imaging ability, the fluorescent intensity of a tumor site (measured area: 0.5×0.5 cm) and the fluorescent intensity (selected as a normal site, measured area: 0.5×0.5 cm) of the base of a leg were quantified from the fluorescence imaging data illustrated in FIG. 1. The ratio of the intensities, namely, the value obtained by dividing the value of the fluorescent intensity of a tumor site by the value of the fluorescent intensity of a normal site, was expressed by a numeral value as SNR (signal-to-noise ratio). The SNR is a parameter showing the tumor-imaging ability of each compound, and a higher SNR results in a more effective contrast agent of a tumor. Table 1 shows the SNR of each compound. The SNR of the near-infrared dye-bound phosphorylcholine-containing polymer of the present invention was 1.9 or more and was higher than the SNR of the compound in each of Comparative Examples. It has been shown from the results that the near-infrared dye-bound phosphorylcholine-containing polymer according to each Example of the present invention is excellent in tumor-imaging ability.

TABLE 1

SNR of compound

| | Compound | SNR |
|---|---|---|
| Comparative Example | ICG-G | 1.0 |
| Example | ICG-PMPC (11k) | 2.8 |
| Example | ICG-PMPC (18k) | 2.1 |
| Comparative Example | IRDye800CW-G | 1.1 |
| Example | IRD-PMPC (11k) | 2.1 |
| Example | IRD-PMPC (18k) | 1.9 |
| Comparative Example | ICG-PEG (10k) | 1.2 |
| Comparative Example | ICG-PEG (20k) | 1.2 |
| Comparative Example | ICG-PEG (40k) | 1.4 |

Example 5

Evaluations of Tumor Accumulation Property and Residual Rate in Blood of Compound The amount of the dye in a tumor and the amount of the dye in blood with respect to each mouse in the tumor-imaging experiment performed in Example 4 were quantitatively determined to thereby evaluate the tumor accumulation property and the residual rate in blood of each compound.

The tumor accumulation property was expressed as the rate of dye transfer (% ID/g) to a tumor relative to the amount of the dye to be administered per gram of the tumor. First, the mouse was euthanized by a carbon dioxide gas after 24 hours of administration, and thereafter the tumor was surgically resected. The tumor was transferred to a plastic tube, an aqueous 1% Triton-X100 solution was added at 1.25 times the weight of the tumor, and the tumor was crushed using a plastic pestle. Next, dimethylsulfoxide (DMSO) was added at 20.25 times the weight of the tumor tissue. The fluorescent intensity of the solution of the tumor crushed, treated as described above, was measured in the plastic tube using IVIS (registered trademark) Imaging System 200 Series (XENOGEN) to thereby measure the amount of the dye in the tumor.

The residual rate in blood was expressed as the rate of dye transfer (% ID/g) to blood relative to the amount of the dye to be administered per gram of blood (1 mL when the specific gravity was assumed to be 1). A blood sample was taken from the tail vein of the mouse after 24 hours of administration, and the blood sample, 1% Triton and DMSO were mixed in the plastic tube in a ratio of 2:9:9. The fluorescent intensity of the blood solution treated as described above was measured in the plastic tube using IVIS (registered trademark) Imaging System 200 Series (manufactured by XENOGEN) to thereby measure the amount of the dye in blood.

The tumor/blood ratio was calculated by the above measurements. The ratio corresponds to the ratio of the tumor accumulation property to the residual rate in blood, and a higher ratio means a higher tumor-imaging ability.

The results are shown in Table 2. The tumor accumulation property of the near-infrared dye-bound phosphorylcholine-containing polymer of the present invention was from 1.1 to 9.7% ID/g, and a highest tumor accumulation property of 9.7% ID/g was exhibited in ICG-PMPC (18 k). With respect to the near-infrared dye-bound phosphorylcholine-containing polymers according to Examples of the present invention, the tumor accumulation property was varied depending on the difference between the dyes. That is, a higher tumor accumulation property was achieved in ICG-PMPCs than IRD-PMPCs. The result means that, while the ICG derivative has the property of being relatively easily associated, IR Dye 800CW including sulfonic acid introduced in a large number is a dye high in dispersibility, and such a difference in the property between the dyes can be reflected. ICG-PMPCs according to Examples of the present invention were observed to have a sufficiently increased tumor accumulation property as compared with ICG-G of Comparative Example.

Surprisingly, the tumor/blood ratios of ICG-PMPCs and IRD-PMPCs according to Examples of the present invention were higher than the ratio in each Comparative Example. The reason for this is because ICG-PMPCs and IRD-PMPCs according to Examples of the present invention exhibit tumor accumulation property, but exhibit a low residual rate in blood. That is, it is meant that the tumor-imaging ability is high. The result has the same tendency as in the value of the SNR of fluorescence imaging in Example 4. ICG-PEGs of Comparative Examples exhibit a high tumor accumulation property, but also exhibit a high residual rate in blood and therefore do not exhibit a high tumor/blood ratio. It is considered from the results that ICG-PMPCs and IRD-PMPCs according to Examples of the present invention can exhibit a high sensitivity and a high tumor accumulation property to photoacoustically image a tumor.

TABLE 2

Tumor accumulation property, residual rate in blood, and tumor/blood ratio of compound

| | Compound | Tumor accumulation property (% ID/g) | Residual rate in blood (% ID/g) | Tumor/blood ratio (Tumor/Blood) |
|---|---|---|---|---|
| Comparative Example | ICG-G | 0.5 | 0.0 | Uncalculatable |
| Example | ICG-PMPC (11k) | 5.3 | 0.5 | 11.0 |
| Example | ICG-PMPC (18k) | 9.7 | 0.9 | 11.0 |
| Example | ICG-PMPC (46k) | 4.1 | 1.5 | 2.8 |
| Example | IRD-PMPC (11k) | 1.1 | 0.2 | 5.0 |
| Example | IRD-PMPC (18k) | 3.2 | 0.7 | 4.6 |
| Comparative Example | ICG-PEG (10k) | 5.6 | 1.4 | 4.0 |
| Comparative Example | ICG-PEG (20k) | 12.4 | 8.4 | 1.5 |
| Comparative Example | ICG-PEG (40k) | 16.8 | 14.4 | 1.2 |

Example 6

Preparation (2) of Near-infrared Dye-bound Phosphorylcholine-containing Polymer

PMPC-18 k obtained in Example 2 was placed in a glass eggplant flask and heated at 125° C. in vacuum for 5 hours to thereby provide maleimide-terminated PMPC. As a result of $^1$H NMR measurement, the peak of a furan ring disappeared, and a signal at 6.85 ppm derived from a maleimide group was observed.

Next, the resulting maleimide-terminated PMPC was placed in a 1.5-mL Micro-tube, and dissolved in PBS (pH 7.4). Twenty equivalents of L-cysteine based on the maleimide group of PMPC was added thereto, and slowly stirred at 4° C. for 16 hours. The reaction liquid was transferred to an Amicon Ultra ultrafiltration filter tube (molecular weight cut off: 10K), and centrifuged (2600×g) for 60 minutes and concentrated. Fifty mM carbonate buffer (pH 8.2) was added to the concentrated solution, and centrifuged (2600×g) for 60 minutes again. The operation was repeated twice to replace the solvent with the 50 mM carbonate buffer (pH 8.2). The cysteinated PMPC here obtained is abbreviated as "Cys-PMPC" hereinafter.

Figure 2:
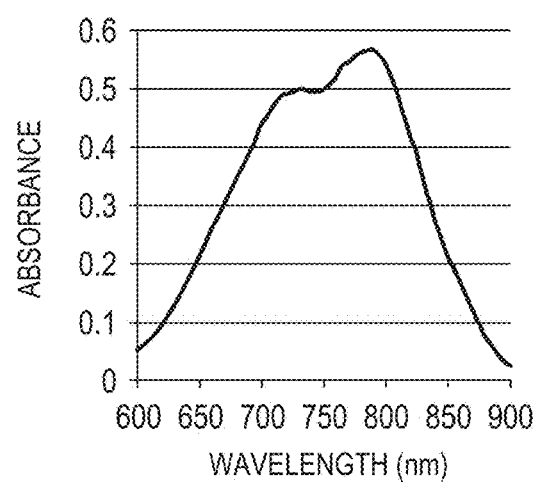
FIG. 2 is a diagram illustrating an absorption spectrum of ICG-PMPC (18 k) #2 in water, according to Example of the present invention.

Next, 1.5 equivalents of the ICG derivative based on the maleimide group of PMPC was added to the aqueous Cys-PMPC solution. The coupling reaction of Cys-PMPC and the ICG derivative was performed with rotation and stirring under light shielding at room temperature for 24 hours. Thereafter, the reaction solution was transferred to a dialysis tube having a pore size of a molecular weight cut off of 3500, and dialyzed to methanol to thereby remove the unreacted ICG derivative from the reaction solution. Thereafter, the reaction solution subjected to replacement with methanol was evaporated to dryness by an evaporator, thereafter a green solid was dissolved in water, and thereafter the solution was filtered by a 0.22-µm syringe filter to thereby provide ICG derivative-bound PMPC. The resulting near-infrared dye-bound phosphorylcholine-containing polymer is abbreviated as "ICG-PMPC (18 k) #2". The absorption spectrum of ICG-PMPC (18 k) #2 in water is illustrated in FIG. 2. As illustrated in FIG. 2, it has been found that ICG-PMPC (18 k) #2 has a maximum absorption wavelength of 788 nm.

As a result of dynamic light scattering measurement (measurement apparatus: Zeta Sizer Nano manufactured by Malvern Instruments) of an aqueous ICG-PMPC (18 k) #2 solution, it was shown that ICG-PMPC (18 k) #2 formed a nanoparticle in water. The Z average particle size was 75 nm on average. The polydispersity index (PDI) was 0.4.

Example 7

Measurement of Photoacoustic Signal

The photoacoustic signal of an aqueous solution of ICG-PMPC (18 k) #2 obtained in Example 6 was measured. The photoacoustic signal was measured by irradiating an aqueous sample solution with pulse laser light, detecting the photoacoustic signal from the sample by using a piezoelectric element, amplifying the signal by a high-speed preamplifier, and then acquiring the signal by a digital oscilloscope. Specific conditions were as follows. A titanium sapphire laser (LT-2211-PC, manufactured by Lotis TII) was used as a light source. The laser wavelength was 790 nm. The energy density was from about 10 to 20 mJ/cm$^2$, the pulse width was about 20 nanoseconds, and the pulse repetition frequency was 10 Hz. As the piezoelectric element for detecting the photoacoustic signal, a non-convergence type ultrasonic transducer (V303, manufactured by Panametrics-NDT) having an element diameter of 1.27 cm and a central band of 1 MHz was used. The measurement vessel was a polystyrene cuvette having an optical path length of 0.1 cm and a sample volume of about 200 µl. The measurement vessel and the piezoelectric element were immersed in a glass vessel filled with water and the distance therebetween was set to be 2.5 cm. As the high-speed preamplifier for amplifying the photoacoustic signal intensity, an ultrasonic preamplifier (Model 5682, manufactured by Olympus Corp.) having an amplification degree of +30 dB was used. The signal amplified was input to a digital oscilloscope (DP04104, manufactured by Tektronix). The polystyrene cuvette was irradiated with pulse laser light from the outside of the glass vessel. A portion of scattering light generated here was detected by a photodiode, and input as a trigger signal to the digital oscilloscope. The digital oscilloscope was set to a 32 run-averaging display mode to measure the photoacoustic signal intensity on average of 32 laser pulse irradiations.

Figure 3:
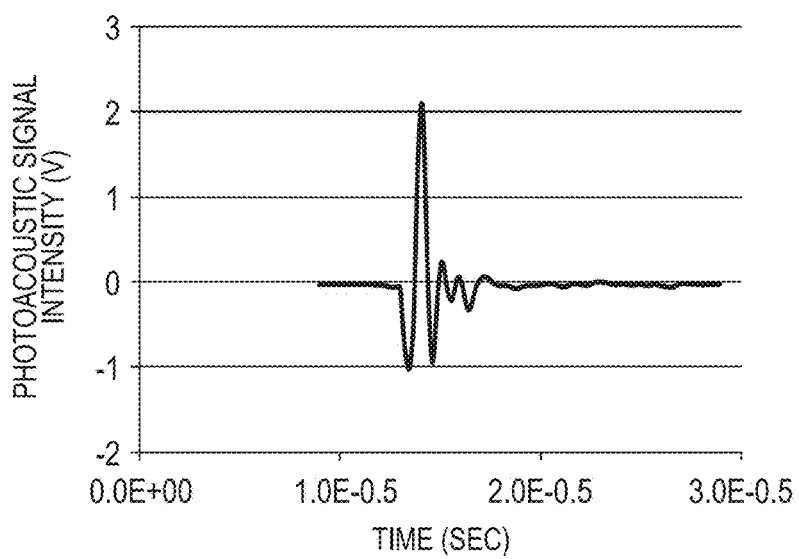
FIG. 3 is a diagram illustrating the waveform of the photoacoustic signal intensity of an aqueous ICG-PMPC (18 k) #2 solution according to Example of the present invention.

FIG. 3 illustrates the waveform of the photoacoustic signal intensity of the aqueous ICG-PMPC (18 k) #2 solution according to Example of the present invention. As is clear from FIG. 3, ICG-PMPC (18 k) #2 was revealed to emit a photoacoustic signal.

Example 8

In Vivo Kinetic Evaluation of ICG-PMPC (18 k) #2

The tumor-imaging ability of ICG-PMPC (18 k) #2 was evaluated by the same method as in Example 4. The ratio of the fluorescent intensity of a tumor site to the fluorescent intensity of a normal site was calculated as SNR (signal-to-noise ratio) from the fluorescence imaging data, and as a result, was 2.6. As in the result in Example 4, a high SNR was exhibited as compared with the SNR in each Comparative Example. In addition, the tumor accumulation property of ICG-PMPC (18 k) #2 was measured by the same method as in Example 5, and as a result, was 6.4% ID/g.

Example 9

Photoacoustic Imaging of Tumor by ICG-PMPC (18 k) #2

Figure 4A:
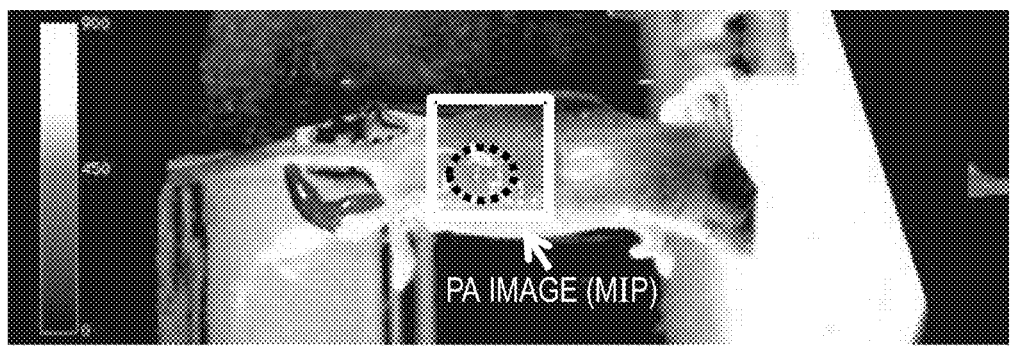
FIG. 4A illustrates a superimposed image of an optical photograph and a photoacoustic imaging image [Maximum intensity projection (MIP) image] surrounded with a white square frame, of a cancer-bearing mouse imaged before administration of ICG-PMPC (18 k) #2 according to Example of the present invention.
Figure 4B:
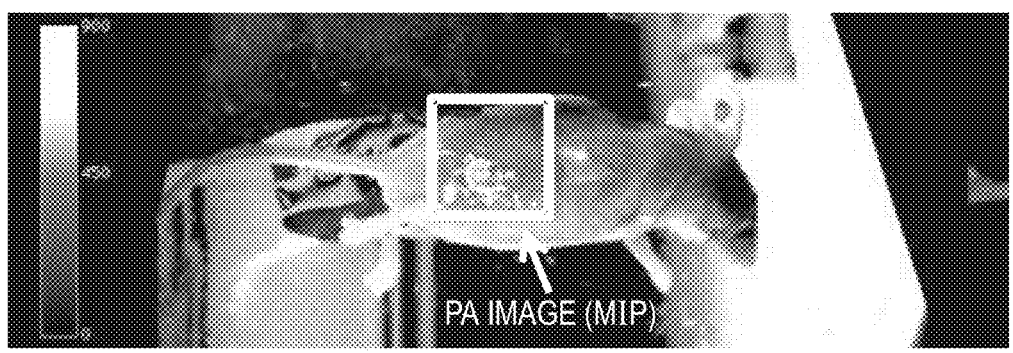
FIG. 4B illustrates a superimposed image of an optical photograph and a photoacoustic imaging image (MIP image) surrounded with a white square frame, of a cancer-bearing mouse imaged one day after administration of ICG-PMPC (18 k) #2 according to Example of the present invention.

ICG-PMPC (18 k) #2 was administered in an amount of the dye of 45 nmol to the cancer-bearing mouse prepared in the method described in Example 4, and a commercially available PAT apparatus (Nexus 128, manufactured by Endra Inc.) was used to perform measurement before administration and one day after administration. The measurement wavelength was 790 nm. FIG. 4A illustrates a superimposed image of an optical photograph and a photoacoustic imaging image (MIP image) surrounded with a white square frame, of the cancer-bearing mouse imaged before administration of ICG-PMPC (18 k) #2. In FIG. 4A, a tumor is present in a region surrounded by a black dotted line. FIG. 4B illustrates a superimposed image of an optical photograph and a photoacoustic imaging image (MIP image) surrounded with a white square frame, of the same cancer-bearing mouse as the mouse illustrated in FIG. 4A, imaged one day after administration of ICG-PMPC (18 k) #2. As is clear from FIGS. 4A and 4B, the photoacoustic signal in the tumor region one day after administration of ICG-PMPC (18 k) #2 was found to be increased as compared with the case before the administration. As the analysis result of the photoacoustic signal intensity, the signal intensity after the administration was found to be increased up to 2.9 times the signal intensity before administration. It has been revealed from the results that a compound in which a dye having absorption in the near-infrared wavelength region is bound to a polymer having phosphorylcholine as a side chain serves as a photoacoustic tumor contrast agent.

Example 10

Synthesis of PMPC-Fmoc

PMPC-Fmoc represented by formula (44) was synthesized according to Reaction formula 6.

through a thin silica gel layer, to remove Cu (developer: methanol), and the eluate was concentrated by an evaporator. Methanol and dehydrated THF were added to the residue to provide a precipitate, and the precipitate was taken by filtration, washed with dehydrated THF and thereafter dried under reduced pressure. A crude product was dissolved in ultrapure water, the solution was transferred to an Amicon Ultra ultrafiltration filter tube (molecular weight cut off: 3K), centrifuged (5000 g) for 30 minutes and concentrated. Ultrapure water was added to the concentrated solution, and centrifuged (5000 g) for 30 minutes again. The operation was repeated twice, the resulting residue was freeze-dried,

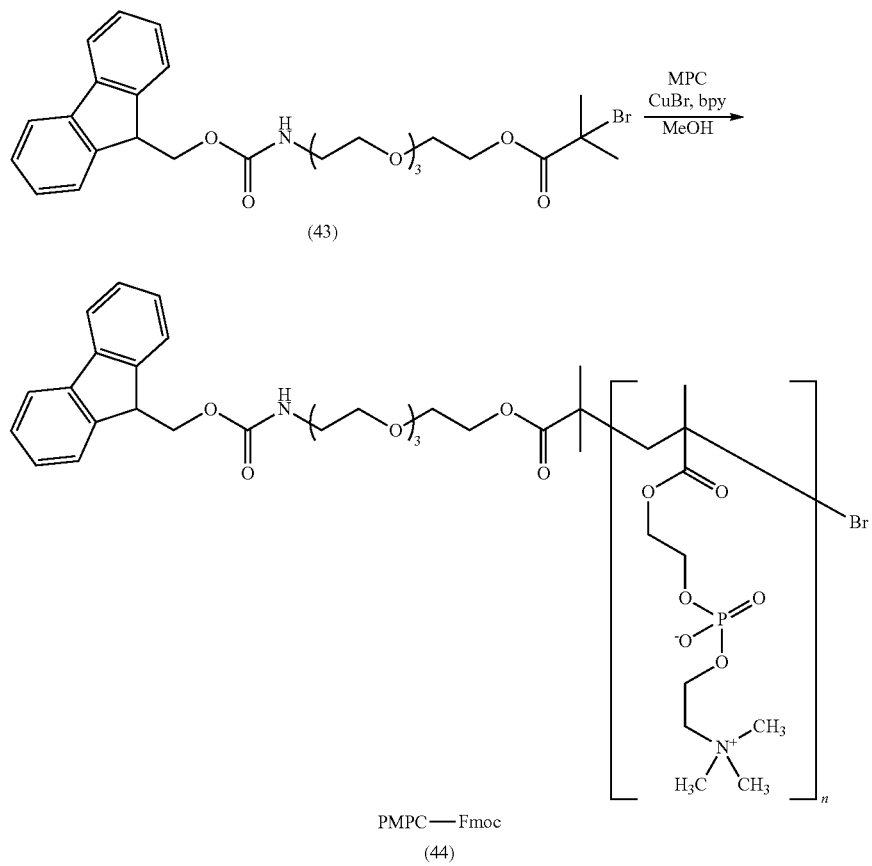

Reaction formula 6

The following operation was performed in a glove box (under a nitrogen atmosphere). MPC represented by formula (38) (produced by Tokyo Chemical Industry Co., Ltd.) (469.4 mg, 1.59 mmol) and 2.0 mL of dehydrated methanol (produced by Wako Pure Chemical Industries, Ltd.) were added into a 5-mL vial. A solution (0.1 mL) of each of a polymerization initiator represented by formula (43) (13.2 mg, 0.023 mmol), CuBr (3.37 mg, 0.023 mmol, produced by Wako Pure Chemical Industries, Ltd.) and 2,2'-bipyridine (7.33 mg, 0.046 mmol, produced by Nacalai Tesque) in dehydrated methanol was prepared. The solution was added to the reaction solution including the compound of formula (38), and the resultant was stirred at room temperature for 96 hours. The resulting solution presented red-brown. After completion of the reaction, the solution was allowed to pass and thereafter PMPC-Fmoc represented by formula (44) (white solid, Mn=50000) was obtained.

$^1$H NMR spectrum (400 MHz, D$_2$O) δ/ppm=7.92-7.68 (m, 9-fluorenyl), 3.98-4.19 (br, —OCH$_2$CH$_2$OP—, —NCH$_2$CH$_2$O—, —OCH$_2$CH$_2$OP—, —POCH$_2$CH$_2$N—, —NCH$_2$CH$_2$O—, —CH$_2$CH$_2$O—), 3.58 (br, —CH$_2$N (CH$_3$)$_3$), 3.14 (s, —N(CH$_3$)$_3$), 1.82 (br, —CH$_2$—, main chain, —C(CH$_3$)$_2$), 0.81-0.98 (br, —CH$_3$, main chain).

Example 11

Synthesis of PMPC—NH$_2$

PMPC-NH$_2$ having an amino group at the terminal, represented by formula (45), was synthesized according to Reaction formula 7.

Reaction formula 7

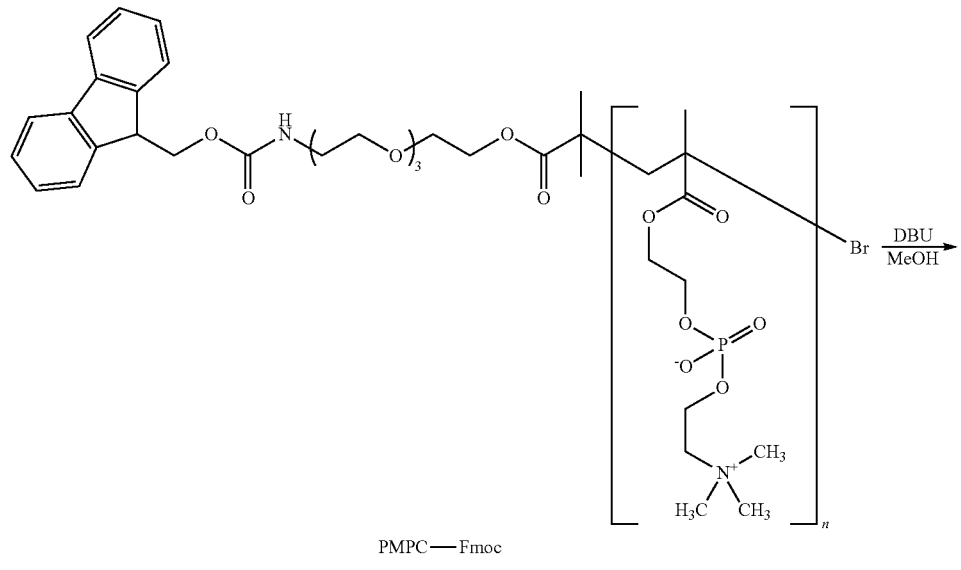

PMPC—Fmoc
(44)

PMPC—NH$_2$
(45)

PMPC-Fmoc represented by formula (44) (102.3 mg, 2.0 μmol), DBU (40 μL) and 4.0 mL of dehydrated methanol (produced by Wako Pure Chemical Industries, Ltd.) were added into a 20-mL vial, and stirred at room temperature for 24 hours. Progress of the reaction was confirmed by the ninhydrin color reaction method.

After completion of the reaction, the reaction solution was diluted with ultrapure water, and the solution was transferred to an Amicon Ultra ultrafiltration filter tube (molecular weight cut off: 10K), centrifuged (5000 g) for 30 minutes and concentrated. Ultrapure water was added to the concentrated solution, and centrifuged (5000 g) for 30 minutes again. The operation was repeated twice, the resulting residue was freeze-dried, and thereafter PMPC-NH$_2$ represented by formula (45) was quantitatively obtained. It was confirmed from $^1$H NMR measurement that the peak (7.92-7.68 ppm) of a 9-fluorenyl ring disappeared.

Example 12

Coupling Reaction of ICG Derivative

PMPC-NH$_2$ represented by formula (45) (84 mg, 1.68 μmol), a near-infrared dye ICG-Sulfo-OSu (2.9 mg, 3.197 μmol) and 2.0 mL of dehydrated methanol (produced by Wako Pure Chemical Industries, Ltd.) were added into a 10-mL vial, and stirred at room temperature under light shielding for 48 hours. After completion of the reaction, the reaction solution was diluted with ultrapure water, and the solution was transferred to an Amicon Ultra ultrafiltration filter tube (molecular weight cut off: 10K), centrifuged (5000 g) for 30 minutes and concentrated. Ultrapure water was added to the concentrated solution, and centrifuged (5000 g) for 30 minutes again. The operation was repeated twice, the resulting crude product was fractionated and purified by a PD-10 column (developing solvent: ultrapure water) and freeze-dried, and thereafter ICG-PMPC (43 k) represented by formula (46) (green solid, Mn=43000) was obtained.

$^1$H NMR spectrum (400 MHz, CD$_3$OD) δ/ppm=8.21-8.23 (m), 7.99-8.00 (m), 7.60-7.66 (m), 6.32-6.64 (m), 4.33 (br), 4.23 (br), 4.08 (br), 3.75 (br), 3.30 (s) 1.82-2.36 (br), 0.96-1.32 (br).

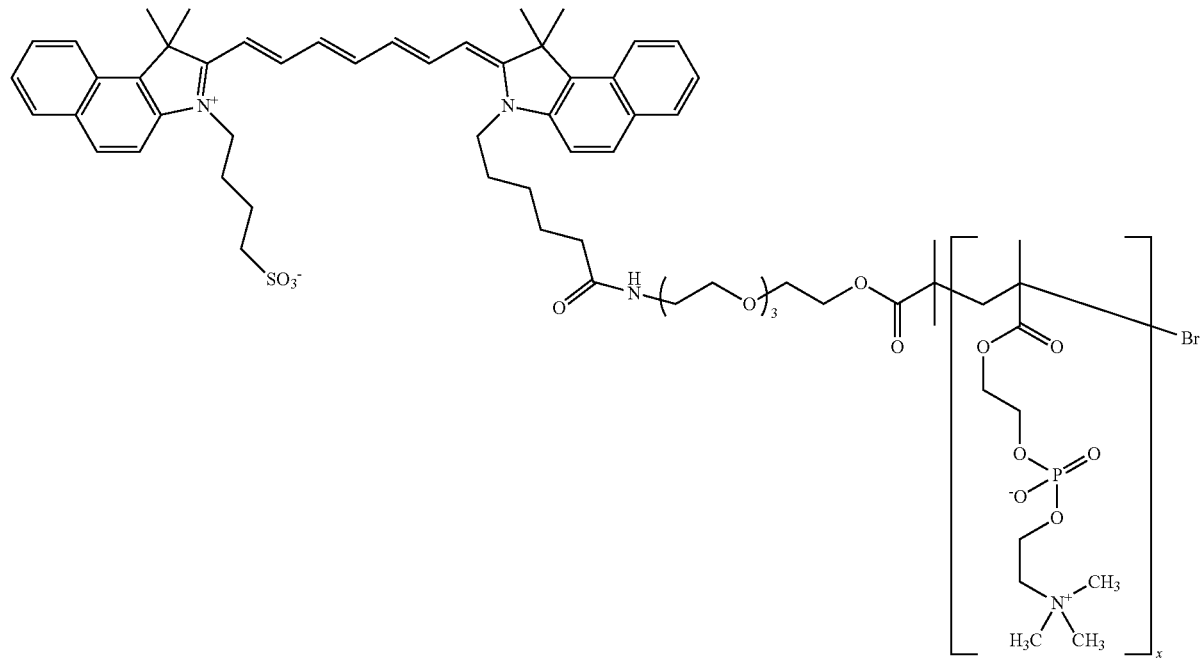

(46)

Dynamic light scattering measurement (measurement apparatus: Zeta Sizer Nano manufactured by Malvern Instruments) of the aqueous ICG-PMPC (43 k) solution (50 µM) was performed, and as a result, the Z average particle size was 157 nm on average.

ICG-PMPC (43 k) was subjected to GPC (column used: SB-803HQ, developing solvent: 0.1 M $NaNO_3$, aqueous 0.2% $NaN_3$ solution, liquid-feeding rate: 1 mL/min, column temperature: 40° C.) measurement, and as a result, the elution peak with respect to ICG-PMPC (43 k) was observed at 7.46 min. On the other hand, the elution peaks with respect to $PMPC-NH_2$ and ICG were observed at 7.53 min and 10.15 min, respectively, under the same conditions (FIG. 5).

Example 13

Photoacoustic Imaging of Tumor by ICG-PMPC (43 k)

Colon 26 mouse colon cancer cells ($0.8 \times 10^6$ cells, 50% Geltrex saline solution) (50 µL) were subcutaneously injected to the right shoulder of a Balb/c nu-nu female mouse (6-week-old) to prepare a cancer-bearing mouse. One hundred µL of a saline solution (20 nM) of ICG-PMPC (43 k) was administered through the tail vein of the mouse at eight days after cancer bearing.

Photoacoustic imaging (detection wavelengths: 797 nm and 850 nm) of the cancer-bearing mouse individual before administration and one day after administration was performed. FIGS. 6A and 6B illustrate superimposed images of an optical photograph and a photoacoustic imaging image of the cancer-bearing mouse. FIG. 6A illustrates a superimposed image of an optical photograph and a photoacoustic image of the cancer-bearing mouse before administration, and FIG. 6B illustrates a superimposed image of an optical photograph and a photoacoustic image of the same mouse individual one day after administration. In FIGS. 6A and 6B, each white arrow indicates the position of a tumor. As is clear from FIGS. 6A and 6B, the photoacoustic signal in the tumor region one day after administration of ICG-PMPC (43 k) was found to be increased as compared with the signal before administration thereof.

Example 14

Synthesis of ICG-PMPC Having Different Molecular Weight

Compounds ICG-PMPC (12 k), ICG-PMPC (43 k) and ICG-PMPC (50 k) (all were green solids) having a different molecular weight from the molecular weight of PMPC represented by formula (46) were synthesized in the same manner as in Examples 10 to 12. The number average molecular weights of ICG-PMPC (12 k), ICG-PMPC (43 k) and ICG-PMPC (50 k) were 12000, 43000 and 50000, respectively.

Example 15

Particle Size Measurement of ICG-PMPC Having Different Molecular Weight

Dynamic light scattering measurements (measurement apparatus: Zeta Sizer Nano manufactured by Malvern Instruments) of respective aqueous solutions (1 mg/mL) of ICG-PMPC (12 k), ICG-PMPC (43 k) and ICG-PMPC (50 k) obtained in Example 14 were performed, and as a result, the Z average particle sizes were 105, 125 and 137 nm on average, respectively.

Example 16

Synthesis of ICG-Bound PEG (PEG Molecular Weight: 40000) in Comparative Example

Monoamine linear PEG ME-400EA (produced by NOF Corporation, Mw: 40000) (35 mg, 0.88 µmol), a near-infrared dye ICG-Sulfo-OSu (1 mg, 1.08 µmol) and 1.0 mL of dehydrated methanol (produced by Wako Pure Chemical Industries, Ltd.) were added, and stirred at room temperature under light shielding for 48 hours. After completion of the reaction, the reaction solution was diluted with ultrapure water, and the solution was transferred to an Amicon Ultra ultrafiltration filter tube (molecular weight cut off: 10K), centrifuged (5000 g) for 30 minutes and concentrated. Ultrapure water was added to the concentrated solution, and centrifuged (5000 g) for 30 minutes again. The operation was repeated twice, the resulting crude product was fractionated and purified by a PD-10 column (developing solvent: ultrapure water), and freeze-dried, and thereafter ICG-PEG (40 k) (green solid, Mn=40000) was obtained.

Example 17

Synthesis of ICG-bound PEG (PEG Molecular Weight: 12000) in Comparative Example

Monoamine linear PEG MEPA-12T (produced by NOF Corporation, Mw: 12000) and a near-infrared dye ICG-Sulfo-OSu were reacted in the same procedure as in Example 16 to provide ICG-PEG (12 k).

Example 18

Particle Size Measurement of ICG-bound PEG in Comparative Example

Dynamic light scattering measurements (measurement apparatus: Zeta Sizer Nano manufactured by Malvern Instruments) of respective aqueous solutions (1 mg/mL) of the compounds obtained in Examples 16 and 17, ICG-PEG (40 k) and ICG-PEG (12 k), were performed, and as a result, the Z average particle sizes were 194 and 132 nm on average, respectively. The Z average particle sizes of ICG-PEG (40 k) and ICG-PEG (12 k) in PBS buffer (1 mg/mL) were measured in the same manner, and as a result, the average particle sizes were 136 and 130 nm on average, respectively.

Example 19

Evaluation of Tumor-imaging Ability by Fluorescence Imaging

The tumor-imaging ability of each of ICG-PMPC (12 k), ICG-PMPC (43 k) and ICG-PMPC (50 k) obtained in Example 14, and ICG-PEG (40 k) obtained in Example 16, according to Comparative Example, was evaluated by fluorescence imaging.

Colon 26 colon cancer cells ($1.0 \times 10^6$ cells, 50% Geltrex saline solution) (50 μL) were subcutaneously injected into the right shoulder of a Balb/c nu-nu female mouse (6-week-old) to prepare a cancer-bearing mouse. One hundred μL of a saline solution (200 μM) (20 nmol) of each of ICG-PMPC (12 k), ICG-PMPC (43 k) and ICG-PMPC (50 k), and ICG-PEG (40 k) was administered through the tail vein of the mouse at seven days after cancer bearing. With respect to the whole-body fluorescence image of the cancer-bearing mouse to which the saline solution was administered, the bright field image and the fluorescence image of the mouse were acquired using IVIS (registered trademark) Imaging System 200 Series (XENOGEN) before administration, immediately after administration, and after 0.5, 1.5, 2.5, 24 and 48 hours of administration.

Figure 7:
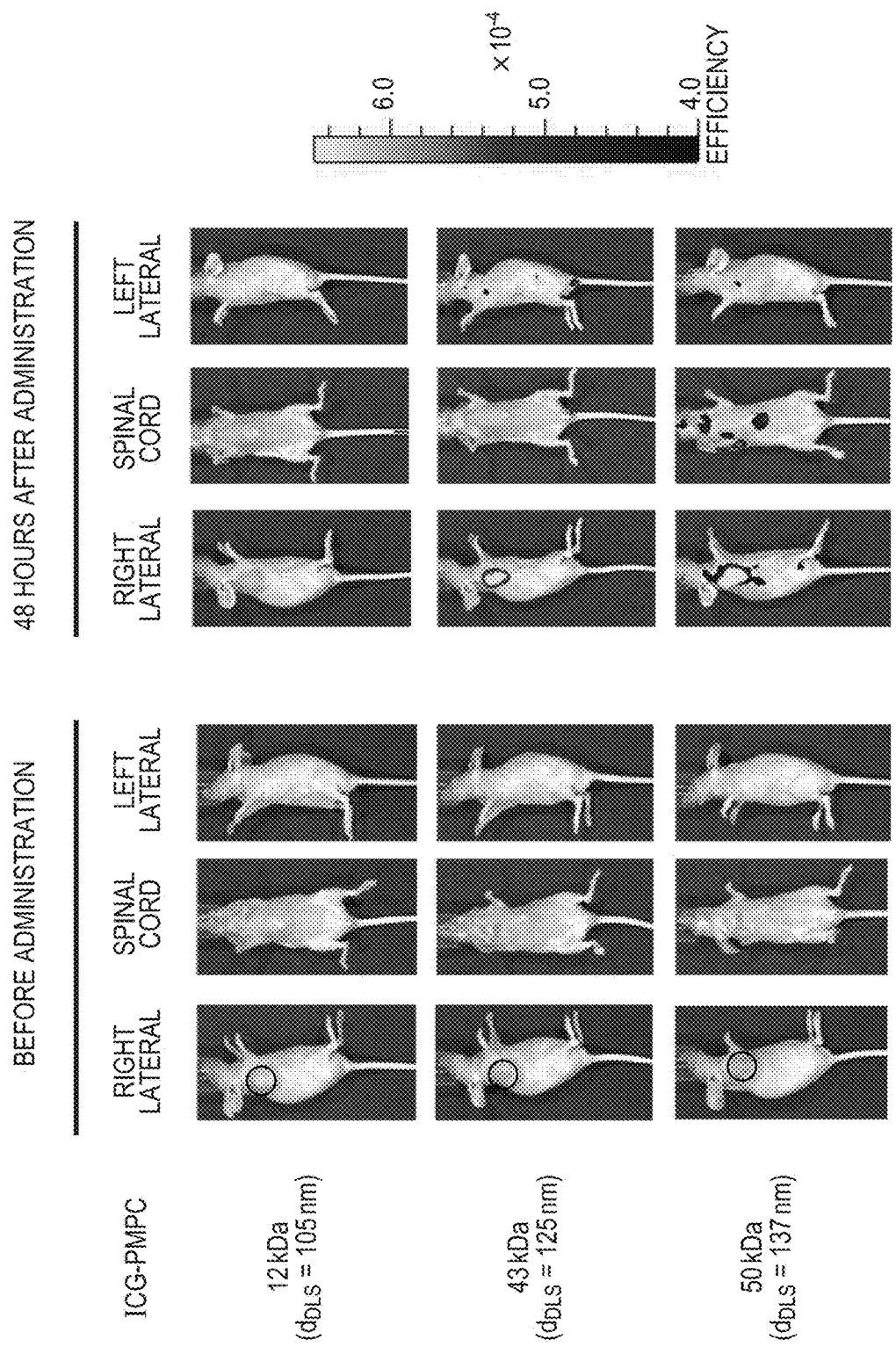
FIG. 7 illustrates superimposed views of near-infrared fluorescent images and bright field images of each mouse before administration and at 48 hours after administration of each of ICG-PMPC (12 k), ICG-PMPC (43 k) and ICG-PMPC (50 k) according to Examples of the present invention (in the Figure, each circle depicted at the right shoulder of each mouse before administration indicates a tumor site).

FIG. 7 illustrates a fluorescence imaging example of the mouse before administration and at 48 hours after administration of each of ICG-PMPC (12 k), ICG-PMPC (43 k) and ICG-PMPC (50 k). A strong fluorescent signal was observed on one tumor site (right shoulder) indicated by a circle, with respect to each of ICG-PMPC (43 k) and ICG-PMPC (50 k). On the other hand, a weak fluorescent signal was observed on the left shoulder as a normal site. Furthermore, the fluorescent signal on a tumor site was observed to be increased according to an increase in the molecular weight of ICG-PMPC.

Figure 8:
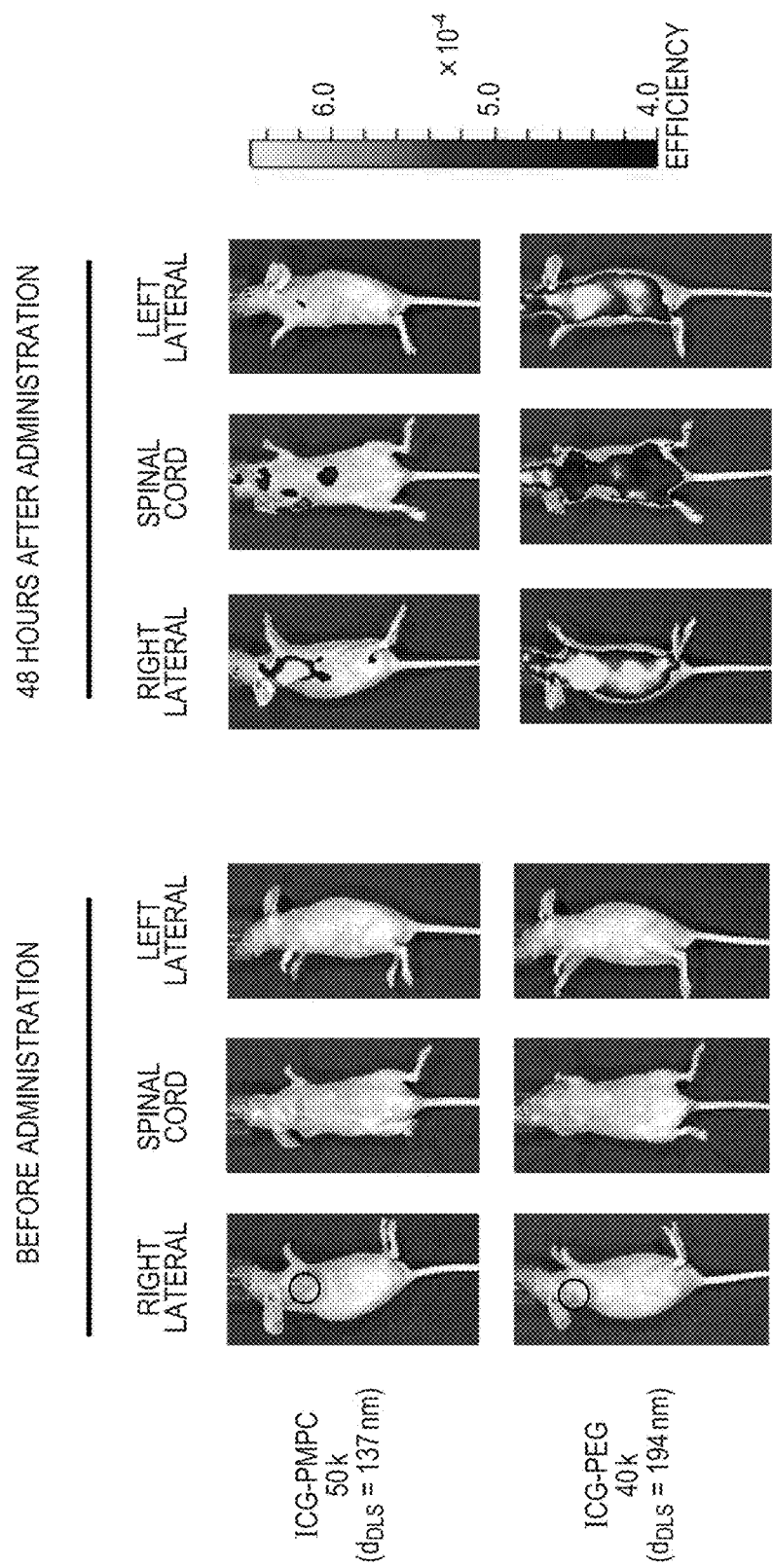
FIG. 8 illustrates superimposed views of near-infrared fluorescent images and bright field images of each mouse before administration and at 48 hours after administration of each of ICG-PMPC (50 k) according to Example of the present invention and ICG-PEG (40 k) according to Comparative Example (in the Figure, each circle depicted at the right shoulder of each mouse before administration indicates a tumor site).

FIG. 8 illustrates a fluorescence imaging example of the mouse before administration and at 48 hours after administration of each of ICG-PMPC (50 k) and ICG-PEG (40 k). The tumor site (right shoulder) was indicated by a circle. While a fluorescent signal was observed from the mouse, to which ICG-PMPC (50 k) was administered, on the tumor site indicated by a circle at 48 hours after administration, a weak fluorescent signal was observed on each of the left shoulder and the mouse abdomen as a normal site. On the other hand, a strong fluorescent signal was observed from the mouse, to which ICG-PEG (40 k) was administered, on not only the tumor site indicated by a circle, but also each of the left shoulder and the mouse abdomen as a normal site at 48 hours after administration.

In order to evaluate the tumor-imaging ability, the fluorescent intensity of ROI of each of the tumor site (right shoulder), the left lateral decubitus bearing no cancer (selected as a normal site) and the liver (abdomen) was quantified from the fluorescence imaging data as illustrated in FIGS. 7 and 8 in Example 19, the quantitative value of the fluorescent intensity (selected as a self-fluorescent intensity) of the tumor site (right shoulder) of the mouse before administration was subtracted therefrom, and the resultant was expressed by a numeral value. Herein, the fluorescent intensity of a normal site was quantified as the average of ROIs at three points of the left lateral decubitus.

Figure 9:
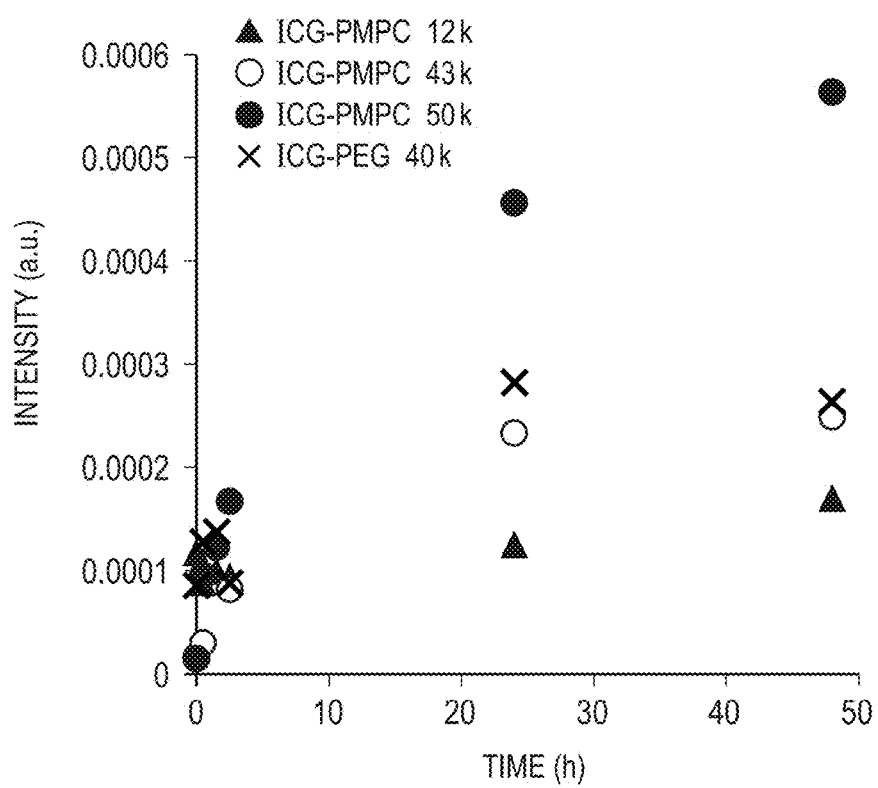
FIG. 9 is a diagram illustrating the change over time in difference intensity of each of ICG-PMPC (12 k), ICG-PMPC (43 k) and ICG-PMPC (50 k) according to Examples of the present invention, and ICG-PEG (40 k) according to Comparative Example.
Figure 10:
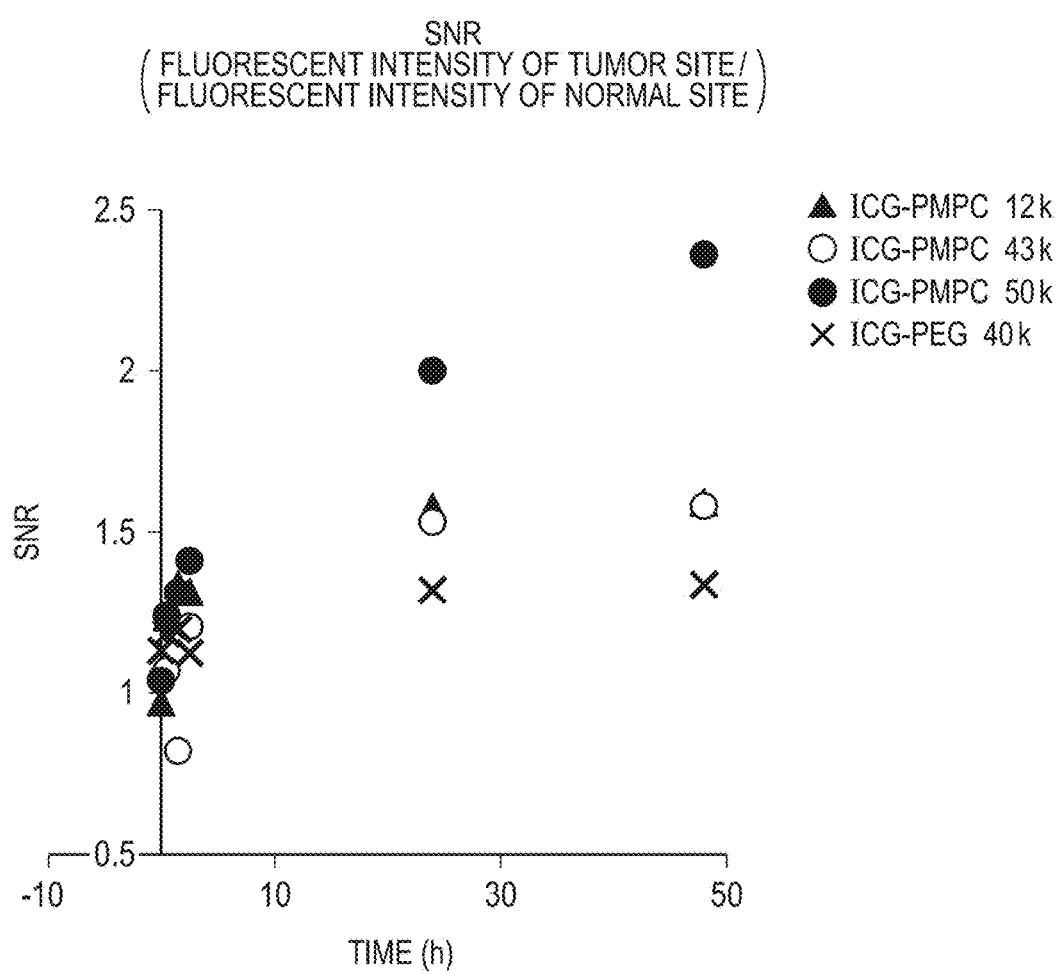
FIG. 10 is a diagram illustrating the change over time in SNR of each of ICG-PMPC (12 k), ICG-PMPC (43 k) and ICG-PMPC (50 k) according to Examples of the present invention, and ICG-PEG (40 k) according to Comparative Example.

The difference intensity and the SNR were used as the indexes of the tumor-imaging ability. The difference intensity here means a numeral value obtained by subtracting the fluorescent intensity of a normal site from the fluorescent intensity of a tumor site, and expressing the resultant by a numeral value. The SNR in Example 19 means the value obtained by dividing the fluorescent intensity value of a tumor site by the fluorescent intensity value of a normal site in Example 19, as described above. The SNR is a parameter representing the tumor-imaging ability of each compound, and a higher SNR is more effective as the contrast agent of a tumor. FIG. 9 illustrates the difference intensity of each of ICG-PMPC (12 k), ICG-PMPC (43 k) and ICG-PMPC (50 k), and ICG-PEG (40 k). From the result, it was shown that the tumor-imaging ability was enhanced according to an increase in the molecular weight of ICG-PMPC. FIG. 10 illustrates the SNR of each of such compounds. From the result, it was shown that ICG-PMPC (50 k) was higher in tumor selectivity than ICG-PEG (40 k).

From the foregoing, the near-infrared dye-bound phosphorylcholine-containing polymers according to Examples of the present invention were shown to be fast in clearance and excellent in tumor-imaging ability as compared with the near-infrared dye-bound polyethylene glycol.

Figure 11:
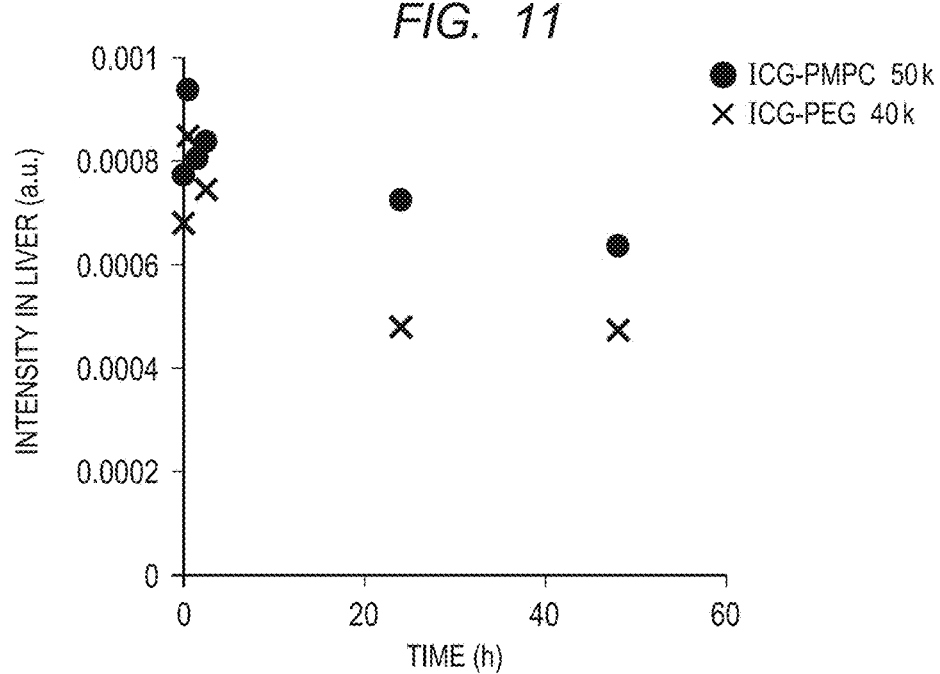
FIG. 11 is a diagram illustrating the change over time in the fluorescent intensity value (quantitative value in the region of interest (hereinafter, abbreviated as "ROI")) of each of ICG-PMPC (50 k) according to Example of the present invention and ICG-PEG (40 k) according to Comparative Example, in the liver (abdomen) of a cancer-bearing mouse.

FIG. 11 illustrates the results of quantification of ROI of the liver (abdomen). The fluorescent signal from the liver site was more strongly observed in ICG-PEG (40 k) than ICG-PMPC (50 k). From the result, the near-infrared dye-bound phosphorylcholine-containing polymer was shown to be low in the accumulation property in the liver and excellent in tumor-imaging ability as compared with the near-infrared dye-bound polyethylene glycol.

Example 20

Photoacoustic Imaging of Tumor

Figure 12A:
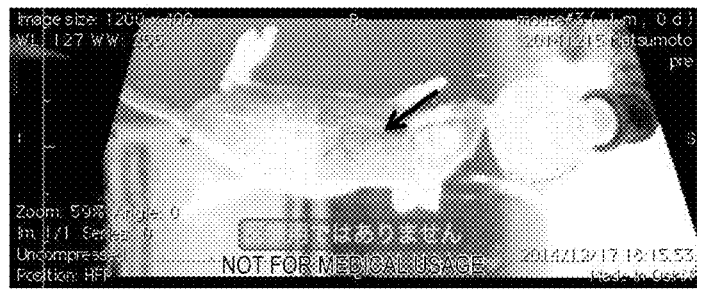
FIGS. 12A and 12B illustrate superimposed images of an optical photograph and a photoacoustic imaging image of a cancer-bearing mouse to which ICG-PMPC (50 k) is administered.
Figure 12B:
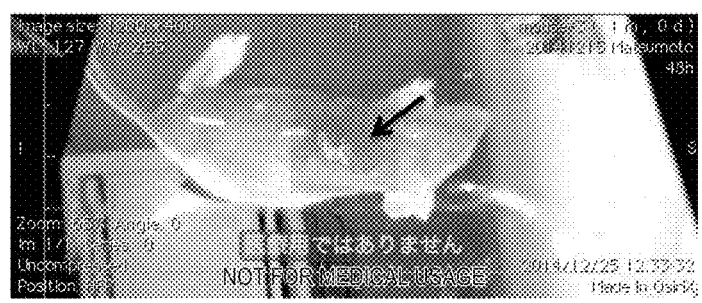

The photoacoustic imaging of a tumor described in Example 13 was performed with respect to each of ICG-PMPC (12 k), ICG-PMPC (43 k) and ICG-PMPC (50 k) obtained in Example 14. Colon 26 mouse colon cancer cells ($1.0 \times 10^6$ cell, 50% Geltrex saline solution) (50 μL) were subcutaneously injected to the right shoulder of a Balb/c nu-nu female mouse (6-week-old) to prepare a cancer-bearing mouse. Two hundreds μL of a saline solution (200 μM) (40 nmol) of each of ICG-PMPC (12 k), ICG-PMPC (43 k) and ICG-PMPC (50 k) was administrated through the tail vein of the mouse at seven days after cancer bearing. The cancer-bearing mouse individual was subjected to photoacoustic imaging (detection wavelengths: 797 nm and 850 nm) before administration and one day after administration. FIG. 12A and FIG. 12B illustrate a superimposed image of an optical photograph and a photoacoustic imaging image of the cancer-bearing mouse to which ICG-PMPC (50 k) was administered. FIG. 12A illustrates a superimposed image of an optical photograph and a photoacoustic image of the cancer-bearing mouse before administration, and FIG. 12B illustrates a superimposed image of an optical photograph and a photoacoustic image of the same mouse individual two days after administration. In FIG. 12A and FIG. 12B, each arrow indicates the position of a tumor. As is clear from FIG. 12A and FIG. 12B, the photoacoustic signal in the tumor region two days after administration of ICG-PMPC (50 k) was found to be increased as compared with the signal before administration thereof and ICG-PMPC (50 k) could image a tumor.

Figure 13:
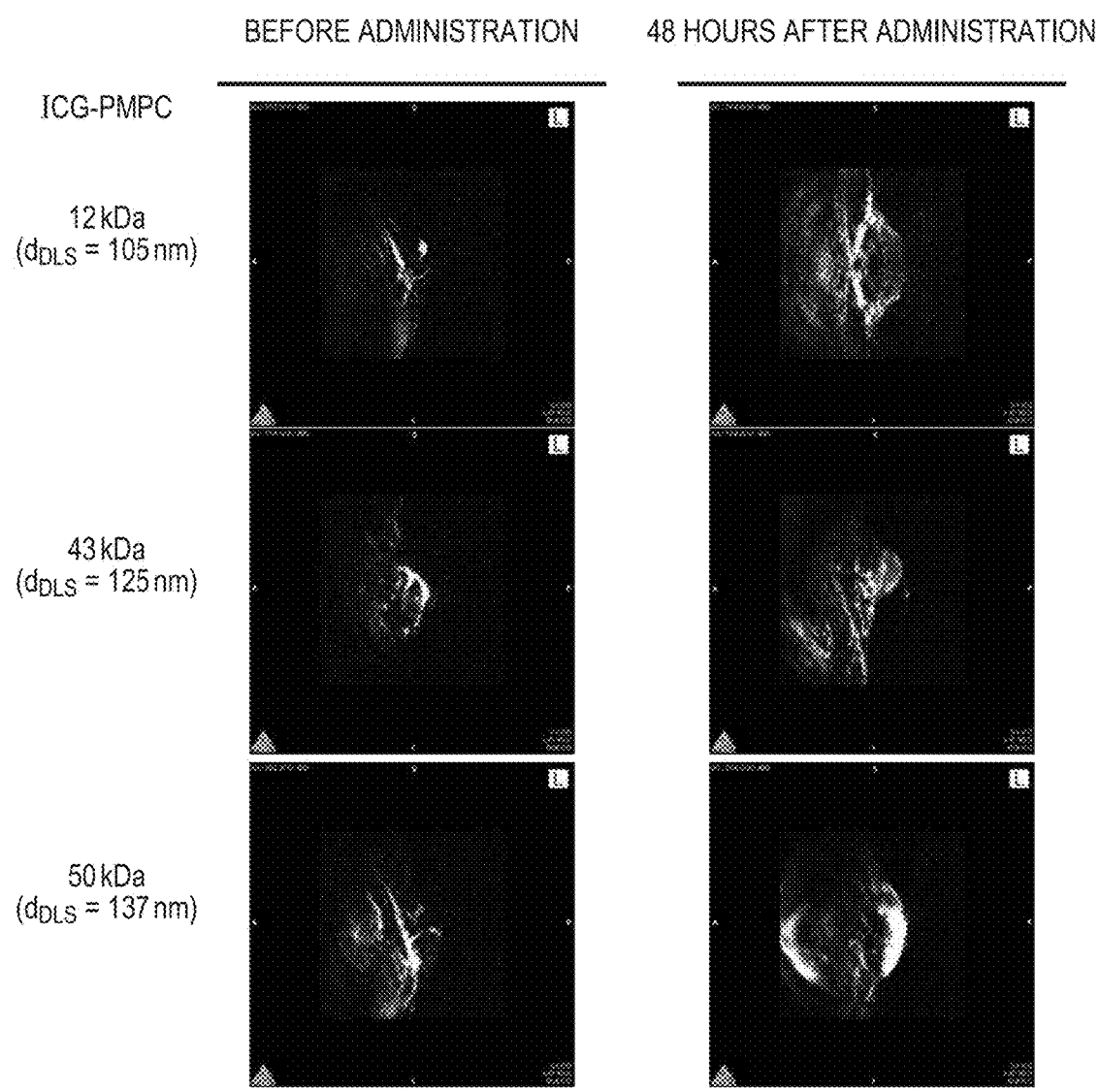
FIG. 13 illustrates photoacoustic imaging images of a tumor region of a cancer-bearing mouse to which each of ICG-PMPC (12 k), ICG-PMPC (43 k) and ICG-PMPC (50 k) according to Examples of the present invention is administered.

FIG. 13 illustrates a photoacoustic imaging image of a tumor region of the cancer-bearing mouse to which each of ICG-PMPC (12 k), ICG-PMPC (43 k) and ICG-PMPC (50 k) was administered. FIG. 13 illustrates the photoacoustic image of the cancer-bearing mouse before administration, and the photoacoustic image of the same mouse individual two days after administration. As is clear from FIG. 13, the photoacoustic signal of a tumor site was observed to be enhanced according to an increase in the molecular weight of PMPC of ICG-PMPC.

Example 21

Evaluation of Localization of ICG-PMPC in Tumor

Figure 14:
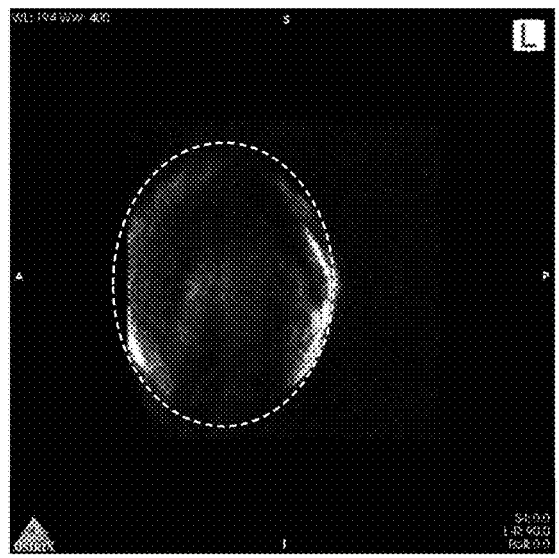
FIG. 14 is a photoacoustic imaging image of a tumor resected from a cancer-bearing mouse to which ICG-PMPC (50 k) according to Example of the present invention is administered. The dotted line in the Figure indicates a tumor position.

Localization of ICG-PMPC in a tumor was evaluated by photoacoustic imaging of the tumor resected from the cancer-bearing mouse, performed in Example 20. The cancer-bearing mouse to which ICG-PMPC (50 k) obtained in Example 20 was administered was euthanized by Somnopentyl at 48 hours after administration, and thereafter the tumor was surgically resected. Photoacoustic imaging (detection wavelengths: 797 nm and 850 nm) of the tumor resected was performed. FIG. 14 illustrates the photoacoustic imaging image of the tumor resected. The tumor site is indicated by a dotted line. As is clear from FIG. 14, ICG-PMPC (50 k) accumulated in the tumor was found to be localized on the tumor surface.

Example 22

Coupling Reaction of Sulfo-Cyanine 7 NHS Ester

PMPC-NH$_2$ represented by the formula (45) (96.5 mg, 1.64 μmol), a near-infrared dye Sulfo-Cyanine 7 NHS Ester (produced by Lumiprobe GmbH) (3.7 mg, 4.5 μmol) and 1.0 mL of dehydrated methanol (produced by Wako Pure Chemical Industries, Ltd.) were added into a 5-mL vial, and stirred at room temperature under light shielding for 50 hours. After completion of the reaction, the reaction solution was diluted with ultrapure water, and the solution was transferred to an Amicon Ultra ultrafiltration filter tube (molecular weight cut off: 10K), centrifuged (5000 g) for 30 minutes and concentrated. Ultrapure water was added to the concentrated solution, and centrifuged (5000 g) for 30 minutes again. The operation was repeated twice, the resulting crude product was fractionated and purified by a PD-10 column (developing solvent: ultrapure water), and freeze-dried, and thereafter Cy7-PMPC represented by the following formula (47) (green solid, Mn=58000) was obtained.

$^1$H NMR spectrum (500 MHz, CD$_3$OD) δ/ppm=7.75-7.91 (m), 7.50-7.57 (m), 6.19-6.26 (m), 4.56-4.59 (m), 4.32 (br), 4.21 (br), 4.07 (br), 3.74 (br), 3.16 (s) 1.75-2.12 (br), 0.82-1.18 (br).

(47)

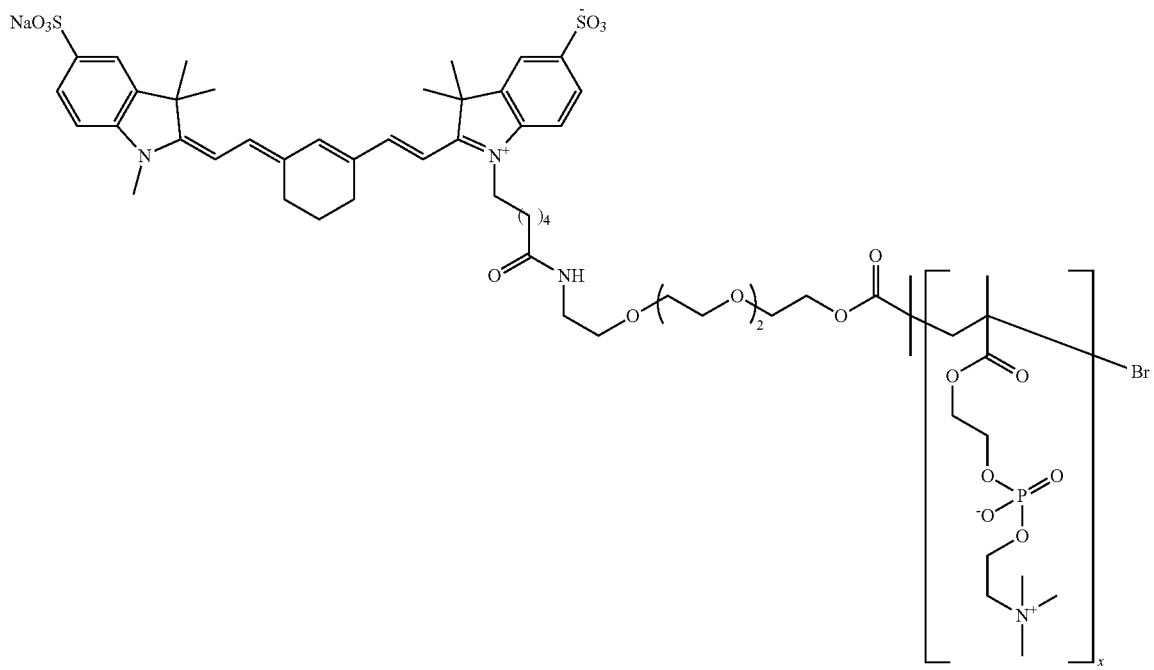

Example 23

Coupling Reaction of IR Dye (Registered Trademark) 700DX NHS Ester

PMPC-NH$_2$ represented by the formula (45) (67.4 mg, 1.14 μmol), IR Dye (registered trademark) 700DX NHS Ester (produced by LI-COR, Inc.) (3.7 mg, 4.5 μmol) as a near-infrared dye, and 1.0 mL of dehydrated methanol (produced by Wako Pure Chemical Industries, Ltd.) were added into a 5-mL vial, and stirred at room temperature under light shielding for 68 hours. After completion of the reaction, the reaction solution was diluted with ultrapure water, and the solution was transferred to an Amicon Ultra ultrafiltration filter tube (molecular weight cut off: 10K), centrifuged (5000 g) for 30 minutes and concentrated. Ultrapure water was added to the concentrated solution, and centrifuged (5000 g) for 30 minutes again. The operation was repeated twice, the resulting crude product was fractionated and purified by a PD-10 column (developing solvent: ultrapure water), and freeze-dried, and thereafter 700DX-PMPC represented by the following formula (48) (green solid, Mn=57000) was obtained.

$^1$H NMR spectrum (500 MHz, CD$_3$OD) δ/ppm=9.74-9.79 (br), 9.60-9.63 (m), 9.40-9.44 (m), 8.44-8.54 (m), 8.05-8.09 (m), 4.33 (br), 4.22 (br), 4.07 (br), 3.74 (br), 3.32 (s) 1.75-2.12 (br), 0.81-1.21 (br).

Example 24

Coupling Reaction of IR Dye (Registered Trademark) 800CW NHS Ester

PMPC-NH$_2$ represented by the formula (45) (29.6 mg, 0.50 μmol), IR Dye 800CW NHS Ester (produced by LI-COR, Inc.) (1.0 mg, 0.86 μmol) as a near-infrared dye and 1.0 mL of dehydrated methanol (produced by Wako Pure Chemical Industries, Ltd.) were added into a 5-mL vial, and stirred at room temperature under light shielding for 53 hours. After completion of the reaction, the reaction solution was diluted with ultrapure water, and the solution was transferred to an Amicon Ultra ultrafiltration filter tube (molecular weight cut off: 10K), centrifuged (5000 g) for 20 minutes and concentrated. Ultrapure water was added to the concentrated solution, and centrifuged (5000 g) for 20 minutes again. The operation was repeated twice, the resulting crude product was fractionated and purified by a PD-10 column (developing solvent: ultrapure water), and freeze-dried, and thereafter 800CW-PMPC represented by the following formula (49) (green solid, Mn=57000) was obtained. $^1$H NMR spectrum (500 MHz, CD$_3$OD) δ/ppm=7.92-8.03 (m), 7.77-7.88 (m), 7.35-7.41 (m), 7.25-7.33 (m), 7.17-7.22 (m), 6.27-6.33 (m), 6.15-6.23 (m), 4.33 (br), 4.22 (br), 4.07 (br), 3.74 (br), 3.30 (s) 1.72-2.12 (br), 0.84-1.22 (br).

(48)

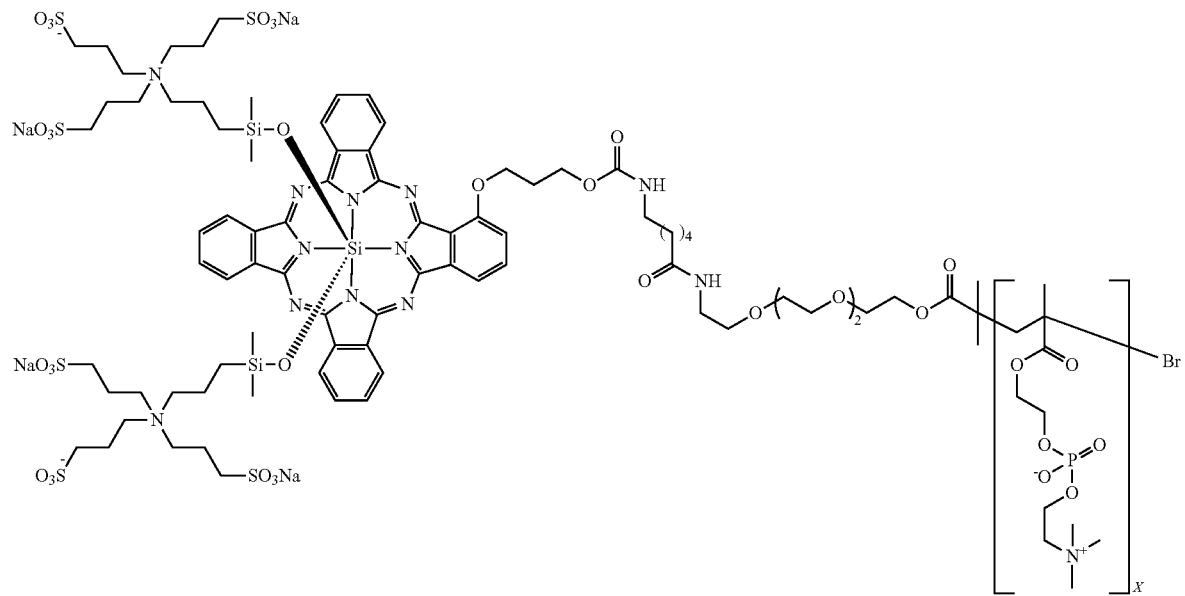

(49)

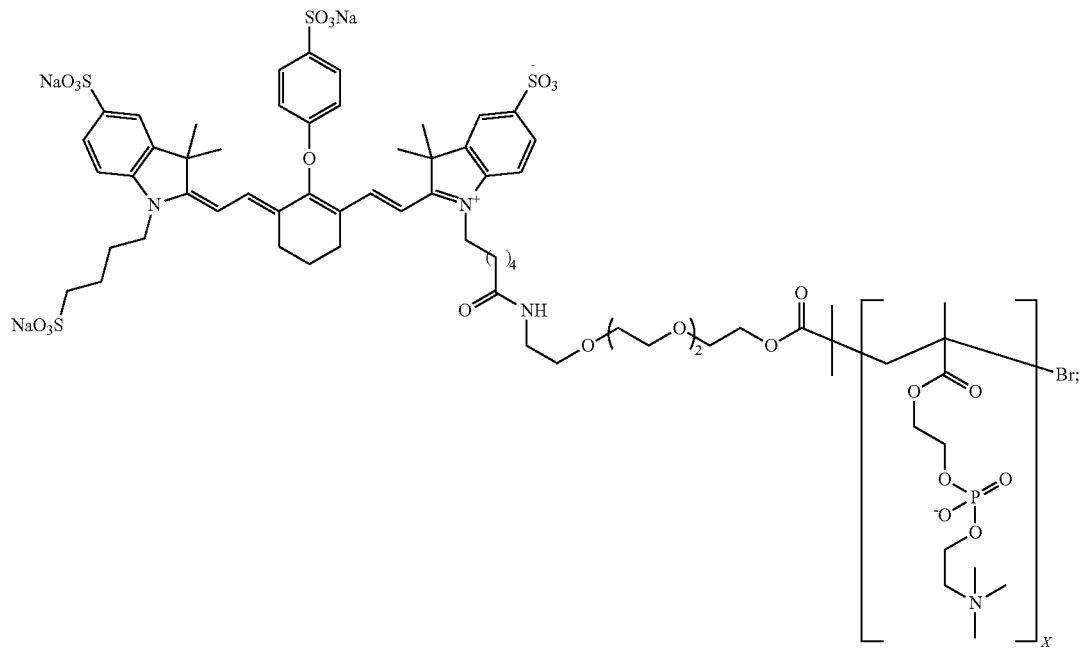

Example 25

Coupling Reaction of IR Dye (Registered Trademark) 800RS NHS Ester

PMPC-NH$_2$ represented by the formula (45) (60.5 mg, 1.03 μmol), a near-infrared dye IR Dye (registered trademark) 800RS NHS Ester (produced by LI-COR, Inc.) (2.1 mg, 2.2 μmol) and 1.0 mL of dehydrated methanol (produced by Wako Pure Chemical Industries, Ltd.) were added into a 5-mL vial, and stirred at room temperature under light shielding for 51 hours. After completion of the reaction, the reaction solution was diluted with ultrapure water, and the solution was transferred to an Amicon Ultra ultrafiltration filter tube (molecular weight cut off: 10K), centrifuged (5000 g) for 30 minutes and concentrated. Ultrapure water was added to the concentrated solution, and centrifuged (5000 g) for 20 minutes again. The operation was repeated three times, and the resulting crude product was fractionated and purified by a PD-10 column (developing solvent: ultrapure water), and freeze-dried, and thereafter 800RS-PMPC represented by the following formula (50) (green solid, Mn=57000) was obtained.

$^1$H NMR spectrum (500 MHz, CD$_3$OD) δ/ppm=7.88-8.00 (m), 7.83-7.87 (m), 7.14-7.42 (m), 6.21-6.26 (m), 6.11-6.15 (m), 4.33 (br), 4.22 (br), 4.07 (br), 3.74 (br), 3.30 (s) 1.75-2.13 (br), 0.85-1.22 (br).

(50)

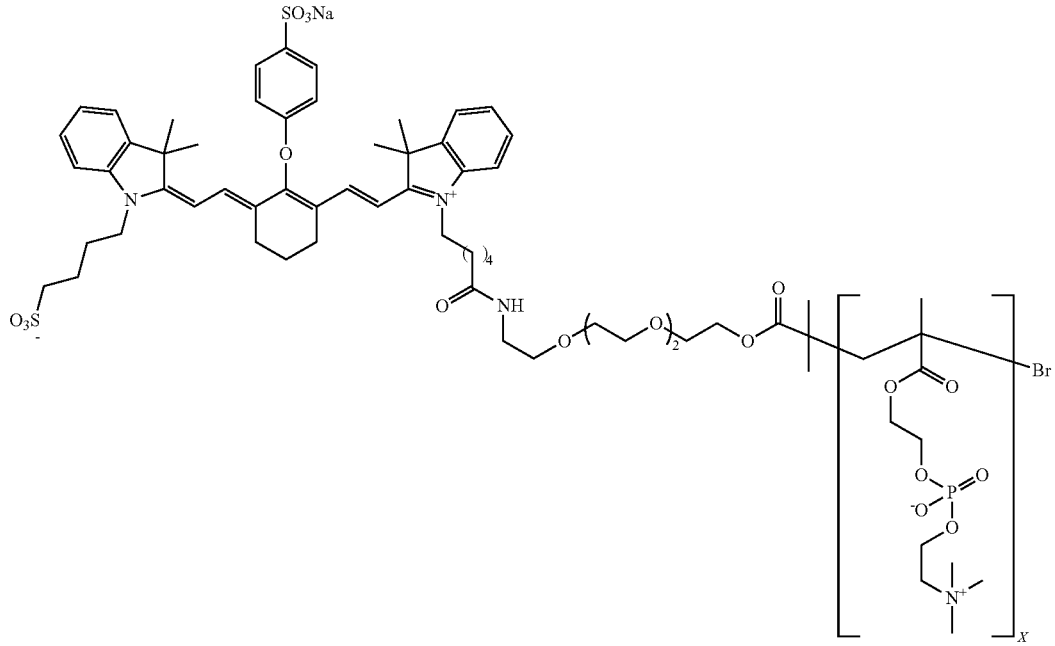

Example 26

Particle Size Measurement of Dye-bound PMPC

Dynamic light scattering measurements (measurement apparatus: Zeta Sizer Nano manufactured by Malvern Instruments) of respective aqueous solutions (1 mg/mL) of Cy7-PMPC (58 k) represented by the formula (47), 700DX-PMPC (57 k) represented by the formula (48), 800CW-PMPC (57 k) represented by the formula (49) and 800RS-PMPC (57 k) represented by the formula (50) obtained in Examples 22, 23, 24 and 25 were tried, but could not be performed. On the other hand, dynamic light scattering measurement of Cy7-PMPC (58 k) in an aqueous hydrochloric acid solution (pH: 0.46) was performed, and as a result, the Z average particle size was 12.3 nm on average.

Example 27

Absorption Spectrum Measurement of Dye-Bound PMPC

Absorption spectrum measurements (measurement apparatus: U-3010 Spectrophotometer manufactured by Hitachi Ltd.) of respective aqueous solutions (2 µM) of Cy7-PMPC (58 k) represented by the formula (47), 700DX-PMPC (57 k) represented by the formula (48), 800CW-PMPC (57 k) represented by the formula (49) and 800RS-PMPC (57 k) represented by the formula (50) obtained in Examples 22, 23, 24 and 25 were performed, and as a result, such compounds were found to have maximum absorption wavelengths of 753 nm, 689 nm, 777 nm and 771 nm, respectively.

Example 28

Evaluation of Tumor-imaging Ability of Dye-bound PMPC by Fluorescence Imaging With respect to each of Cy7-PMPC (58 k) represented by the formula (47), 700DX-PMPC (57 k) represented by the formula (48), 800CW-PMPC (57 k) represented by the formula (49) and 800RS-PMPC (57 k) represented by the formula (50) obtained in Examples 22, 23, 24 and 25, respectively, and ICG-PMPC having a molecular weight of 48 k represented by formula (46) described in Example 12 (hereinafter, abbreviated as "ICG-PMPC (48 k)"), the tumor-imaging ability by fluorescence imaging was evaluated according to the method described in Example 4. The amount of each compound to be administered was 50 nmol per mouse as the amount of each dye, and each compound was injected as about 100 µL of a PBS solution to the tail vein of each mouse. The fluorescent intensities of a tumor site and a normal site were quantified from the fluorescence image of each mouse at 24 hours after administration of the dye-bound PMPC of the present invention, according to the method described in Example 4. In the fluorescence imaging, an excitation filter of 675 nm and a fluorescence filter of 720 nm were used for 700DX-PMPC (57 k), an excitation filter of 745 nm and a fluorescence filter of 800 nm were used for Cy7-PMPC (58 k), 800CW-PMPC (57 k) and 800RS-PMPC (57 k), and an excitation filter of 745 nm and a fluorescence filter of 840 nm were used for ICG-PMPC (48 k).

Figure 15:
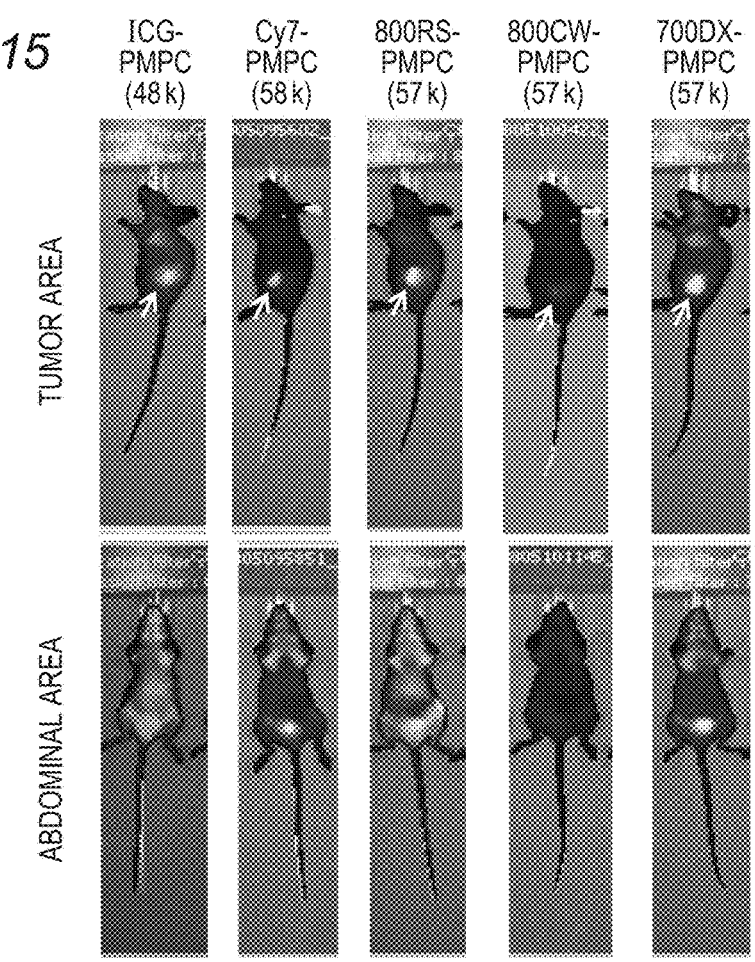
FIG. 15 illustrates a superimposed view of a near-infrared fluorescent image and a bright field image of each cancer-bearing mouse at 24 hours after administration of each of ICG-PMPC (48 k), Cy7-PMPC (58 k), 800RS-PMPC (57 k), 800CW-PMPC (57 k) and 700DX-PMPC (57 k) according to Examples of the present invention (in the Figure, each white arrow indicates a tumor site). Each fluorescence image is a grayscale image in which each contrast is arbitrarily adjusted, and a low fluorescent intensity is exhibited in each black region and a high fluorescent intensity is exhibited in each white region.

FIG. 15 illustrates one example of a superimposed view of a near-infrared fluorescent image and a bright field image of each cancer-bearing mouse at 24 hours after administration of each dye-bound PMPC. FIG. 15 illustrates a tumor area and an abdominal area of the same mouse. Each white arrow in the image of the tumor area indicates a tumor site. All the dye-bound PMPCs could allow for imaging of a tumor by fluorescence. As is clear from the image of the abdominal area, fluorescence was observed from the bladder with respect to each of Cy7-PMPC (58 k) and 700DX-PMPC (57 k), and therefore renal excretion of each of such dye-bound PMPCs was supposed.

Table 3 shows the SNR as the index of the tumor-imaging ability of each dye-bound PMPC. The SNRs of all the dye-bound PMPCs were 1.7 or more, and tumor imaging could be conducted. In particular, the SNR of each of Cy7-PMPC (58 k) and 800CW-PMPC (57 k) was 2.0 or more, and such dye-bound PMPCs were shown to be excellent in tumor-imaging ability.

TABLE 3

SNR of dye-bound PMPC

| | Dye-bound PMPC | SNR |
|---|---|---|
| Example | ICG-PMPC (48k) | 1.7 |
| Example | Cy7-PMPC (58k) | 2.6 |
| Example | 800RS-PMPC (57k) | 1.9 |
| Example | 800CW-PMPC (57k) | 2.2 |
| Example | 700DX-PMPC (57k) | 1.8 |

Example 29

Evaluation of Tumor/Liver Ratio of Dye-bound PMPC by Fluorescence Imaging

The tumor/liver ratio (Tumor/Liver) of each of Cy7-PMPC (58 k), 700DX-PMPC (57 k), 800CW-PMPC (57 k), 800RS-PMPC (57 k) and ICG-PMPC (48 k) was calculated from the fluorescence imaging data obtained in Example 28. The tumor/liver ratio is expressed as the ratio of the fluorescent intensity of a tumor to the fluorescent intensity of the liver (measured area: $0.2\ cm^2$), and is one index of the tumor selectivity of each dye-bound PMPC.

Table 4 shows the tumor/liver ratio of each dye-bound PMPC. The tumor/liver ratios of all the dye-bound PMPCs were 1.8 or more, and were high values. In particular, the tumor/liver ratio of Cy7-PMPC (58 k) was 2.9, and was the highest value among the ratios of such dye-bound PMPCs.

TABLE 4

Tumor/liver ratio of dye-bound PMPC

| | Dye-bound PMPC | Tumor/liver ratio (Tumor/Liver) |
|---|---|---|
| Example | ICG-PMPC (48k) | 1.8 |
| Example | Cy7-PMPC (58k) | 2.9 |
| Example | 800RS-PMPC (57k) | 2.0 |
| Example | 800CW-PMPC (57k) | 2.2 |
| Example | 700DX-PMPC (57k) | 2.2 |

Example 30

Evaluations of Tumor Accumulation Property and Residual Rate in Blood of Dye-bound PMPC The amount of the dye in a tumor and the amount of the dye in blood with respect to each mouse in the tumor-imaging experiment performed in Example 28 were quantitatively determined to thereby evaluate the tumor accumulation property, the residual rate in blood and the tumor/blood ratio of each of Cy7-PMPC (58 k), 700DX-PMPC (57 k), 800CW-PMPC (57 k), 800RS-PMPC (57 k) and ICG-PMPC (48 k), according to the method described in Example 5.

The results are shown in Table 5. The dye-bound PMPC of the present invention exhibited a high tumor accumulation property, and in particular, 700DX-PMPC (57 k) exhibited a high value. It has been found that in vivo kinetics of the dye-bound PMPC according to each Example of the present invention vary depending on the difference in the dye to be bound. It is considered that hydrophilicity and hydrophobicity of the dye have an effect on in vivo kinetics. It has been revealed from the results that the dye-bound PMPC according to each Example of the present invention can be controlled in terms of the function thereof by the type of the dye and the molecular weight of a polymer, and the embodiment thereof can be optimized depending on the purpose of diagnosis.

TABLE 5

Tumor accumulation property, residual rate in blood and tumor/blood ratio of dye-bound PMPC

|  | Dye-bound PMPC | Tumor accumulation property (% ID/g) | Residual rate in blood (% ID/g) | Tumor/blood ratio (Tumor/Blood) |
|---|---|---|---|---|
| Example | ICG-PMPC (48k) | 8.0 | 5.5 | 1.5 |
| Example | Cy7-PMPC (58k) | 4.1 | 6.5 | 0.6 |
| Example | 800RS-PMPC (57k) | 7.8 | 6.9 | 1.1 |
| Example | 800CW-PMPC (57k) | 3.4 | 2.8 | 1.2 |
| Example | 700DX-PMPC (57k) | 10.8 | 9.0 | 1.2 |

Example 31

Evaluation of Biodistribution of Dye-bound PMPC

In order to examine the biodistribution of each dye-bound PMPC, the tissue of the mouse subjected to the tumor-imaging experiment performed in Example 28 was resected, and subjected to measurement of the amount of fluorescence, together with the tumor tissue resected in Example 30. Specifically, the normalized fluorescent intensity of each of the tissues was measured. The normalized fluorescent intensity here means the average radiant efficiency ($[p/s/cm^2/sr]/[\mu W/cm^2]$) quantified using the analysis software associated with a fluorescence imaging apparatus. The average radiant efficiency means the amount of light to be emitted, normalized by the measured area and the amount of excitation light applied. In addition, the ratio of the fluorescent intensity of a tumor to the fluorescent intensity of each tissue (abbreviated as "tumor/normal tissue") was also calculated. The tumor/normal tissue is one index representing the tumor selectivity of each of the dye-bound PMPCs, and a higher value means a higher selectivity to a tumor.

Table 6 shows the normalized fluorescent intensity and the tumor/normal tissue of each of the dye-bound PMPCs in each tissue. All the dye-bound PMPCs were observed to be distributed in a normal tissue, but a tumor exhibited a fluorescent intensity equal to or higher than that of a normal tissue. Therefore, a high tumor selectivity of the dye-bound PMPC of the present invention is considered to be reflected. Cy7-PMPC (58 k) exhibited a high tumor/normal tissue value, and was found to be a dye-bound PMPC high in tumor selectivity.

TABLE 6

Normalized fluorescent intensity and tumor/normal tissue of dye-bound PMPC in each tissue

| | ICG-PMPC (48k) | | Cy7-PMPC (58k) | | 800RS-PMPC (57k) | | 800CW-PMPC (57k) | | 700DX-PMPC (57k) | |
|---|---|---|---|---|---|---|---|---|---|---|
| | Normalized fluorescent intensity | Tumor/normal tissue | Normalized fluorescent intensity | Tumor/normal tissue | Normalized fluorescent intensity | Tumor/normal tissue | Normalized fluorescent intensity | Tumor/normal tissue | Normalized fluorescent intensity | Tumor/normal tissue |
| Heart | 9.9E+08 | 1.5 | 6.4E+08 | 4.0 | 2.3E+09 | 1.5 | 5.3E+08 | 3.8 | 7.5E+08 | 2.4 |
| Lung | 1.7E+09 | 0.8 | 1.0E+09 | 2.6 | 2.8E+09 | 1.2 | 1.0E+09 | 2.0 | 2.3E+09 | 0.8 |
| Liver | 1.9E+09 | 0.8 | 2.1E+09 | 1.3 | 3.7E+09 | 0.9 | 1.8E+09 | 1.1 | 1.2E+09 | 1.5 |
| Kidney | 1.3E+09 | 1.2 | 1.2E+09 | 2.2 | 2.0E+09 | 1.7 | 9.0E+08 | 2.2 | 1.7E+09 | 1.1 |
| Spleen | 5.8E+08 | 2.5 | 6.5E+08 | 4.0 | 1.3E+09 | 2.7 | 5.5E+08 | 3.7 | 3.9E+08 | 4.5 |
| Pancreas | 8.1E+08 | 1.8 | 8.0E+08 | 3.2 | 1.3E+09 | 2.7 | 6.1E+08 | 3.3 | 9.5E+08 | 1.9 |
| Intestine | 1.4E+09 | 1.0 | 9.2E+08 | 2.8 | 1.9E+09 | 1.9 | 8.0E+08 | 2.5 | 1.2E+09 | 1.5 |
| Stomach | 5.7E+08 | 2.6 | 5.7E+08 | 4.6 | 1.5E+09 | 2.3 | 6.3E+08 | 3.2 | 1.7E+09 | 1.1 |
| Muscle | 2.2E+08 | 6.7 | 3.3E+08 | 7.9 | 9.4E+08 | 3.7 | 4.3E+08 | 4.7 | 5.4E+08 | 3.3 |
| Skin | 1.4E+09 | 1.0 | 1.9E+09 | 1.4 | 3.2E+09 | 1.1 | 2.0E+09 | 1.0 | 2.6E+09 | 0.7 |
| Tumor | 1.5E+09 | 1.0 | 2.6E+09 | 1.0 | 3.5E+09 | 1.0 | 2.0E+09 | 1.0 | 1.8E+09 | 1.0 |

Example 32

Evaluation of Photo-fading Process of Dye-bound PMPC

With respect to each of Cy7-PMPC (58 k) represented by the formula (47), 700DX-PMPC (57 k) represented by the formula (48), 800CW-PMPC (57 k) represented by the formula (49) and 800RS-PMPC (57 k) represented by the formula (50) obtained in Examples 22, 23, 24 and 25, respectively, and ICG-PMPC (48 k) represented by formula (46) described in Example 12, 2.0 mL of a sample was prepared in which the concentration of each dye-bound PMPC was adjusted so that the absorbance at the maximum absorption wavelength was 0.15. A sample of single ICG as Comparative Example was also prepared. Herein, the irradiation wavelength of near-infrared pulse laser light by use of the PAT apparatus and the excitation wavelength in fluorescence spectrum measurement were set to be the maximum absorption wavelengths of each dye-bound PMPC and ICG. Herein, the excitation wavelengths and the fluorescence emission wavelengths of each dye-bound PMPC and ICG were summarized in FIG. 16. The amount of near-infrared pulse laser light was set to be 8 to 9 mJ at each wavelength, and irradiation at 120 points (detector position) per 20 times was defined as one irradiation and such irradiation was performed at most four times. After each irradiation, sampling was conducted by 150 μL. The resultant sample was placed in a 100-μL cuvette, subjected to fluorescence spectrum measurement (FP-6300 manufactured by JASCO Corporation), and studied with respect to photo-fading. The results are illustrated in FIG. 17. A stable dye-bound PMPC in which photo-fading was least caused was 700DX-PMPC (57 k) having a silicon phthalocyanine backbone as the near-infrared fluorescent dye. On the other hand, clear photo-fading was observed in other dye-bound PMPCs having a cyanine type dye, and the stability was decreased in the order of 800CW-PMPC (57 k)>ICG-PMPC (48 k)>800RS-PMPC (57 k)≈Cy7-PMPC (58 k). Furthermore, photo-fading to about 15% was caused by four times of irradiation in the case of single ICG as Comparative Example, and therefore it was revealed that binding to PMPC remarkably enhanced the stability of a cyanine type dye.

Example 33

Evaluation of Amount of Singlet Oxygen Generated from Dye-bound PMPC

With respect to each of Cy7-PMPC (58 k) represented by the formula (47), 700DX-PMPC (57 k) represented by the formula (48), 800CW-PMPC (57 k) represented by the formula (49) and 800RS-PMPC (57 k) represented by the formula (50) obtained in Examples 22, 23, 24 and 25, respectively, and ICG-PMPC (48 k) represented by formula (46) described in Example 12, 2.0 mL of a sample was prepared in which the concentration of each dye-bound PMPC was prepared so that the absorbance at the maximum absorption wavelength was 0.15. Next, an aqueous solution of Singlet Oxygen Sensor Green Reagent (produced by Molecular PROBES) prepared at 1.0 mM was added to an aqueous solution of each dye-bound PMPC by 2.0 μL, irradiated with near-infrared pulse laser light at most four times by using the PAT apparatus as in Example 32, and sampled after each irradiation by 150 μL. The resultant sample was placed in a 100-μL cuvette and subjected to fluorescence spectrum measurement (FP-6300 manufactured by JASCO Corporation), and the amount of singlet oxygen generated was demonstrated. Herein, while the Singlet Oxygen Sensor Green Reagent in the case of no singlet oxygen present exhibited weak blue fluorescence (Ex: 372 and 393 nm; Em: 395 and 416 nm), the Singlet Oxygen Sensor Green Reagent in the case of singlet oxygen present exhibited green fluorescence (Ex: about 504 nm; Em: 525 nm).

Figure 18:
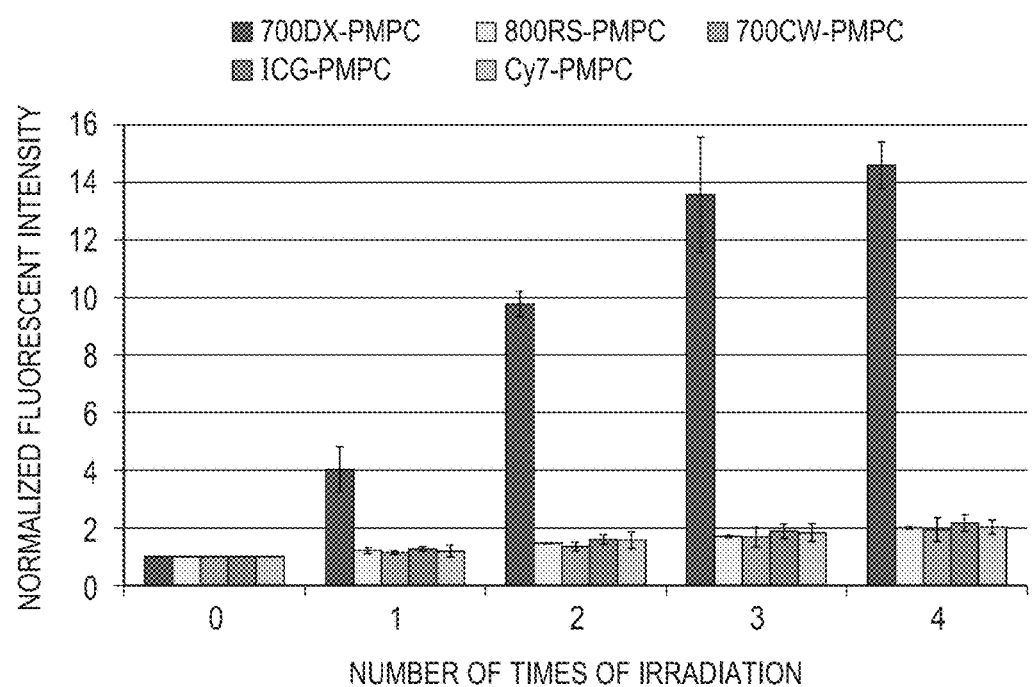
FIG. 18 is a diagram illustrating the relationship between the amount of singlet oxygen generated from each of ICG-PMPC (48 k), Cy7-PMPC (58 k), 800RS-PMPC (57 k), 800CW-PMPC (57 k) and 700DX-PMPC (57 k) according to Examples of the present invention, and the number of times of laser irradiation.

Accordingly, each dye-bound PMPC after light irradiation was excited by excitation light at 480 nm and subjected to fluorescence spectrum measurement for comparison of the fluorescent intensity at 536 nm, and the amount of singlet oxygen generated was evaluated. The results were illustrated in FIG. 18. It was revealed that 700DX-PMPC (57 k) having a silicon phthalocyanine backbone as the near-infrared fluorescent dye generated singlet oxygen in a much larger amount than other dye-bound PMPCs having a cyanine type dye. In fact, a phthalocyanine type dye is used in the photodynamic therapy for cancer in clinical practice, and is expected to exhibit strong cytotoxicity by light irradiation. On the other hand, it was revealed that the amount of singlet oxygen generated by light irradiation was extremely small in all the dye-bound PMPCs having a cyanine type dye. The results showed that, while fading was caused by irradiation with near-infrared pulse laser light in each of the dye-bound PMPCs having a cyanine type dye, generation of singlet oxygen was not included in the process of decomposing a cyanine type dye to be photo-faded, and it was supposed that almost no phototoxic property was exhibited.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-217451, filed Oct. 24, 2014, and Japanese Patent Application No. 2015-047073, filed Mar. 10, 2015, which are hereby incorporated by reference herein in their entirety.

The invention claimed is:
1. A polymer represented by any of formulae (1) to (7):
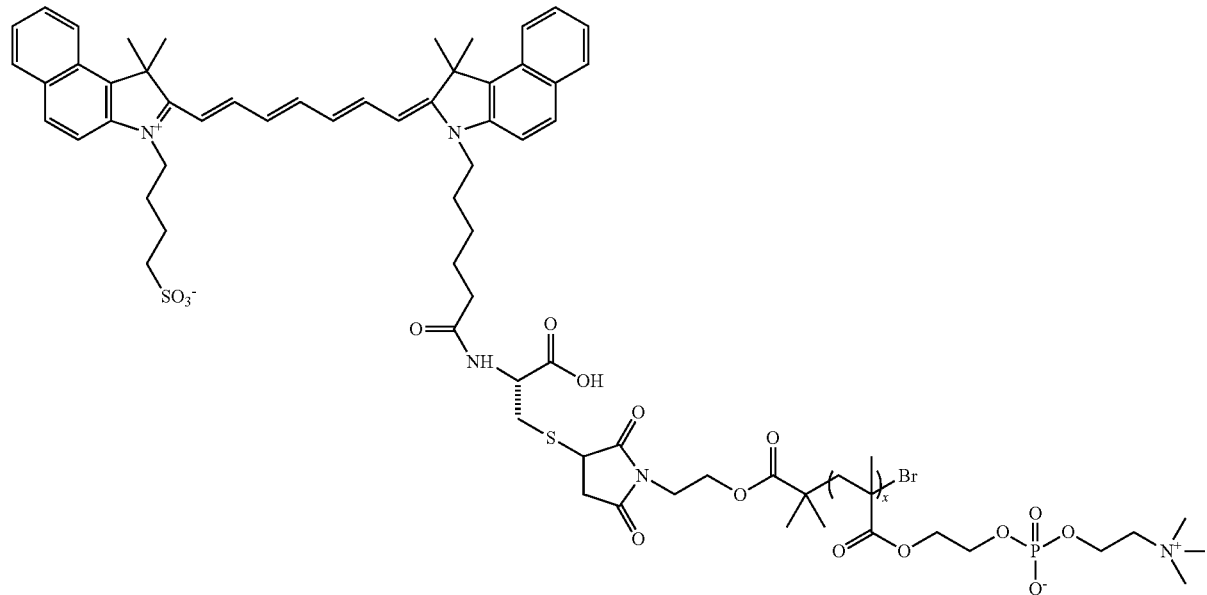
(1)
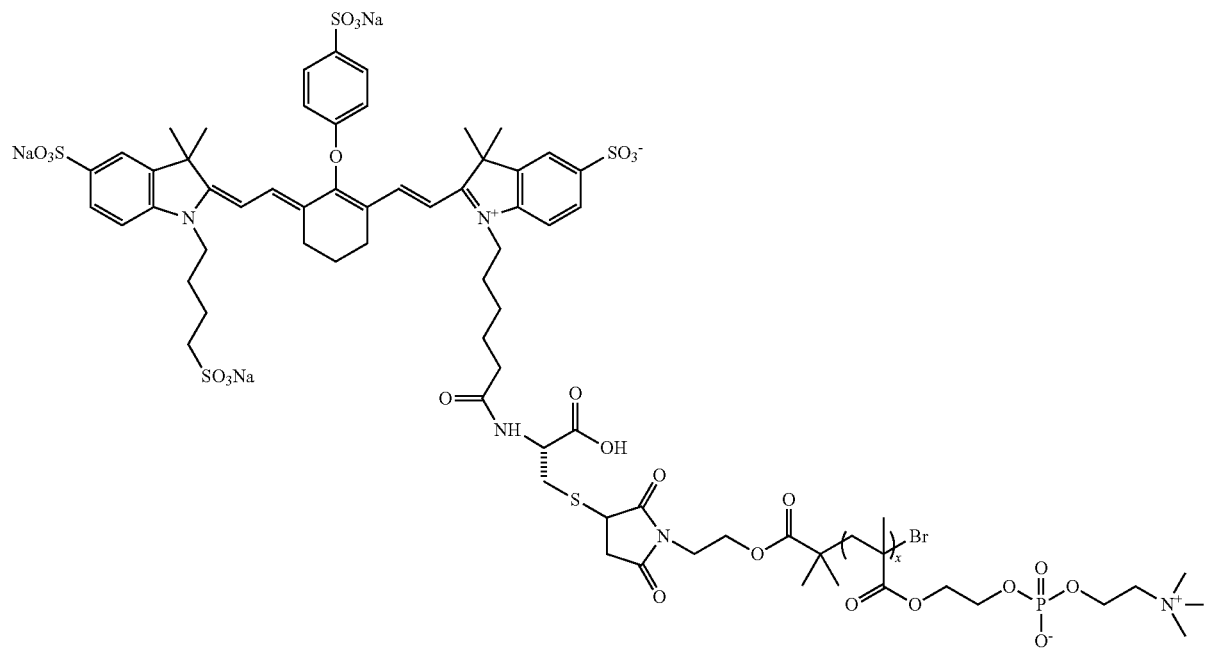
(2)

-continued
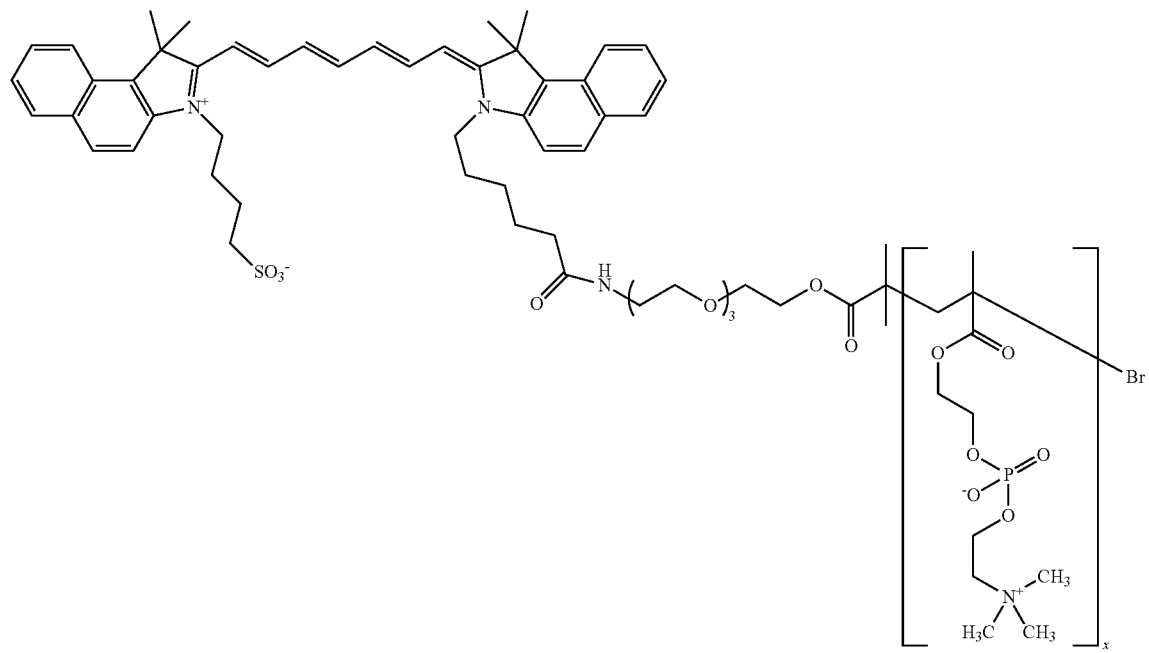
(3)
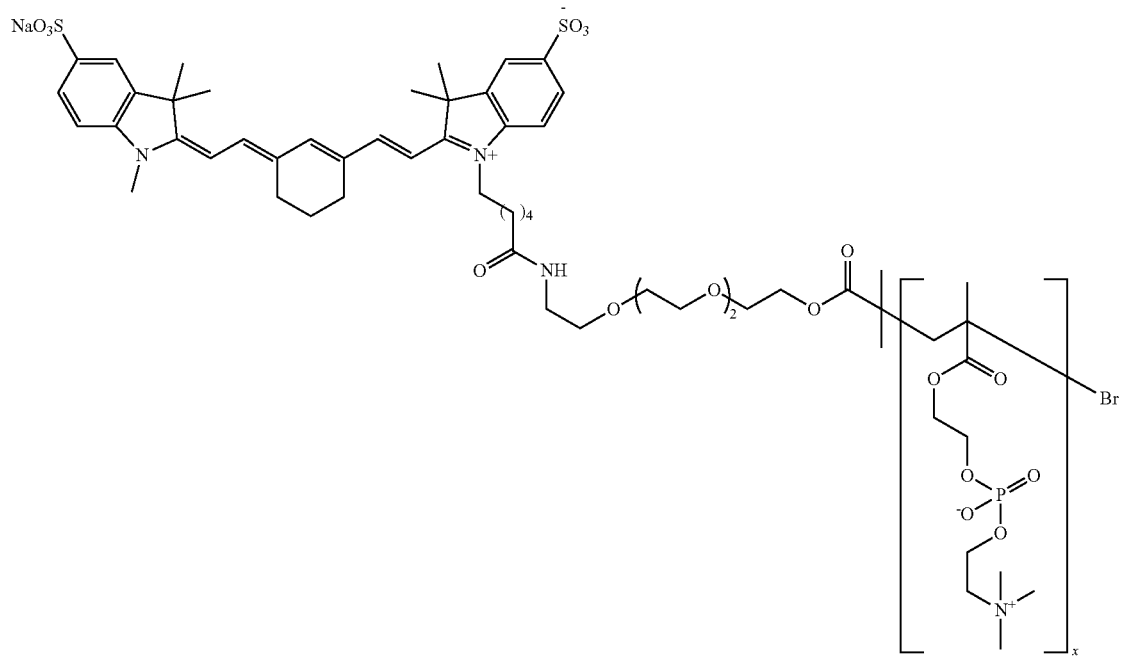
(4)

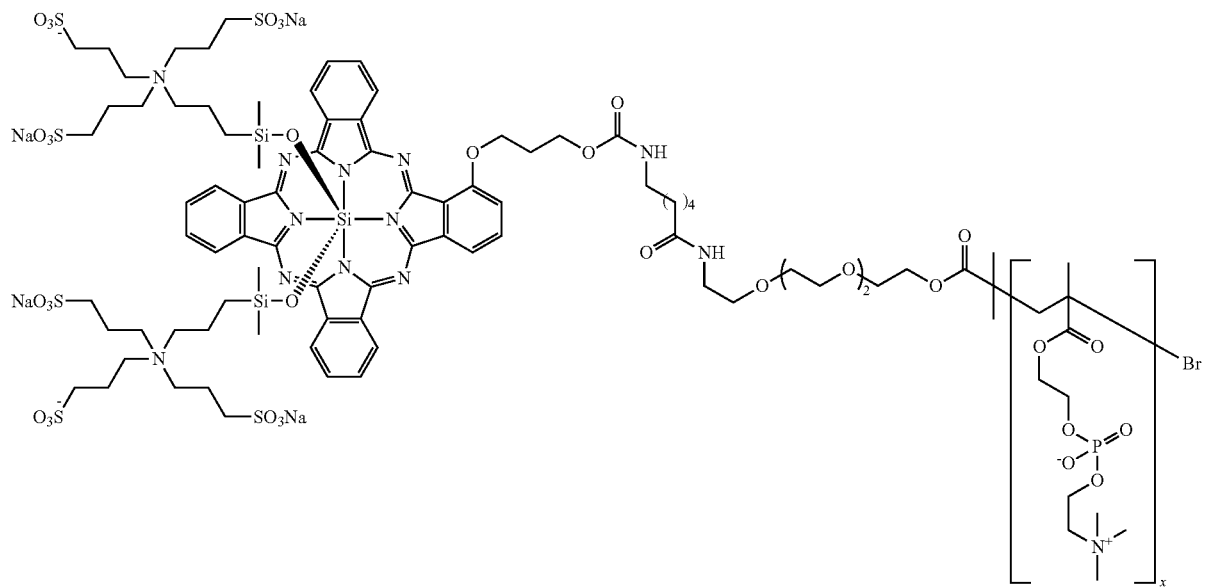
(5)
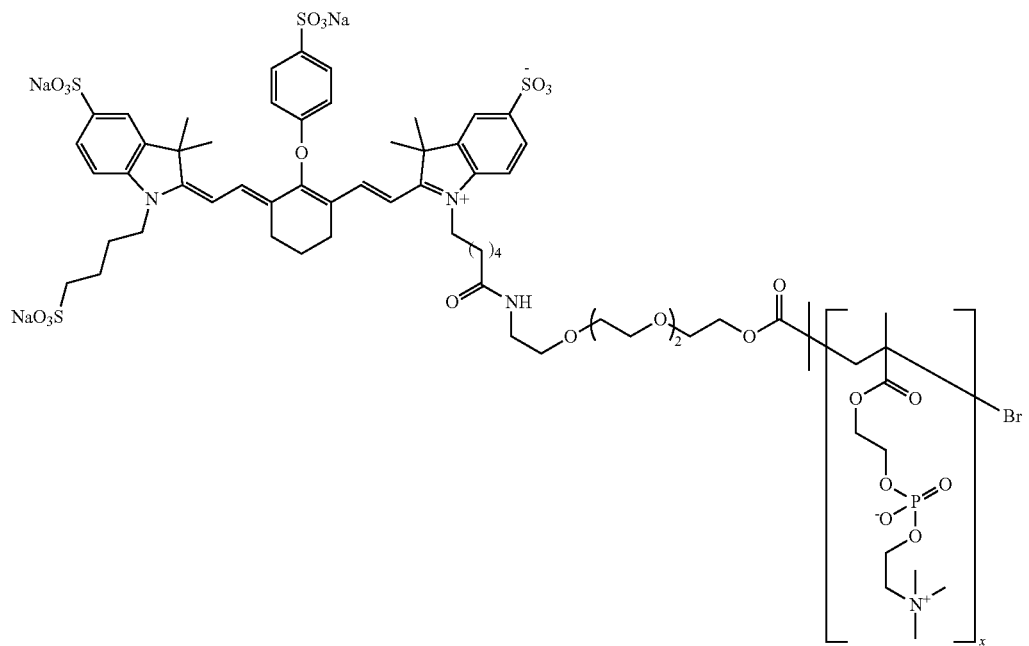
(6)

(7)

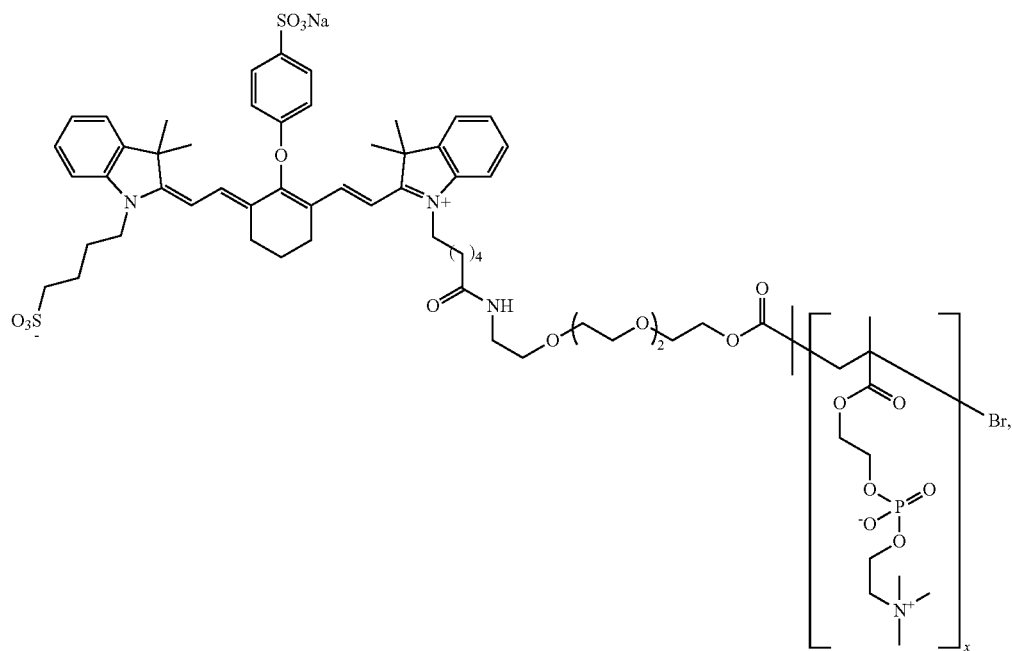

wherein in the formulae (1) to (7), each x represents an integer of 1 or more.

2. The polymer according to claim 1, wherein a number average molecular weight of the polymer is 5000 to 100000.

3. The polymer according to claim 1, wherein a number average molecular weight of the polymer is 9000 to 50000.

4. The polymer according to claim 1, wherein a number average molecular weight of the polymer is 16000 to 20000.

5. A contrast agent for photoacoustic imaging, comprising a polymer and a dispersion medium, wherein the polymer is represented by any of formulae (1) to (7):

(1)

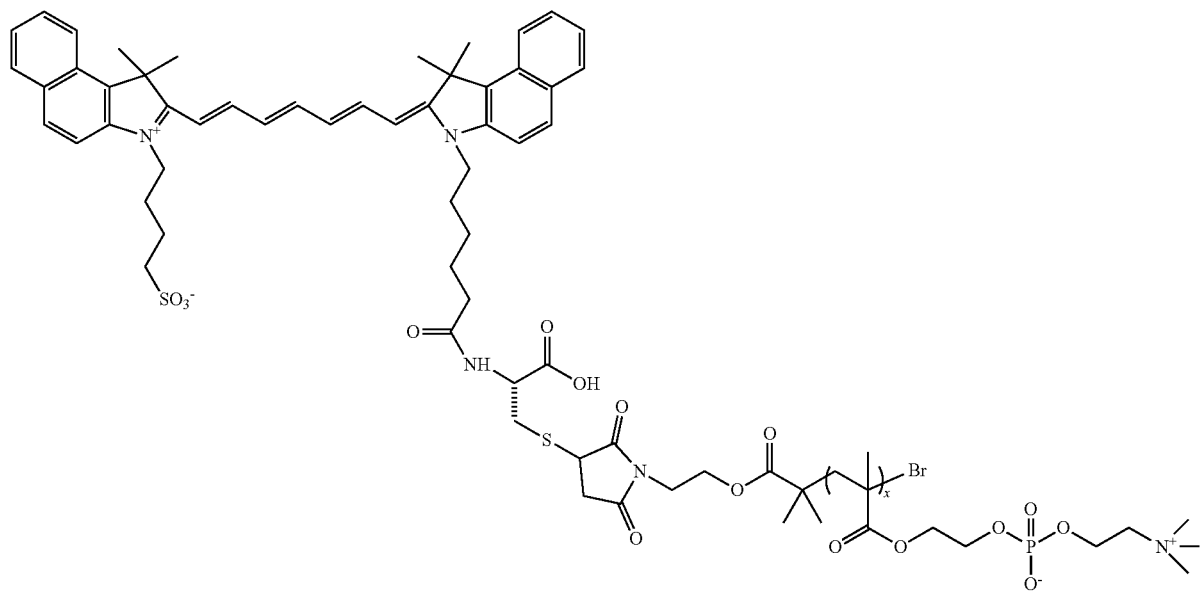

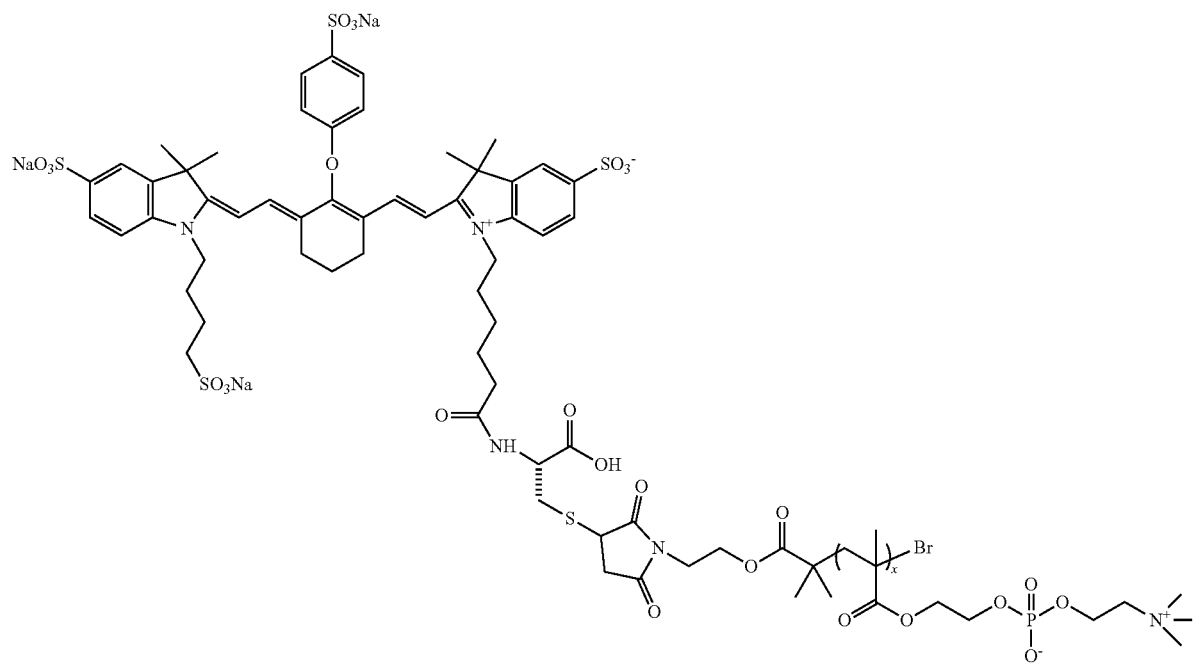
(2)
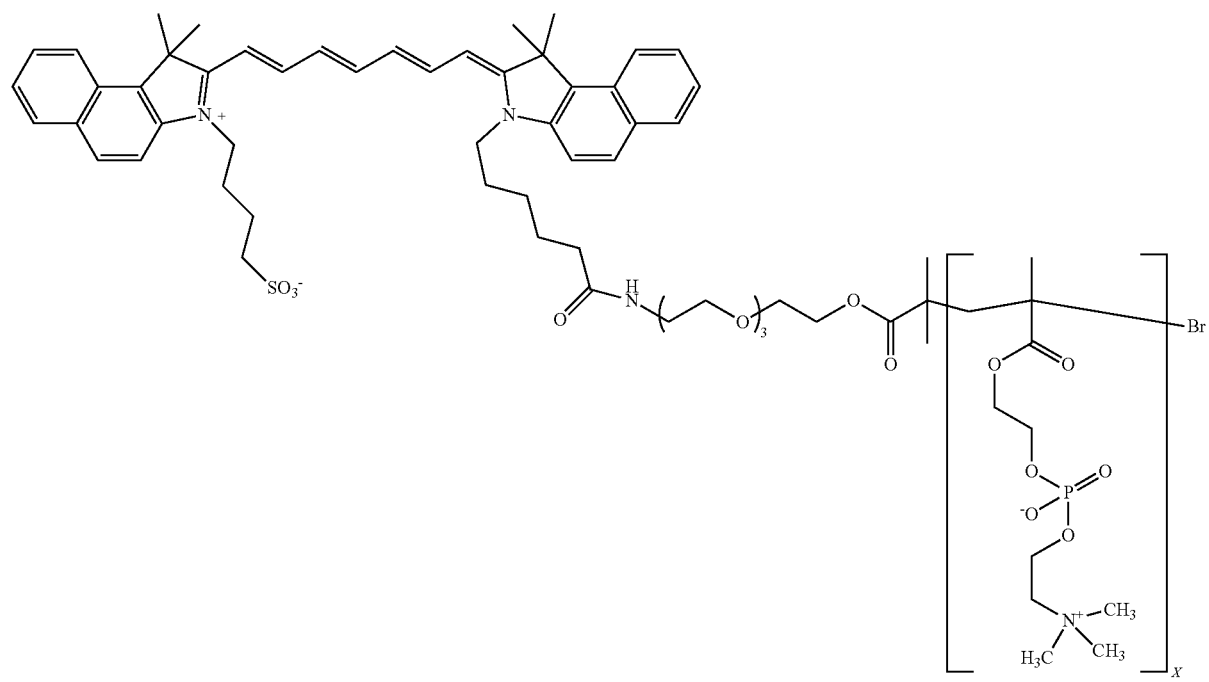
(3)

-continued
(4)
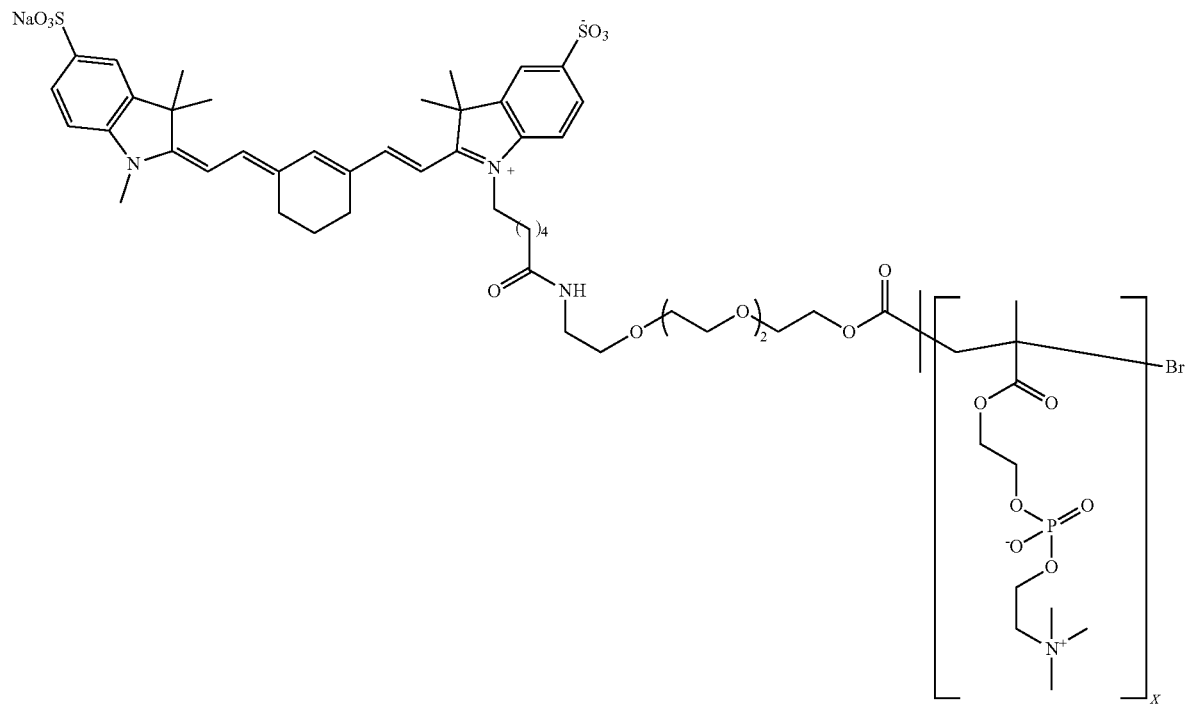
(5)
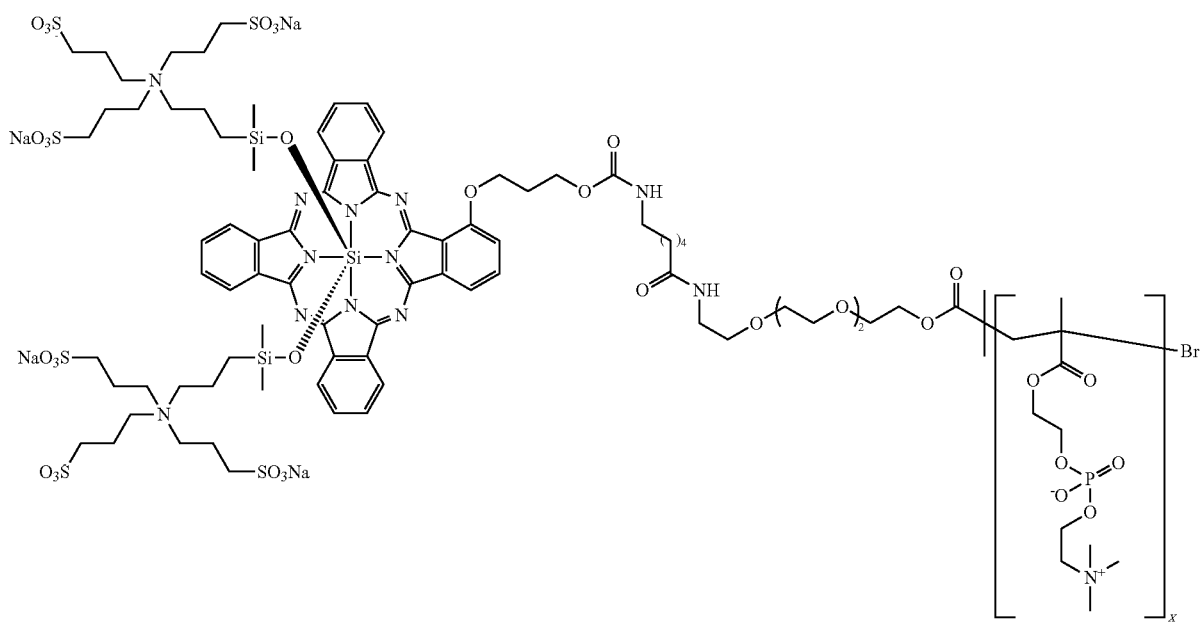

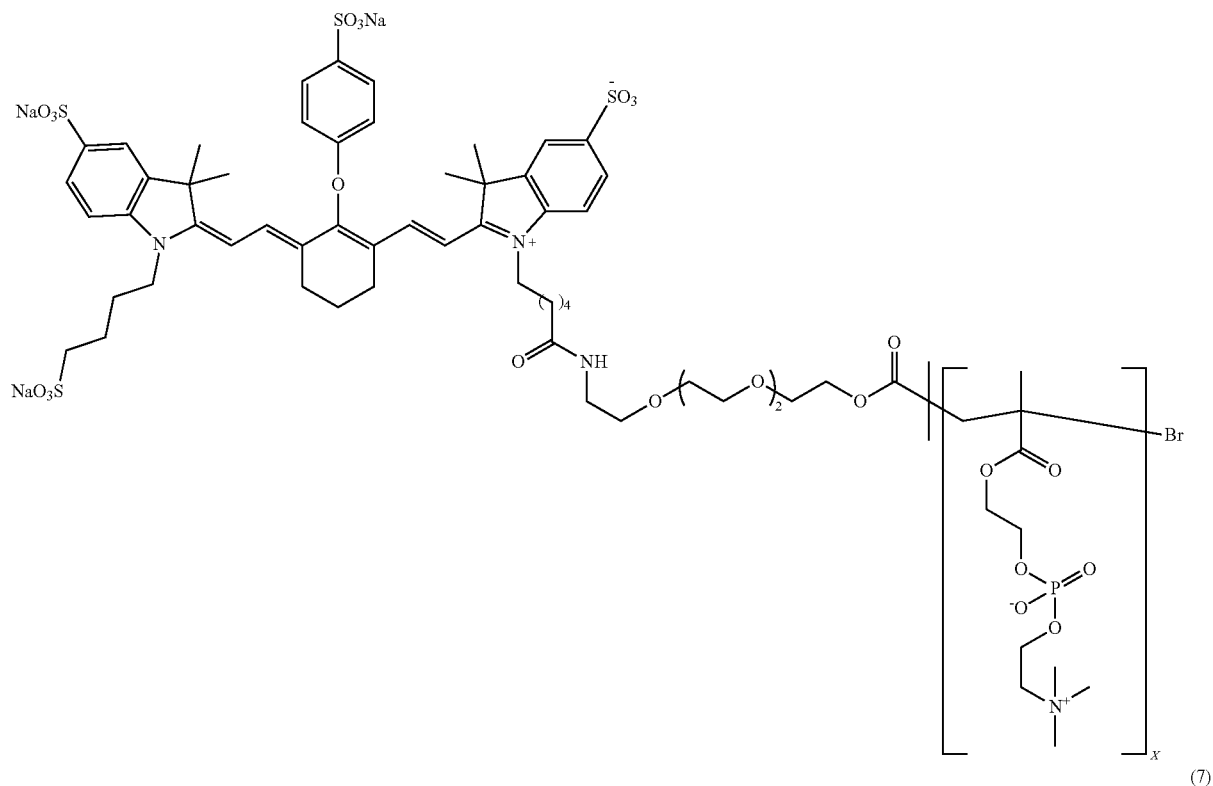
(6)
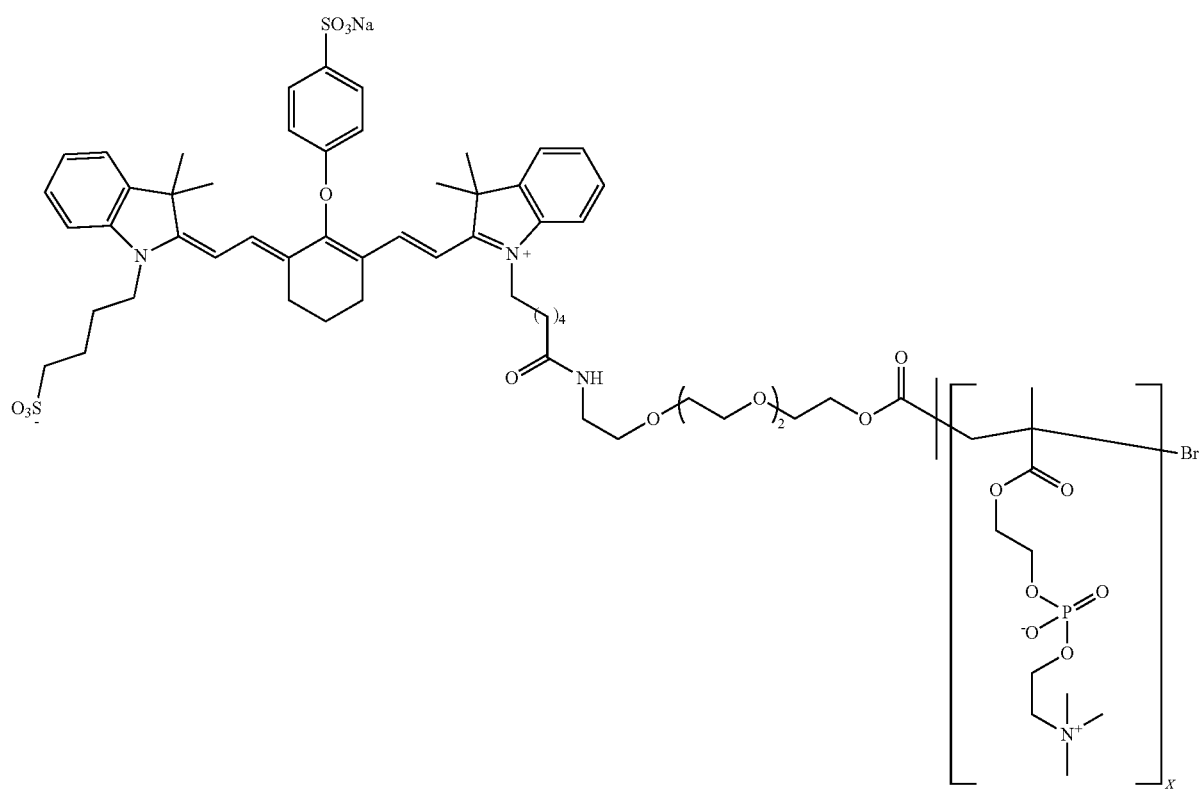
(7)
wherein in the formulae (1) to (7), each x represents an integer of 1 or more.
* * * * *